(12) United States Patent
Showalter et al.

(10) Patent No.: US 9,789,170 B2
(45) Date of Patent: Oct. 17, 2017

(54) ARGININE DEIMINASE WITH REDUCED CROSS-REACTIVITY TOWARD ADI-PEG 20 ANTIBODIES FOR CANCER TREATMENT

(71) Applicant: Polaris Group, Grand Cayman (KY)

(72) Inventors: Richard Showalter, El Cajon, CA (US); Robert Almassy, Vista, CA (US); James A. Thomson, San Diego, CA (US); Wes Sisson, San Diego, CA (US); Wei-Jong Shia, San Diego, CA (US); Li-Chang Chen, San Diego, CA (US); Yang Lee, San Diego, CA (US)

(73) Assignee: Polaris Group, Grand Cayman (KY)

( * ) Notice: Subject to any disclaimer, the term of this patent is extended or adjusted under 35 U.S.C. 154(b) by 0 days.

(21) Appl. No.: 14/855,661

(22) Filed: Sep. 16, 2015

(65) Prior Publication Data

US 2016/0074487 A1    Mar. 17, 2016

Related U.S. Application Data

(60) Provisional application No. 62/051,182, filed on Sep. 16, 2014.

(51) Int. Cl.
| | |
|---|---|
| A61K 38/43 | (2006.01) |
| A61K 38/50 | (2006.01) |
| A61K 47/48 | (2006.01) |
| A61K 45/06 | (2006.01) |
| C12N 9/78 | (2006.01) |

(52) U.S. Cl.
CPC .............. *A61K 38/50* (2013.01); *A61K 45/06* (2013.01); *A61K 47/48215* (2013.01); *C12N 9/78* (2013.01); *C12Y 305/03006* (2013.01)

(58) Field of Classification Search
CPC .......... C12Y 305/03006; A61K 38/164; A61K 38/43; A61K 5/06
See application file for complete search history.

(56) References Cited

U.S. PATENT DOCUMENTS

| | | | |
|---|---|---|---|
| 5,804,183 A | 9/1998 | Filpula et al. | |
| 6,132,713 A | 10/2000 | Fiipula et al. | |
| 6,180,387 B1 | 1/2001 | Biswas et al. | |
| 6,183,738 B1 | 2/2001 | Clark | |
| 6,635,462 B1 | 10/2003 | Ensor et al. | |
| 7,204,980 B2 | 4/2007 | Clark | |
| 7,323,167 B2 | 1/2008 | Clark et al. | |
| 7,413,735 B2 | 8/2008 | Min et al. | |
| 9,333,268 B2 | 5/2016 | Bomalaski et al. | |
| 2003/0215429 A1 | 11/2003 | de Simone | |
| 2004/0258675 A1 | 12/2004 | Ensor et al. | |
| 2005/0129706 A1 | 6/2005 | Clark | |
| 2006/0002915 A1 | 1/2006 | Min et al. | |
| 2007/0198198 A1 | 8/2007 | Burczynski et al. | |
| 2007/0212311 A1 | 9/2007 | Burne et al. | |
| 2009/0238813 A1 | 9/2009 | Georgiou et al. | |
| 2010/0197944 A1 | 8/2010 | Palle et al. | |
| 2010/0303893 A1 | 12/2010 | Luo et al. | |
| 2011/0111403 A1 | 5/2011 | Petrauskene et al. | |
| 2011/0301189 A1 | 12/2011 | Khattar et al. | |
| 2012/0015049 A1 | 1/2012 | Zhang | |
| 2012/0148559 A1 | 6/2012 | Georgiou et al. | |
| 2013/0052179 A1 | 2/2013 | Huang et al. | |
| 2014/0348814 A1 | 11/2014 | Almassy et al. | |
| 2015/0132278 A1 | 5/2015 | Bomalaski et al. | |
| 2015/0231272 A1 | 8/2015 | Bomalaski et al. | |
| 2016/0074487 A1 | 3/2016 | Showalter et al. | |
| 2017/0000862 A1* | 1/2017 | Wu | A61K 45/06 |

FOREIGN PATENT DOCUMENTS

| | | |
|---|---|---|
| EP | 1987838 B1 | 1/2016 |
| JP | 2001-524836 | 12/2001 |
| JP | 2006-515281 | 5/2006 |
| JP | 2009-523433 | 6/2006 |
| KR | 10-2004-0004449 | 1/2004 |
| WO | WO 98/51784 A1 | 11/1998 |
| WO | WO 01/83774 A2 | 11/2001 |
| WO | WO 02/44360 A2 | 6/2002 |
| WO | WO 2004/046309 A2 | 6/2004 |
| WO | WO 2013/151568 A1 | 10/2013 |
| WO | WO 2014/151982 A2 | 9/2014 |
| WO | WO 2015/143006 A1 | 9/2015 |
| WO | WO 2016/044376 A1 | 3/2016 |

OTHER PUBLICATIONS

Das et al. 2004; Crystal structures of arginine deiminase with covalent reaction intermediates: implications for catalytic mechanism. Structure. 12: 657-667.*
Fenske et al. 1976; Role of arginine deiminase in growth of Mycoplasma hominis. Journal of Bacteriology 126(1): 501-510.*
Extended European Search Report for European Application No. 14769340.2, mailed Jun. 16, 2016, 9 pages.
Office Action for U.S. Appl. No. 14/214,040, mailed Dec. 1, 2015, 21 pages.
Office Action for U.S. Appl. No. 14/214,040, mailed May 16, 2016, 17 pages.
International Search Report and Written Opinion for International Application No. PCT/US2012/039979, mailed Nov. 5, 2012, 12 pages.
International Preliminary Report on Patentability for International Application No. PCT/US2012/039979, dated Oct. 7, 2014, 8 pages.
International Search Report and Written Opinion for International Application No. PCT/US2015/021189, mailed Jun. 25, 2015, 9 pages.
International Preliminary Report on Patentability for International Application No. PCT/US2015/021189, mailed Sep. 20, 2016, 6 pages.
International Search Report and Written Opinion for International Application No. PCT/US2014/026766, mailed Oct. 24, 2014, 14 pages.
International Preliminary Report on Patentability for International Application No. PCT/US2014/026766, mailed Sep. 15, 2015, 9 pages.
International Search Report and Written Opinion for International Application No. PCT/US2015/050354, mailed Dec. 18, 2015, 7 pages.

(Continued)

*Primary Examiner* — Karen Cochrane Carlson
(74) *Attorney, Agent, or Firm* — Cooley LLP

(57) ABSTRACT

The present invention relates generally to isolated to arginine deiminase (ADI) proteins that have reduced cross-reactivity with anti-ADI-PEG 20 antibodies as compared to ADI-PEG 20, but which can have functional characteristics comparable to or better than ADI-PEG 20, compositions comprising the ADI proteins, and related methods of treating arginine-dependent diseases or related diseases such as cancer.

27 Claims, 6 Drawing Sheets

(56) References Cited

OTHER PUBLICATIONS

Ascierto, P. A. et al., "Pegylated Arginine Deiminase Treatment of Patients with Metastitic Melanoma: Results from Phase I and II Studies," Journal of Clinical Oncology, 23(30):7660-7668 and Erratum p. 4047 (2005).
Avramis, V. I. et al., "Pharmacokinetic/Pharmacodynamic Relationships of Asparaginase Formulations," Clin Pharmacokinet, 44(4):367-393 (2005).
Bi, D. et al., Isolation and identification of mycoplasmas from pigeons, Chinese Journal of Animal Poultry and Infectious Diseases, 19(6):1-5 (1997) [and English translation].
Bowles, T. et al., "Pancreatic Cancer Cell Lines Deficient in Argininosuccinate Synthetase are Sensitive to Arginine Deprivation by Arginine Deiminase," Int. J. Cancer, 128(8):1950-1955 (2008).
Cantor et al., "Therapeutic enzyme deimmunization by combinatorial T-cell epitope removal using neutral drift." Proc Natl Acad Sci USA, Jan. 5, 2011, vol. 108, No. 4, pp. 1272-1277.
Chen, N. et al., "Autophagy and tumorigenesis," FEBS Letters 584:1427-1435 (2010).
Das et al., "Crystal structures of arginine deiminase with covalent reaction intermediates implications for catalytic mechanism." Structure, Apr. 2004, vol. 12, No. 4, pp. 657-667.
Daylami, R. et al., "Abstract 4847: Arginine Deprivation by PEG-ADI Induces Autophagic Cell Death and Enhances the Tumor Suppression Effect of Gemcitabine in Pancreatic Cancer," Cancer Research, 70:4847 (2010).
Delage, B. et al., "Abstract 4445: Pegylated arginine deiminase induces mitochondrial apoptosis and synergizes with cisplatin in ASS1-negative malignant pleural mesothelioma," In: Proceedings of the 101st Annual Meeting of the American Association for Cancer Research, Apr. 17-21, 2010, Washington, DC, Philadelphia, PA: AACR; Cancer Research, 70(8 Suppl):Abstract nr 4445 (2010), 2 pages.
Delage, B. et al., "Arginine Deprivation and Argininosuccinate Synthetase Expression in the Treatment of Cancer," International Journal of Cancer, 126:2762-2772 (2010).
Ensor, C. M. et al., "Pegylated Arginine Deiminase (ADI-SS PEG20,000 mw) Inhibits Human Melanomas and Hepatocellular Carcinomas in Vitro and in Vivo," Cancer Research, 62(19):5443-5450 (2002).
Feun, L. et al., "Arginine Deprivation as a Targeted Therapy for Cancer," Current Pharmaceutical Design, 14:1049-1057 (2008).
Feun, L. et al., "Pegylated arginine deiminase: a novel anticancer enzyme agent," Expert Opin. Investig. Drugs., 15(7):815-822 (2006).
Fu, C. H. et al., "PEG-asparaginase," Expert Opinion Pharmacotherapy, 8(12):1977-1984 (2007).
Gallego, Pablo, et al. "Structural characterization of the enzymes composing the arginine deiminase pathway in Mycoplasma penetrans." PloS One (2012); 7.10: e47886.
Glazer, E. et al., "Phase II Study of Pegylated Arginine Deiminase for Nonresectable and Metastatic Hepatocellular Carcinoma," Journal of Clinical Oncology, 28(13):2220-2226 (2010).
Gong, H. et al., "Arginine Deiminase Inhibits Proliferation of Human Leukemia Cells More Potently than Asparaginase by Inducing Cell Cycle Arrest and Apoptosis," Leukemia, 14:826-829 (2000).
Guo, Zisheng, et al. "Genome sequence of Mycoplasma columbinum strain SF7." Genome Announcements (2013); 1.2: e00157-13.
Guo, Zisheng, et al. Mycoplasma columbinum Strain SF7 genome translation from Guo et al, Genome Announcements (2013); 1.2: e00157-13, 64 pages.
Guven, K. et al., "Cisplatin and Carboplatin Combination as Second-Lind Chemotherapy in Dacarbazine-Resistant Melanoma Patients," Melanoma Research, 11:411-415 (2001).
He, W. et al., "Abstract 4703: Lack of Expression of Argininosuccinate Synthetase in Human Cancer Tissue: A Biomarker for Sensitivity to Arginine Depetion with Pegylated Arginine Deiminase," Cancer Research, 70, Proceedings: AACR 101st Annual Meeting 2010—Apr. 17-21, 2010, 2 pages.
Henningham et al., "Structure-informed design of an enzymatically inactive vaccine component for group A *Streptococcus*." MBio, Jul./Aug. 2013, vol. 4, No. 4, pii: e00509-13.
Hernandez, C. et al., "Pegylated Arginase I: A Potential Therapeutic Approach in T-ALL," Blood, 115(25):5214-5221 (2010).
Holtsberg, F. W. et al., "Poly(ethylene glycol) (PEG) Conjugated Arginine Deiminase: Effects of PEG Formulations on its Pharmacological Properties," Journal of Controlled Release, 80:259-271 (2002).
International Pharmaceutical Excipients Council Japan (ed.), Iyakutenkabutsu Jiten [Pharmaceutical Excipient Dictionary] 2007, Yakuji Nippo Limited, Jul. 25, 2007, p. 220-221.
Izzo, F. et al., "Pegylated Arginine Deiminase Treatment of Patients With Unresectable Hepatocellular Carcinoma: Results From Phase I/II Studies," Journal of Clinical Oncology, 22(10):1815-1822 (2004).
Kelly, M., et al., Abstract 4519: Small Cell Lung Cancers Lack Expression of Argininosuccinate Synthase (ASS) and are sensitive to Arginine Deprivation Using Arginine Deiminase-PEG20 (ADI-PEG20), Cancer Research, 70, AACR 101st Annual Meeting, Apr. 17-21, 2010, 2 pages.
Kelly, M. P. et al., "Arginine Deiminase PEG20 Inhibits Growth of Small Cell Lung Cancers Lacking Expression of Argininosuccinate Synthetase," British Journal of Cancer, 106(2):324-332 (2012).
Kim, R. H. et al., "ADI, Autophagy and Apoptosis: Metabolic Stress as a Therapeutic Option for Prostate Cancer," Autophagy, 5(4):567-568 (2009).
Kim, R. H. et al., "Arginine Deiminase as a Novel Therapy for Prostate Cancer Induces Autophagy and Caspase-Independent Apoptosis," Cancer Research, 69(2):700-708 (2009).
Komada, Y., et al., "Apoptoptic Cell Death of Human T Lymphoblastoid Cells Induced by Arginine Deimanse," International Journal of Hematology, 65:129-141 (1997).
Kung, C., et al., "Autophagy in Tumor Suppression and Cancer Therapy," Critical Reviews in Eukaryotic Gene Expression, vol. 21, No. 1, 2011, pp. 71-100.
NCBI Acc# 4E4J_A from Gallego et al, 2012. Alignment with Seq ID No. 8, 2 pages.
Ni, Y. et al., "Arginine Deiminase, a Potential Anti-Tumor Drug," Cancer Letters 261:1-11 (2008).
Ni et al., "Rapid evolution of arginine deiminase for improved anti-tumor activity," Appl Microbiol Biotechnol., Jan. 11, 2011, vol. 90, No. 1, pp. 193-201.
Noh, E-J. et al., "Arginine Deiminase Enhances Dexamethasone-Induced Cytotoxicity in Human T-Lymphoblastic Leukemia CCRF-CEM Cells," Int. J. Cancer, 112:502-508 (2004).
Ohno, T. et al., "Argininosuccinate Synthetase Gene Expression in Leukemias: Potential Diagnostic Marker for Blastic Crisis of Chronic Myelocytic Leukemia," Leukemia Research, 16(5):475-483 (1992).
Poteete and Hardy, "Genetic Analysis of Bacteriophage T4 Lysozyme Structure and Function." Journal of Bacteriology, 176(22): 6783-6788 (1994).
Rodriguez, C. O. et al., "Abstract 4848: Pegylated arginine deiminase induces autophagy in canine melanoma and canine osteosarcoma," In: Proceedings of the 101st Annual Meeting of the American Association for Cancer Research, Apr. 17-21, 2010, Washington, DC, Philadelphia, PA: AACR Cancer Research, 70(8 Suppl.):Abstract nr 4848 (2010), 2 pages.
Savaraj, N., et al., "Arginine Deprivation, Autophagy, Apoptosis (AAA) for the Treatment of Melanoma," Current Molecular Medicine 2010, vol. 10, pp. 405-412.
Shen, L., et al., "Drug Evaluation: ADI-PEG-20—a PEGylated Arginine Deiminase for Arginine-Auxotrophic Cancers," Current Opinon in Molecular Therapeutics, 2006, vol. 8, No. 3, pp. 240-248.
Singapore Application No. 11201507354Q, Search Report and Written Opinion mailed Oct. 10, 2016, 16 pages.
Sugimura, K., et al., "Tumor Growth Inhibitory Activity of a Lymphocyte Blastogenesis Inhibitory Factor," Cancer Research, 50, Jan. 15, 1990, pp. 345-349.

(56) References Cited

OTHER PUBLICATIONS

Sugimura, K., et al., "Elevated Argininosuccinate Synthetase Activity in Adult T Leukemia Cell Lines," Leukemia Research, vol. 14, No. 10, 1990, pp. 931-934.
Sugimura et al., "Polymorphism in genes for the enzyme arginine deiminase among *Mycoplasma* species." Infect. Immun. Jan. 1, 1993, vol. 61, No. 1, pp. 329-331.
Szlosarek, P., et al., "Abstract 4067: Pegylated Arginine Deiminase (ADI-PEG20) as a Potential Novel Therapy for Argininosuccinate Synthetase-Deficient Acute Myeloid Leukemia," Proceedings of the 102nd Annual Meeting of the American Associate for Cancer Research, Apr. 2-6, 2011, vol. 71, No. 8 (Supp), 2 pages.
Szlosarek, P., et al., "In Vivo Loss of Expression of Argininosuccinate Synthetase in Malignant Pleural Mesothelioma is a Biomarker for Susceptibility to Arginine Depletion," Cancer Therapy: Preclinical, Clin Cancer Research, vol. 12, No. 23. Dec. 1, 2006, pp. 7123-7131.
Szlosarek, P., et al., "Effect of Inactivation of Argininosuccinate Synthetase on Sensitivity of Lymphomas to Caspase-Dependent Apoptosis Following Treatment with Arginine Deiminase," Journal of Clinical Oncology, vol. 28. No. 15 (May 20 Supp), 2010, 2 pages.
Taiwanese Patent Application No. 101119399, Search Report dated Nov. 22, 2016, 1 page.
USPTO in house BLAST alignment ADI-PEG 20 (the variant of Seq ID No. 1 herein consisting of the substitutions K112E and P21OS) alignment with Seq ID No. 8. Performed May 10, 2016.
Wang, M. et al., "Engineering an arginine catabolizing bioconjugate: Biochemical and pharmacological characterization of PEGylated derivatives of arginine deiminase from mycoplasma arthritidis," Bioconjugate Chem., 17:1447-1459 (2006).
Weickmann and Fahrney. "Arginine deiminase from Mycoplasma arthritidis. Evidence for multiple forms." Journal of Biological Chemistry (1977); 252.8: 2615-2620.
Yang, T., et al., "A Randomised Phase II Study of Pegylated Arginine Deiminase (ADI-PEG 20) in Asian Advanced Hepatocellular Carcinoma Patients," British Journal of Cancer, vol. 103, 2010, pp. 954-960.
You, M. et al., "Abstract 61: Enhancing Arginine Deprivation Therapy in Melanoma by Combining with Cisplatin," In: Proceedings of the 101st Annual Meeting of the American Association for Cancer Research, Apr. 17-21, 2010, Washington, DC, Philadelphia, PA: AACR Cancer Research; 70(8 Suppl.):Abstract nr 61, (2010), 2 pages.
You, M. et al., "Abstract #3418: Arginine Deprivation and Soluble TRAIL Strikingly Enhance Death in Argininosuccinate Synthetase Negative Melanoma Cells," Proc. Am. Assoc. Cancer Research; Apr. 18-22, 2009, 2 pages.
You, M., et al., "Abstract 4096: TRAIL Enhances Cytotoxicity of Arginine Depletion Therapy in Argininosuccinate Synthetase-Negative Melanoma Cells Through Interruption of Autophagy Via Activation of Caspases," Proceedings of the 102nd Annual Meeting of the American Association for Cancer Research; Apr. 2-6, 2011, Cancer Research 2011, vol. 71, No. 8 (Supp), 2 pages.
You, M., et al., "The Combination of ADI-PEG20 and TRAIL Effectively Increases Cell Death in Melanoma Cell Lines," Biochemical and Biophysical Research Communications, 394:760-766 (2010).
Zamora, R. et al., "Inducible Nitric Oxide Synthase and Inflammatory Diseases," Molecular Medicine, 6(5):347-360 (2000).
Zeidan, A. et al., "Pegasparaginase: where do we stand?", Expert Opinion Biol. Ther, 9(1):111-119 (2009).
UniProtKB Submission F9UJU2_9MOLU, Arginine deiminase; Mycoplasma columbinum SF7 (Jan. 9, 2013). Retrieved from the Internet Jun. 22, 2014: <http://www.uniprot.org/uniprot/F9UJU2.txt?version=6>, 1 page.
UniProtKB/TrEMBL Submission A7LHN6_9MOLU (Jan. 9, 2013) Retrieved from the Internet Jun. 22, 2014: <http://www.uniprot.org/uniprot/A7LHN6.txt?version=28>, 1 page.
Venugopal, V. et al., "Histidine-dependent activation of arginine deiminase in clostridium sporogenes: Kinetic evidence on in vivo allosteric interactions," FEBS Letters, 51(1):246-248 (1975).
Zlotogorski, A. "Distribution of skin surface pH on the forehead and cheek of adults." Archives of Dermatological Research (1987); 279.6: 398-401.
Office Action for U.S. Appl. No. 14/214,040, mailed Oct. 18, 2016, 19 pages.
International Preliminary Report on Patentability for International Application No. PCT/US2015/050354, mailed Mar. 21, 2017, 6 pages.
Baxalta US Inc., Westlake Village, CA, Oncaspar, U.S. Food and Drug Administration Product Label, 8 pages, (Revised 2015).
De Angelis, M., et al., "Arginine Catabolism by Sourdough Lactic Acid Bacteria: Purification and Characterization of the Arginine Deiminase Pathway Enzymes from Lactobacillus sanfranciscensis CB 1." Applied and Environmental Microbiology, vol. 68, No. 12, Dec. 2002, pp. 6193-6201.
Kim, J., et al., "Expression, purification, and characterization of arginine deiminase from *Lactococcus lactis* ssp. *lactis* ATCC7962 in *Escherichia coli* BL21," Protein Expr. Purif. (2007), doi:10.1016/j.pep.2006.12.002, 7 pages.
Singapore Application No. 201307953-8, Search Report and Written Opinion mailed Jan. 26, 2016, 9 pages.

* cited by examiner

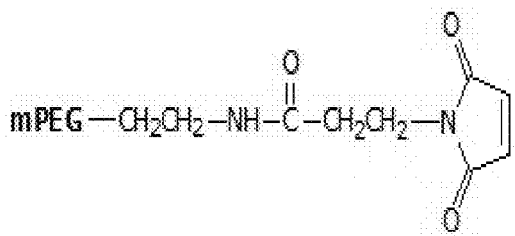

| ITEM CODE | ITEM NUMBER | ITEM DESCRIPTION |
|---|---|---|
| A3073-1 | M-MAL-2000,1g | Methoxy PEG Maleimide, MW 2000 |
| A3073-10 | M-MAL-2000,10g | Methoxy PEG Maleimide, MW 2000 |
| A3014-1 | M-MAL-5000,1g | Methoxy PEG Maleimide, MW 5000 |
| A3014-10 | M-MAL-5000,10g | Methoxy PEG Maleimide, MW 5000 |
| A3045-1 | M-MAL-10K,1g | Methoxy PEG Maleimide, MW 10000 |
| A3045-10 | M-MAL-10K,10g | Methoxy PEG Maleimide, MW 10000 |
| A3002-1 | M-MAL-20K,1g | Methoxy PEG Maleimide, MW 20000 |
| A3002-10 | M-MAL-20K,10g | Methoxy PEG Maleimide, MW 20000 |
| A3046-1 | M-MAL-30K,1g | Methoxy PEG Maleimide, MW 30000 |
| A3046-10 | M-MAL-30K,10g | Methoxy PEG Maleimide, MW 30000 |
| A3042-1 | M-MAL-40K,1g | Methoxy PEG Maleimide, MW 40000 |
| A3042-10 | M-MAL-40K,10g | Methoxy PEG Maleimide, MW 40000 |

FIG. 1A

SUNBRIGHT® MA Series (Maleimide PEGs)

C2 Type

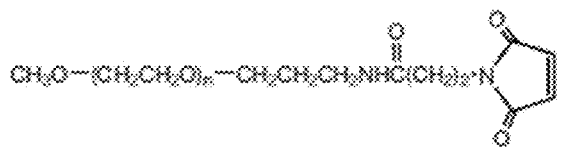

| Product Name | MW |
|---|---|
| SUNBRIGHT ME-020MA | 2,000 |
| SUNBRIGHT ME-050MA | 5,000 |
| SUNBRIGHT ME-100MA New | 10,000 |
| SUNBRIGHT ME-120MA | 12,000 |
| SUNBRIGHT ME-200MA | 20,000 |
| SUNBRIGHT ME-300MA | 30,000 |
| SUNBRIGHT ME-400MA | 40,000 |

C5 Type

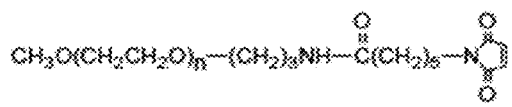

| Product Name | Functional Group | MW |
|---|---|---|
| SUNBRIGHT ME-050MA3 New | | 5,000 |
| SUNBRIGHT ME-120MA3 New | Maleimide | 12,000 |
| SUNBRIGHT ME-200MA3 New | -(CH₂)₃-NHCO-(CH₂)₅-Maleimide | 20,000 |
| SUNBRIGHT ME-400MA3 New | | 40,000 |

SUNBRIGHT® IA series (Iodoacetamide-PEG)

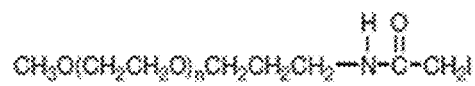

| Product Name | MW |
|---|---|
| SUNBRIGHT ME-200IA | 20,000 |
| SUNBRIGHT ME-300IA | 30,000 |
| SUNBRIGHT ME-400IA | 40,000 |

FIG. 1B

SEQUENCE LISTING

<160> NUMBER OF SEQ ID NOS: 28

<210> SEQ ID NO 1
<211> LENGTH: 409
<212> TYPE: PRT
<213> ORGANISM: Mycoplasma hominis

<400> SEQUENCE: 1

```
Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
                35                  40                  45

Leu Glu Ser His Asp Ala Arg Lys Glu His Gln Ser Phe Val Lys Ile
        50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95

Thr Phe Leu Glu Glu Thr Val Pro Val Leu Thr Glu Ala Asn Lys Lys
            100                 105                 110

Ala Val Arg Ala Phe Leu Leu Ser Lys Pro Thr His Glu Met Val Glu
                115                 120                 125

Phe Met Met Ser Gly Ile Thr Lys Tyr Glu Leu Gly Val Glu Ser Glu
130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
        195                 200                 205

Met Pro Ile Glu Gly Gly Asp Val Phe Ile Tyr Asn Asn Glu Thr Leu
210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
    290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
        355                 360                 365
```

```
Thr Asn Ala Ala Leu Lys Ala Ala Gly Ile Thr Val Leu Pro Phe His
    370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 2
<211> LENGTH: 410
<212> TYPE: PRT
<213> ORGANISM: Mycoplasma salivarium

<400> SEQUENCE: 2

Met Ser Val Phe Ser Ser Lys Phe Asn Gly Ile His Val Tyr Ser Glu
1               5                   10                  15

Ile Gly Glu Leu Glu Thr Val Leu Val His Pro Gly Lys Glu Ile
            20                  25                  30

Asp Tyr Ile Thr Pro Ser Arg Leu Asp Glu Leu Leu Phe Ser Ala Ile
            35                  40                  45

Leu Glu Ser His Asp Ala Arg Lys Glu His Gln Glu Phe Val Ala Thr
50                  55                  60

Leu Lys Lys Glu Lys Ile Asn Val Val Glu Leu Thr Asp Leu Val Thr
65                  70                  75                  80

Glu Thr Tyr Asp Leu Val Asp Gln Lys Thr Lys Asp Lys Leu Ile Asp
                85                  90                  95

Glu Phe Leu Glu Asp Ser Glu Pro Val Leu Thr Ala Glu Leu Lys Ala
            100                 105                 110

Thr Val Lys Lys Phe Leu Lys Ser Phe Lys Glu Thr Arg Lys Leu Ile
            115                 120                 125

Glu Val Met Met Ala Gly Ile Thr Lys Tyr Asp Leu Gly Ile Lys Ala
        130                 135                 140

Asp Arg Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Asn
            180                 185                 190

Asn His Pro Lys Leu Val Lys Thr Pro Trp Tyr Tyr Asp Pro Ala Met
        195                 200                 205

Lys Met Ser Ile Glu Gly Gly Asp Val Phe Ile Tyr Asn Asn Asp Thr
210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Ile Phe Lys Phe Trp Asp Tyr Asp Leu Val Asn Gly Gly Ala
        290                 295                 300

Asn Pro Gln Pro Lys Asp Asn Gly Leu Pro Leu Asp Lys Leu Leu Lys
305                 310                 315                 320

Ser Ile Ile Gly Lys Glu Pro Val Leu Ile Pro Ile Ala Gly His His
                325                 330                 335
```

```
Ala Thr Glu Ile Glu Val Ala Arg Glu Thr His Phe Asp Gly Thr Asn
            340                 345                 350

Tyr Leu Ala Ile Arg Pro Gly Val Ile Gly Tyr Ala Arg Asn Glu
        355                 360                 365

Lys Thr Asn Glu Ala Leu Lys Asp Ala Gly Ile Thr Val Leu Pro Phe
370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 3
<211> LENGTH: 411
<212> TYPE: PRT
<213> ORGANISM: Mycoplasma spumans

<400> SEQUENCE: 3

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Phe Ser Ala Ile
        35                  40                  45

Leu Glu Ser His Asp Ala Arg Lys Glu His Lys Gly Phe Val Ala Glu
50                  55                  60

Leu Lys Lys Gln Asn Val Asn Val Ile Glu Leu Thr Asp Leu Val Ala
65                  70                  75                  80

Glu Thr Tyr Glu Leu Ala Ser Lys Glu Ala Gln Ala Lys Leu Ile Glu
                85                  90                  95

Asp Phe Ile Glu Asp Ser Glu Pro Val Leu Asn Ala Glu Glu Ala Gln
            100                 105                 110

Ala Val Arg Lys Phe Leu Ser Glu Arg Lys Ser Thr Arg Glu Met Val
            115                 120                 125

Glu Tyr Met Met Ser Gly Leu Thr Lys Tyr Glu Leu Gly Leu Glu Ser
130                 135                 140

Ala Asp Arg Glu Leu Ile Val Asp Pro Met Pro Asn Leu Tyr Phe Thr
145                 150                 155                 160

Arg Asp Pro Phe Ala Ser Val Gly Asn Gly Val Thr Ile His Tyr Met
                165                 170                 175

Lys Tyr Lys Val Arg Gln Arg Glu Thr Leu Phe Ala Lys Phe Val Phe
            180                 185                 190

Ser Asn His Pro Lys Leu Val Asn Thr Pro Arg Tyr Tyr Asp Pro Ser
        195                 200                 205

Met Lys Leu Pro Ile Glu Gly Gly Asp Val Phe Ile Tyr Asn Asn Glu
210                 215                 220

Thr Leu Val Val Gly Cys Ser Glu Arg Thr Glu Leu Glu Thr Ile Thr
225                 230                 235                 240

Leu Leu Ala Lys Asn Ile Lys Ala Asn Lys Glu Val Glu Phe Lys Arg
                245                 250                 255

Ile Val Ala Ile Asn Val Pro Lys Trp Thr Asn Leu Met His Leu Asp
            260                 265                 270

Thr Trp Leu Thr Met Leu Asp Lys Asp Lys Phe Leu Tyr Ser Pro Ile
        275                 280                 285

Ala Asn Asp Val Phe Lys Phe Trp Asp Tyr Asp Leu Val Asn Gly Gly
```

```
                290                 295                 300
Glu Glu Pro Gln Pro Val Glu Asn Gly Leu Pro Leu Glu Glu Leu Leu
305                 310                 315                 320

Ala Ser Ile Ile Asn Lys Lys Pro Thr Leu Ile Pro Ile Ala Gly Glu
                325                 330                 335

Gly Ala Thr His Ile Asp Val Glu Arg Glu Thr His Phe Asp Gly Thr
                340                 345                 350

Asn Tyr Leu Ala Ile Ala Pro Ala Leu Ile Ile Gly Tyr Ser Arg Asn
                355                 360                 365

Glu Lys Thr Asn Ala Ala Leu Glu Lys Ala Gly Ile Thr Val Leu Pro
                370                 375                 380

Phe His Gly Asn Gln Leu Ser Leu Gly Met Gly Asn Ala Arg Cys Met
385                 390                 395                 400

Ser Met Pro Leu Ser Arg Lys Asp Val Lys Trp
                405                 410

<210> SEQ ID NO 4
<211> LENGTH: 410
<212> TYPE: PRT
<213> ORGANISM: Mycoplasma auris

<400> SEQUENCE: 4

Met Ser Val Phe Asp Ser Lys Phe Lys Gly Ile His Val Tyr Ser Glu
1               5                   10                  15

Ile Gly Glu Leu Glu Thr Val Leu Val His Glu Pro Gly Arg Glu Ile
                20                  25                  30

Asp Tyr Ile Thr Pro Lys Arg Leu Asp Glu Leu Leu Phe Ser Ala Ile
                35                  40                  45

Leu Glu Ser His Glu Ala Arg Lys Glu His Lys Gln Phe Val Ala Glu
                50                  55                  60

Leu Lys Ala Asn Asp Ile Asn Val Val Glu Leu Thr Asp Leu Val Ala
65                  70                  75                  80

Glu Thr Tyr Asp Leu Val Ser Gln Glu Leu Lys Asp Lys Leu Ile Glu
                85                  90                  95

Glu Phe Leu Asp Asp Ser Tyr Pro Val Leu Thr Glu Glu His Lys Lys
                100                 105                 110

Ala Val Arg Ser Phe Leu Lys Ser Arg Ser Ser Thr Arg Glu Leu Ile
                115                 120                 125

Glu Tyr Met Met Ala Gly Ile Thr Lys Tyr Asp Leu Gly Ile Glu Ala
                130                 135                 140

Glu Gly Asp Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Asp
                180                 185                 190

Asn His Pro Lys Leu Val Asn Thr Pro Arg Tyr Tyr Asp Pro Ser Leu
                195                 200                 205

Lys Leu Ser Ile Glu Gly Gly Asp Val Phe Ile Tyr Asn Asn Asp Thr
                210                 215                 220

Leu Val Met Gly Val Ser Glu Arg Thr Asp Leu Glu Thr Val Thr Leu
225                 230                 235                 240

Leu Ala Lys Asn Ile Val Ala Asn Lys Glu Cys Glu Phe Lys Arg Ile
                245                 250                 255
```

```
Val Ala Ile Asn Val Pro His Trp Thr Asn Leu Met His Leu Asp Thr
                260                 265                 270

Trp Leu Thr Met Leu Asp Lys Asp Lys Phe Leu Tyr Ser Pro Ile Ala
            275                 280                 285

Asn Asp Tyr Phe Lys Phe Trp Asp Tyr Asp Leu Val Asn Gly Gly Ala
        290                 295                 300

Glu Pro Gln Pro Val Val Asn Glu Leu Pro Leu Asp Lys Leu Leu Glu
305                 310                 315                 320

Ser Ile Ile His Lys Lys Pro Ile Leu Ile Pro Ile Ala Gly Glu Gly
                325                 330                 335

Ala Ser Gln Ile Asp Leu Glu Arg Glu Thr His Phe Asp Gly Thr Asn
            340                 345                 350

Tyr Leu Val Leu Arg Pro Gly Val Val Gly Tyr Ala Arg Asn Glu
        355                 360                 365

Lys Thr Asn Ala Ala Leu Glu Ala Val Gly Ile Lys Val Leu Pro Phe
        370                 375                 380

Tyr Gly Asn Gln Leu Ser Leu Gly Met Gly Asn Ser Arg Cys Met Ser
385                 390                 395                 400

Met Pro Leu Ser Arg Lys Asp Val Lys Trp
                405                 410

<210> SEQ ID NO 5
<211> LENGTH: 410
<212> TYPE: PRT
<213> ORGANISM: Mycoplasma hyosynoviae

<400> SEQUENCE: 5

Met Ser Val Phe Asn Ser Lys Phe Lys Gly Ile His Val Tyr Ser Glu
1               5                   10                  15

Ile

```
Leu Val Val Gly Val Ser Glu Arg Thr Asp Leu Asp Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Ile Phe Lys Phe Trp Asp Tyr Asp Leu Val Asn Gly Gly Ser
    290                 295                 300

Glu Pro Gln Pro Lys Asp Asn Gly Leu Pro Leu Glu Lys Leu Leu Glu
305                 310                 315                 320

Ser Ile Ile Gly Lys Lys Pro Val Leu Ile Pro Ile Ala Gly Cys Cys
                325                 330                 335

Ala Ser Asp Ile Glu Ile Ala Arg Glu Thr His Phe Asp Gly Thr Asn
            340                 345                 350

Tyr Leu Ala Ile Lys Pro Gly Val Val Ile Gly Tyr Ala Arg Asn Glu
        355                 360                 365

Lys Thr Asn Lys Ala Leu Glu Lys Ala Gly Ile Lys Val Leu Pro Phe
    370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 6
<211> LENGTH: 409
<212> TYPE: PRT
<213> ORGANISM: Mycoplasma cloacale

<400> SEQUENCE: 6

Met Ser Val Phe Asp Lys Arg Phe Lys Gly Ile His Val Tyr Ser Glu
1               5                   10                  15

Ile Gly Glu Leu Gln Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Glu Phe Val Lys Ile
    50                  55                  60

Leu Glu Ser Gln Gly Ile Asn Val Val Glu Leu Thr Asp Leu Ile Ala
65                  70                  75                  80

Glu Thr Tyr Glu Leu Ala Ser Glu Glu Ala Lys Asp Asn Leu Ile Glu
                85                  90                  95

Glu Phe Leu Asp Glu Ser Glu Pro Val Leu Ser Glu Glu His Arg Ile
            100                 105                 110

Leu Val Arg Asn Phe Leu Lys Gly Ile Thr Lys Thr Lys Glu Leu Val
        115                 120                 125

Lys Met Met Met Ala Gly Ile Thr Lys Tyr Asp Leu Gly Ile Glu Ala
    130                 135                 140

Asp Arg Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Glu
```

```
                    180                 185                 190
Asn His Pro Lys Leu Val Ser Thr Pro Ile Tyr Tyr His Pro Ser Gln
                195                 200                 205

Gly Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Glu Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asn Lys Phe Leu Tyr Ser Pro Ile Ala
        275                 280                 285

Asn Asp Val Phe Lys Phe Trp Asp Tyr Asp Leu Val Asn Gly Gly Asp
    290                 295                 300

Glu Pro Gln Pro Val Asp Asn Gly Leu Pro Leu Asn Glu Leu Leu Ala
305                 310                 315                 320

Ser Ile Ile Gly Glu Glu Pro Val Leu Val Pro Ile Ala Gly Glu Gly
                325                 330                 335

Ala Ser Lys Met Asp Ile Glu Arg Glu Thr His Phe Asp Gly Thr Asn
            340                 345                 350

Tyr Leu Ala Ile Ala Pro Gly Val Val Gly Tyr Ser Arg Asn Glu
        355                 360                 365

Lys Thr Asn Ala Ala Leu Glu Lys Ala Gly Ile Lys Val Leu Pro Phe
    370                 375                 380

Lys Gly His Gln Leu Ser Leu Gly Met Gly Asn Ala Arg Cys Met Ser
385                 390                 395                 400

Met Pro Leu Tyr Arg Lys Asp Val Lys
                405

<210> SEQ ID NO 7
<211> LENGTH: 412
<212> TYPE: PRT
<213> ORGANISM: Mycoplasma alkalescens

<400> SEQUENCE: 7

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly His Glu Ile
            20                  25                  30

Asp Tyr Ile Thr Pro Ser Arg Leu Asp Glu Leu Leu Phe Ser Ala Met
        35                  40                  45

Leu Glu Ser His Asp Ala Arg Lys Glu His Lys Gln Phe Val Ala Glu
    50                  55                  60

Leu Lys Ala Asn Asn Val Asn Val Ile Glu Leu Thr Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu Asn Lys Ile
            100                 105                 110

Ala Val Arg Asp Phe Leu Lys Ser Arg Lys Thr Thr Arg Glu Leu Ile
        115                 120                 125

Glu Val Met Met Ala Gly Ile Thr Lys Tyr Asp Leu Gly Ile Lys Asn
    130                 135                 140
```

```
Cys Lys Cys Gln Asp Leu Val Val Asp Pro Met Pro Asn Leu Tyr Phe
145                 150                 155                 160

Thr Arg Asp Pro Phe Ala Ser Val Gly Asn Gly Ile Thr Ile His Tyr
            165                 170                 175

Met Arg Tyr Lys Val Arg Gln Arg Glu Thr Leu Phe Ser Arg Phe Ile
        180                 185                 190

Phe Ala Asn His Pro Lys Leu Val Asn Thr Pro Ile Tyr Tyr His Pro
    195                 200                 205

Ser Leu Lys Leu Ser Ile Glu Gly Asp Val Phe Ile Tyr Asn Asn
210                 215                 220

Asp Thr Leu Val Val Gly Val Ser Glu Arg Thr Asp Leu Glu Thr Ile
225                 230                 235                 240

Thr Leu Leu Ala Lys Asn Ile Val Ala Asn Lys Glu Cys Glu Phe Lys
                245                 250                 255

Arg Ile Val Ala Ile Asn Val Pro Lys Trp Thr Asn Leu Met His Leu
            260                 265                 270

Asp Thr Trp Leu Thr Met Leu Asp Lys Asp Lys Phe Leu Tyr Ser Pro
        275                 280                 285

Ile Ala Asn Asp Val Phe Lys Phe Trp Asp Tyr Asp Leu Val Asn Gly
    290                 295                 300

Gly Ala Glu Pro Lys Pro Val Glu Asn Gly Ser Ser Leu Glu Ala Ile
305                 310                 315                 320

Leu Glu Ser Ile Ile His Lys Lys Pro Ile Leu Ile Pro Ile Gly Gly
                325                 330                 335

Asp Ser Ala Ser Gln Ile Glu Val Glu Arg Glu Thr His Phe Asp Gly
            340                 345                 350

Thr Asn Tyr Leu Ala Ile Arg Pro Gly Val Val Ile Gly Tyr Ser Arg
        355                 360                 365

Asn Val Lys Thr Asn Ala Ala Leu Glu Ala Ala Gly Ile Lys Val Ile
    370                 375                 380

Pro Phe His Gly Asn Gln Leu Ser Leu Gly Met Gly Asn Ala Arg Cys
385                 390                 395                 400

Met Ser Met Pro Leu Ser Arg Lys Asp Val Lys Trp
                405                 410

<210> SEQ ID NO 8
<211> LENGTH: 410
<212> TYPE: PRT
<213> ORGANISM: Mycoplasma orale

<400> SEQUENCE: 8

Met Ser Val Phe Ser Asp Lys Phe Asn Gly Ile His Val Tyr Ser Glu
1               5                   10                  15

Ile Gly Asp Leu Glu Ser Val Leu Val His Glu Pro Gly Lys Glu Ile
            20                  25                  30

Asp Tyr Ile Thr Pro Ala Arg Leu Asp Glu Leu Leu Phe Ser Ala Ile
        35                  40                  45

Leu Glu Ser Thr Asp Ala Arg Lys Glu His Lys Glu Phe Val Glu Ile
    50                  55                  60

Leu Lys Lys Gln Gly Ile Asn Val Glu Leu Val Asp Leu Val Val
65                  70                  75                  80

Glu Thr Tyr Asn Leu Val Asp Lys Lys Thr Gln Glu Lys Leu Leu Lys
                85                  90                  95

Asp Phe Leu Asp Asp Ser Glu Pro Val Leu Ser Pro Glu His Arg Lys
            100                 105                 110
```

```
Ala Val Glu Lys Phe Leu Lys Ser Leu Lys Ser Thr Lys Glu Leu Ile
            115                 120                 125

Gln Tyr Met Met Ala Gly Ile Thr Lys Tyr Asp Leu Gly Ile Lys Ala
        130                 135                 140

Asp Lys Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Lys Phe Ile Phe Thr
            180                 185                 190

Asn His Pro Lys Leu Val Lys Thr Pro Trp Tyr Tyr Asp Pro Ala Met
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Glu Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ser
    290                 295                 300

Asn Pro Glu Pro Val Val Asn Gly Leu Pro Leu Asp Lys Leu Leu Glu
305                 310                 315                 320

Ser Ile Ile Asn Lys Lys Pro Val Leu Ile Pro Ile Ala Gly Lys Gly
                325                 330                 335

Ala Thr Glu Ile Glu Thr Ala Val Glu Thr His Phe Asp Gly Thr Asn
            340                 345                 350

Tyr Leu Ala Ile Lys Pro Gly Val Val Val Gly Tyr Ser Arg Asn Val
        355                 360                 365

Lys Thr Asn Ala Ala Leu Glu Ala Asn Gly Ile Lys Val Leu Pro Phe
370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 9
<211> LENGTH: 401
<212> TYPE: PRT
<213> ORGANISM: Mycoplasma iners

<400> SEQUENCE: 9

Met Ser Lys Ile Asn Val Tyr Ser Glu Ile Gly Val Leu Lys Glu Val
1               5                   10                  15

Leu Val His Thr Pro Gly Asp Glu Ile Arg Arg Ile Ala Pro Ser Arg
            20                  25                  30

Leu Asp Glu Leu Leu Phe Ser Ala Ile Leu Glu Pro Ser Ala Ala Ile
        35                  40                  45

Gln Glu His Lys Ser Phe Leu Lys Ile Leu Gln Asp Arg Gly Ile Lys
    50                  55                  60

Thr Ile Gln Leu Ser Asp Leu Val Ala Glu Thr Tyr Lys His Tyr Ala
```

Ser Glu Ala Glu Lys Glu Ala Phe Ile Glu Lys Tyr Leu Asp Glu Ala
65                  70                  75                  80

Thr Pro Val Leu Ser Lys Asp Met Arg Ala Lys Val Lys Asn Tyr Ile
            85                  90                  95

Leu Ser Met Gln Gly Glu Pro Val Lys Met Val Arg Thr Met Met Ala
        100                 105                 110

Gly Val Ser Lys Gln Glu Leu Asn Val Glu Ser Glu Val Glu Leu Ile
    115                 120                 125

Val Asp Pro Met Pro Asn Leu Tyr Phe Thr Arg Asp Pro Phe Ala Ser
130                 135                 140

Ala Gly Asn Gly Ile Ser Leu Asn Asn Met Lys Tyr Val Val Arg Lys
145                 150                 155                 160

Arg Glu Thr Ile Phe Ala Glu Phe Ile Phe Ser Ile His Pro Glu Tyr
            165                 170                 175

Lys Lys Thr Pro His Trp Phe Asp Arg Leu Asp Asn Gly Ser Ile Glu
        180                 185                 190

Gly Gly Asp Val Phe Ile Tyr Asn Lys Asp Thr Leu Val Ile Gly Val
    195                 200                 205

Ser Glu Arg Thr Asn Lys Glu Ala Ile Ile Thr Ile Ala Lys His Ile
210                 215                 220

Gln Asp Asn Lys Glu Ala Gln Phe Lys Lys Ile Val Ala Ile Asn Val
225                 230                 235                 240

Pro Pro Met Pro Asn Leu Met His Leu Asp Thr Trp Leu Thr Met Val
            245                 250                 255

Asp Lys Asn Lys Phe Leu Tyr Ser Pro Asn Met Leu Ser Val Leu Lys
        260                 265                 270

Val Trp Glu Ile Asp Leu Ser Lys Pro Ile Glu Met Val Glu Thr Asn
    275                 280                 285

Lys Pro Leu Ala Glu Val Leu Glu Ser Ile Ile Gly Glu Lys Pro Ile
290                 295                 300

Leu Ile Pro Ile Ala Gly Lys Asp Ala Thr Gln Leu Asp Ile Asp Ile
305                 310                 315                 320

Glu Thr His Phe Asp Gly Thr Asn Tyr Leu Thr Ile Ala Pro Gly Val
            325                 330                 335

Val Val Gly Tyr Ser Arg Asn Val Lys Thr Glu Ala Ala Leu Arg Ala
        340                 345                 350

Ala Gly Val Thr Val Leu Ser Phe Gly Asn Gln Leu Ser Leu Gly
    355                 360                 365

Met Gly Ser Ala Arg Cys Met Ser Met Pro Leu Val Arg Glu Asp Val
370                 375                 380

Lys
385                 390                 395                 400

<210> SEQ ID NO 10
<211> LENGTH: 401
<212> TYPE: PRT
<213> ORGANISM: Mycoplasma gallinarum

<400> SEQUENCE: 10

Met Ser Lys Ile Arg Val Tyr Ser Glu Ile Gly Asn Leu Lys Lys Val
1               5                   10                  15

Leu Val His Thr Pro Gly Asp Glu Ile Arg Arg Ile Ser Pro Ser Arg
            20                  25                  30

Leu Glu Glu Leu Leu Phe Ser Ala Val Leu Glu Pro Asn Ala Ala Ile

```
                    35                  40                  45
        Glu Glu His Lys Arg Phe Val Lys Leu Leu Glu Asp Arg Gly Ile Gln
         50                  55                  60

Ala Ile Gln Leu Ser Asp Leu Val Ala Glu Thr Tyr Val Lys Tyr Ala
         65                  70                  75                  80

Thr Ala Glu Gln Lys Ala Ala Phe Ile Glu Lys Tyr Leu Asp Glu Ala
                             85                  90                  95

Thr Pro Ala Leu Ser Ala Glu Asn Arg Glu Arg Ala Lys Lys Tyr Ile
                            100                 105                 110

Leu Ser Leu Glu Met Gln Pro Val Lys Met Ile Arg Thr Met Met Ala
                    115                 120                 125

Gly Leu Ser Lys Tyr Glu Leu Asn Val Glu Ser Asn Ile Glu Leu Ile
                    130                 135                 140

Ile Asp Pro Met Pro Asn Leu Tyr Phe Thr Arg Asp Pro Phe Ala Ser
        145                 150                 155                 160

Ala Gly Asn Gly Ile Ser Leu Asn Asn Met Lys Tyr Val Val Arg Lys
                            165                 170                 175

Arg Glu Thr Ile Phe Ala Glu Phe Ile Phe Ala Ile His Pro Glu Tyr
                            180                 185                 190

Lys Glu Thr Pro His Trp Phe Asp Arg Leu Asp His Gly Ser Ile Glu
                    195                 200                 205

Gly Gly Asp Val Phe Val Tyr Asn Lys Asp Thr Leu Val Ile Gly Val
                    210                 215                 220

Ser Glu Arg Thr Asn Lys Glu Ala Ile Ile Thr Ile Ala Lys His Ile
        225                 230                 235                 240

Gln Asp Asn Lys Glu Ala Glu Phe Lys Lys Ile Val Ala Ile Asn Val
                            245                 250                 255

Pro Pro Met Pro Asn Leu Met His Leu Asp Thr Trp Leu Thr Met Val
                            260                 265                 270

Asp Lys Asn Lys Phe Ile Tyr Ser Pro Asn Met Leu Ser Val Leu Lys
                    275                 280                 285

Ile Trp Glu Ile Asp Leu Ala Lys Pro Ile Glu Met Val Glu Ser Asn
        290                 295                 300

Lys Ser Leu Thr Glu Val Leu Glu Ser Ile Ile Gly Glu Lys Pro Ile
        305                 310                 315                 320

Leu Ile Pro Ile Ala Gly Glu Gly Ala Ser Gln Leu Asp Ile Asp Ile
                            325                 330                 335

Glu Thr His Phe Asp Gly Thr Asn Tyr Leu Thr Ile Ala Pro Gly Val
                            340                 345                 350

Val Val Gly Tyr Ser Arg Asn Glu Lys Thr Glu Lys Ala Leu Lys Ala
                    355                 360                 365

Ala Gly Ile Thr Val Leu Ser Phe Glu Gly Asn Gln Leu Ser Leu Gly
                    370                 375                 380

Met Gly Ser Ala Arg Cys Met Ser Met Pro Leu Val Arg Glu Asp Val
        385                 390                 395                 400

Lys

<210> SEQ ID NO 11
<211> LENGTH: 405
<212> TYPE: PRT
<213> ORGANISM: Mycoplasma pirum

<400> SEQUENCE: 11

Met Asn Ser Asn Gln Lys Gly Ile His Val Tyr Ser Glu Ile Gly Lys
```

```
  1               5                   10                  15
Leu Lys Glu Val Leu Val His Arg Pro Gly Arg Glu Leu Asp Phe Leu
             20                  25                  30

Asp Pro Thr Arg Leu Asp Glu Leu Leu Phe Ala Ala Thr Leu Glu Ala
             35                  40                  45

Glu Thr Ala Arg Leu Glu His Asp Asn Phe Thr Asn Ala Leu Lys Asn
             50                  55                  60

Gln Gly Val Thr Val Ile Glu Leu Ala Asp Leu Val Ala Gln Thr Tyr
 65                  70                  75                  80

Ser Ser Ser Thr Pro Thr Ile Lys Ala Ala Phe Ile Asn Lys Tyr Leu
                 85                  90                  95

Asp Glu Ala Thr Pro Ala Leu Thr Thr Lys Leu Arg Thr Leu Val Lys
            100                 105                 110

Asp Phe Leu Thr Lys Gln Lys Ser Val Arg Lys Met Val Asp Tyr Met
            115                 120                 125

Ile Gly Gly Ile Leu Ser Thr Asp Leu Asn Ile Lys Gly Lys Pro Glu
            130                 135                 140

Leu Ile Val Glu Pro Met Pro Asn Ala Tyr Phe Thr His Asp Pro Phe
145                 150                 155                 160

Ala Ser Val Gly Asn Gly Val Thr Leu His Tyr Met Lys His Asn Val
                165                 170                 175

Arg Arg Arg Glu Val Leu Phe Ser Glu Phe Ile Phe Asn Asn Asn Glu
            180                 185                 190

Arg Phe Gln Asn Thr Pro Arg Tyr Ile Val Pro Thr Lys Gly Leu Asp
            195                 200                 205

Ile Glu Gly Gly Asp Val Phe Val Tyr Asn Lys Asn Thr Leu Val Val
210                 215                 220

Gly Val Ser Glu Arg Thr Lys Met Val Thr Ile Lys Glu Leu Ala Lys
225                 230                 235                 240

Asn Ile Leu Lys Asn Lys Glu Cys Leu Phe Lys Lys Ile Tyr Ala Ile
                245                 250                 255

Asn Val Pro Lys Met Pro Asn Leu Met His Leu Asp Thr Trp Leu Thr
            260                 265                 270

Met Leu Asp His Asn Lys Phe Leu Tyr Ser Pro Asn Met Leu Ser Val
            275                 280                 285

Leu Lys Ile Trp Glu Ile Asp Ile Ser Ser Gly Lys Ser Ile Ser Ser
            290                 295                 300

Pro Lys Glu Leu Asn Met Asp Leu Ser Lys Ala Leu Ser Ile Ile Ile
305                 310                 315                 320

Gly Lys Lys Pro Ile Leu Ile Pro Val Ala Gly Glu Asn Ala Ser Gln
                325                 330                 335

Ile Asp Ile Asn Ile Glu Thr Asn Phe Asp Ala Thr Asn Tyr Leu Val
            340                 345                 350

Thr Gln Pro Gly Val Val Gly Tyr Ser Arg Asn Lys Lys Thr Glu
            355                 360                 365

Ala Ala Leu Ile Lys Ala Gly Ile Glu Val Ile Pro Phe Gln Gly Asn
            370                 375                 380

Gln Leu Ser Leu Gly Met Gly Ser Ala Arg Cys Met Ser Met Pro Leu
385                 390                 395                 400

Ile Arg Glu Asp Val
            405

<210> SEQ ID NO 12
```

-continued

```
<211> LENGTH: 404
<212> TYPE: PRT
<213> ORGANISM: Mycoplasma primatum

<400> SEQUENCE: 12

Met Ser Lys Ser Lys Ile Asn Val Tyr Ser Glu Tyr Gly Asn Leu Lys
1               5                   10                  15

Glu Val Leu Val His Thr Pro Gly Asp Glu Ile Arg Arg Ile Thr Pro
            20                  25                  30

Ser Arg Leu Asp Glu Leu Leu Phe Ser Ala Ile Leu Glu Pro Lys Ser
        35                  40                  45

Ala Ile Ala Glu His Lys Ser Phe Cys Gln Ile Leu Lys Asp Asn Lys
    50                  55                  60

Val Lys Ala Ile Gln Leu Asp Glu Leu Val Ala Ala Thr Tyr Lys Gly
65                  70                  75                  80

Val Ser Glu Ser Val Gln Asn Ser Phe Val Glu Arg Trp Leu Asp Glu
                85                  90                  95

Cys Glu Pro Lys Leu Glu Asn Asn Val Arg Pro Ile Val Lys Glu Tyr
            100                 105                 110

Leu Leu Lys Ala Ala Glu Gln Ser Val Lys Lys Met Ile Arg Ile Met
        115                 120                 125

Met Ala Gly Ile Asp Lys Arg Glu Ile Gly Val Glu Ser Glu Val Asp
    130                 135                 140

Phe Ile Val Asp Pro Met Pro Asn Leu Tyr Phe Thr Arg Asp Pro Phe
145                 150                 155                 160

Ala Ser Val Gly Asn Gly Ile Thr Leu His His Met Lys Tyr Val Val
                165                 170                 175

Arg Gln Arg Glu Thr Leu Phe Ser Glu Phe Ile Phe Asp Asn His Pro
            180                 185                 190

Asp Tyr Lys Phe Val Pro Arg Tyr Phe Asp Arg Asp Asp Glu Gly Lys
        195                 200                 205

Ile Glu Gly Gly Asp Val Phe Ile Tyr Asn Ser Lys Thr Leu Val Val
    210                 215                 220

Gly Ile Ser Glu Arg Thr Asn Lys Asp Ala Ile Arg Ile Val Ala Lys
225                 230                 235                 240

Lys Ile Gln Ala Asn Ala Asp Ala Lys Phe Glu Lys Ile Phe Ala Ile
                245                 250                 255

Asn Val Pro Pro Met Pro Asn Leu Met His Leu Asp Thr Trp Leu Thr
            260                 265                 270

Met Leu Asp Ser Asn Lys Phe Leu Tyr Ser Pro Asn Met Leu Ser Val
        275                 280                 285

Leu Lys Val Trp Glu Ile Asn Leu Asp Asp Pro Ala Leu Glu Trp Lys
    290                 295                 300

Glu Ile Ser Gly Ser Leu Glu Glu Ile Leu Thr Tyr Ile Ile Gly Lys
305                 310                 315                 320

Lys Pro Ile Leu Ile Pro Ile Ala Gly Lys Gly Ala Ser Gln Phe Glu
                325                 330                 335

Ile Asp Ile Glu Thr His Phe Asp Gly Thr Asn Tyr Leu Ala Ile Ala
            340                 345                 350

Pro Ser Val Val Ile Gly Tyr Ser Arg Asn Glu Leu Thr Glu Lys Ala
        355                 360                 365

Leu Lys Lys Ala Gly Val Lys Val Leu Ser Leu Asp Gly Asn Gln Leu
    370                 375                 380

Ser Leu Gly Met Gly Ser Ala Arg Cys Met Ser Met Pro Leu Ile Arg
```

```
385                 390                 395                 400
Glu Asp Val Lys

<210> SEQ ID NO 13
<211> LENGTH: 401
<212> TYPE: PRT
<213> ORGANISM: Mycoplasma lipofaciens

<400> SEQUENCE: 13

Met Ser Lys Ile Asn Val Tyr Ser Glu Val Gly Val Leu Lys Glu Val
1               5                   10                  15

Leu Val His Thr Pro Gly Asp Glu Ile Arg Arg Val Ala Pro Ser Arg
            20                  25                  30

Leu Asp Glu Leu Leu Phe Ser Ala Ile Leu Glu Pro Gln Asp Ala Ile
        35                  40                  45

Ala Glu His Lys Arg Phe Ile Lys Ile Leu Glu Asp Asn Asn Ile Lys
    50                  55                  60

Val Ile Gln Leu Asp Glu Leu Val Ser Glu Thr Trp Glu Lys Ala Thr
65                  70                  75                  80

Ala Glu Gln Arg Asp Ala Phe Ile Glu Lys Trp Leu Asp Glu Ala Glu
                85                  90                  95

Pro Val Leu Asp Ala Lys Leu Arg Glu Thr Val Lys Lys Tyr Leu Leu
            100                 105                 110

Ser Leu Asn Pro Val Lys Lys Met Val Arg Thr Met Met Ala Gly Ile
        115                 120                 125

Asp Lys Lys Glu Leu Lys Ile Glu Leu Asp Arg Asp Leu Val Val Asp
    130                 135                 140

Pro Met Pro Asn Leu Tyr Phe Thr Arg Asp Pro Phe Ala Ser Ala Gly
145                 150                 155                 160

Asn Gly Ile Ser Leu Asn Asn Met Lys Tyr Val Thr Arg Lys Arg Glu
                165                 170                 175

Thr Ile Phe Ala Glu Phe Ile Phe Asn Ile His Pro Asp Tyr Lys Thr
            180                 185                 190

Thr Pro His Trp Phe Asp Arg Leu Asp Lys Gly Asn Ile Glu Gly Gly
        195                 200                 205

Asp Val Phe Ile Tyr Asn Lys Asp Thr Leu Val Leu Gly Val Ser Glu
    210                 215                 220

Arg Thr Asn Lys Asp Ala Val Met Thr Ile Ala Lys His Ile Gln Ser
225                 230                 235                 240

Asn Glu Gln Ala Lys Phe Lys Lys Leu Val Ala Ile Asn Val Pro Pro
                245                 250                 255

Met Pro Asn Leu Met His Leu Asp Thr Trp Leu Thr Met Val Asp His
            260                 265                 270

Asp Lys Phe Leu Tyr Ser Pro Asn Met Leu Ser Val Leu Lys Ile Trp
        275                 280                 285

Glu Ile Asp Leu Thr Pro Gly Lys Glu Ile Glu Met Val Glu Ser Thr
    290                 295                 300

Lys Ser Leu Ser Asp Met Leu Glu Ser Ile Ile Gly Lys Lys Pro Val
305                 310                 315                 320

Leu Ile Pro Ile Ala Gly Lys Asp Ala Ser Gln Leu Asp Ile Asp Ile
                325                 330                 335

Glu Thr His Phe Asp Gly Thr Asn Tyr Leu Thr Ile Arg Pro Gly Val
            340                 345                 350

Val Val Gly Tyr Ser Arg Asn Cys Leu Thr Glu Gln Ala Leu Lys Asp
```

```
                355                 360                 365
Ala Gly Val Thr Val Leu Ser Phe Asp Gly Asn Gln Leu Ser Leu Gly
    370                 375                 380

Met Gly Ser Ala Arg Cys Met Ser Met Pro Leu Val Arg Glu Asp Ile
385                 390                 395                 400

Lys

<210> SEQ ID NO 14
<211> LENGTH: 405
<212> TYPE: PRT
<213> ORGANISM: Mycoplasma felifaucium

<400> SEQUENCE: 14

Met Asn Lys Ile Asn Val Tyr Ser Glu Ile Gly Lys Leu Lys Glu Val
1               5                   10                  15

Leu Val His Thr Pro Gly Asn Glu Ile Arg Arg Ile Ser Pro Ser Arg
                20                  25                  30

Leu Asp Glu Leu Leu Phe Ser Ala Leu Leu Pro Asn Phe Ala Ala
            35                  40                  45

Lys Glu His Thr Ala Phe Cys Glu Ile Leu Lys Glu Asn Gly Ile Lys
    50                  55                  60

Ala Ile Gln Leu Val Asp Leu Val Ser Asp Thr Trp Arg Ile Ala Ser
65                  70                  75                  80

Glu Lys Ala Lys Thr Glu Phe Ile Glu Arg Trp Leu Asp Glu Cys Glu
                85                  90                  95

Pro Lys Leu Asp Ser Asn Leu Arg Glu Ile Val Arg Lys His Ile Tyr
            100                 105                 110

Ala Ile Glu Lys Arg Ser Val Lys Arg Met Val Lys Thr Met Met Ala
        115                 120                 125

Gly Ile Glu Arg Arg Glu Leu Pro Val Thr Ser Lys Glu Val Ala Arg
130                 135                 140

Glu Leu Val Val Asp Pro Met Pro Asn Leu Tyr Phe Thr Arg Asp Pro
145                 150                 155                 160

Phe Ala Ser Val Gly Asn Gly Ile Ser Leu His His Met Lys Tyr Val
                165                 170                 175

Thr Arg Gln Arg Glu Thr Ile Phe Ala Glu Phe Val Phe Gly Asn His
            180                 185                 190

Pro Asp Tyr Ile Asp Thr Pro Arg Trp Phe Asp Arg Ser Asp Asp Gly
        195                 200                 205

Arg Ile Glu Gly Gly Asp Val Phe Ile Tyr Gly Ser Lys Thr Leu Val
210                 215                 220

Ile Gly Val Ser Glu Arg Thr Asn Lys Glu Ala Ile Lys Val Met Ala
225                 230                 235                 240

Lys Lys Ile Gln Ala Asn Lys Glu Ala Thr Phe Glu Lys Ile Tyr Ala
                245                 250                 255

Ile Asn Val Pro Pro Met Pro Asn Leu Met His Leu Thr Trp Leu
            260                 265                 270

Thr Met Leu Asp Lys Asn Lys Phe Leu Tyr Ser Pro Asn Met Leu Ala
        275                 280                 285

Val Leu Gln Val Trp Glu Ile Asp Leu Lys Asp Pro Glu Leu Thr Trp
    290                 295                 300

His Glu Leu Ser Gly Ser Leu Glu Glu Ile Leu His Lys Ile Ile Gly
305                 310                 315                 320

Arg Lys Pro Ile Leu Ile Pro Ile Ala Gly His Gly Ala Gln Gln Ile
```

-continued

```
                325                 330                 335

Asp Ile Asp Ile Glu Thr His Phe Asp Gly Thr Asn Tyr Leu Ala Ile
            340                 345                 350

Ala Pro Gly Val Val Val Gly Tyr Asn Arg Asn Val Leu Thr Glu Arg
        355                 360                 365

Ala Leu Lys Lys Ala Gly Ile Lys Val Leu Ser Phe Glu Gly Asn Gln
    370                 375                 380

Leu Ser Leu Gly Met Gly Ser Ala Arg Cys Met Ser Met Pro Leu Ile
385                 390                 395                 400

Arg Glu Asn Leu Lys
                405
```

<210> SEQ ID NO 15
<211> LENGTH: 404
<212> TYPE: PRT
<213> ORGANISM: Mycoplasma imitans

<400> SEQUENCE: 15

```
Met Phe Asn Lys Ile Lys Val Tyr Ser Glu Ile Gly Arg Leu Arg Lys
1               5                   10                  15

Val Leu Val His Thr Pro Gly Lys Glu Leu Glu Tyr Val Thr Pro Gln
            20                  25                  30

Arg Leu Asp Glu Leu Leu Phe Ser Ser Leu Leu Asn Pro Val Lys Ala
        35                  40                  45

Arg Gln Glu His Glu Ala Phe Ile Lys Ile Leu Gln Asp Gln Gly Val
    50                  55                  60

Glu Cys Val Gln Leu Thr Thr Leu Thr Ala Gln Thr Phe Gln Ser Ala
65                  70                  75                  80

Thr Ser Glu Val Lys Glu Lys Phe Ile Asn Arg Trp Leu Asp Glu Cys
                85                  90                  95

Leu Pro Lys Leu Ser Asp Asp Asn Arg Ile Lys Val Tyr Ala Tyr Leu
            100                 105                 110

Lys Asp Leu Ser Ser Asp Pro Glu Val Met Ile Arg Lys Met Met Ser
        115                 120                 125

Gly Ile Leu Ala Lys Glu Val Asn Val Gln Ser Asp Val Glu Leu Ile
    130                 135                 140

Ala Asp Pro Met Pro Asn Leu Tyr Phe Thr Arg Asp Pro Phe Ala Ser
145                 150                 155                 160

Ile Gly Lys Gly Val Thr Leu His Ser Met Phe His Pro Thr Arg Lys
                165                 170                 175

Arg Glu Thr Ile Phe Ala Asp Phe Val Phe Ser His His Pro Glu Tyr
            180                 185                 190

Lys Gln Thr Pro Lys Tyr Tyr Ser Arg Leu Asn Glu Tyr Ser Ile Glu
        195                 200                 205

Gly Gly Asp Leu Phe Val Tyr Asp Asp Lys Thr Leu Val Ile Gly Val
    210                 215                 220

Ser Glu Arg Thr Glu Lys Lys Ala Ile Gln Phe Leu Ala Glu Lys Leu
225                 230                 235                 240

Arg Glu Asn Tyr Glu Thr Thr Phe Glu Lys Ile Tyr Ala Ile Asn Val
                245                 250                 255

Pro Lys Met Ser Asn Leu Met His Leu Asp Thr Trp Leu Thr Met Leu
            260                 265                 270

Asp Tyr Asp Lys Phe Leu Tyr Ser Pro Asn Met Met Gly Val Leu Lys
        275                 280                 285
```

```
Ile Trp Glu Ile Asp Leu Thr His Glu Gln Leu Ser Trp Arg Glu Leu
    290                 295                 300
Asn Glu Ser Leu Glu Glu Phe Leu Ser Met Val Ile Gly Lys Lys Ala
305                 310                 315                 320
Thr Thr Ile Pro Val Ala Gly Glu Asp Ser Thr Gln Ile Glu Ile Asp
                325                 330                 335
Val Glu Thr Asn Phe Asp Ala Thr Asn Phe Leu Val Ile Gln Pro Gly
                340                 345                 350
Val Val Val Gly Tyr Asp Arg Asn Tyr Lys Thr Asn Gln Ala Leu Val
            355                 360                 365
Asn Ala Gly Ile Lys Val Leu Ser Trp Asn Gly Asp Gln Leu Ser Leu
370                 375                 380
Gly Met Gly Ser Ala Arg Cys Met Ser Met Pro Leu Tyr Arg Asp Pro
385                 390                 395                 400
Ile Lys Lys Gly

<210> SEQ ID NO 16
<211> LENGTH: 401
<212> TYPE: PRT
<213> ORGANISM: Mycoplasma opalescens

<400> SEQUENCE: 16

Met Ser Lys Ile Asn Val Tyr Ser Glu Ile Gly Thr Leu Lys Glu Val
1               5                   10                  15
Leu Val His Thr Pro Gly Asp Glu Ile Arg Arg Val Ala Pro Ala Arg
                20                  25                  30
Leu Asp Glu Leu Leu Phe Ser Ala Ile Leu Glu Pro Asn His Ala Ile
            35                  40                  45
Ala Glu His Lys Ala Phe Ile Lys Ile Leu Glu Asp Asn Gly Ile Lys
        50                  55                  60
Val Ile Gln Leu Asp Glu Leu Val Val Gln Thr Trp Asn Gln Val Asp
65                  70                  75                  80
Glu Ala Thr Arg Lys Ala Phe Val Thr Lys Trp Leu Asp Glu Cys Glu
                85                  90                  95
Pro Lys Leu Glu Ser Asn Val Arg Val Glu Val Glu Lys Tyr Ile Tyr
                100                 105                 110
Ser Leu Ala Lys Glu Pro Lys Lys Met Val Arg Thr Met Met Ala Gly
            115                 120                 125
Ile Ser Lys Glu Glu Leu Pro Leu Asn Val Asn Arg Pro Leu Val Val
        130                 135                 140
Asp Pro Met Pro Asn Leu Tyr Phe Thr Arg Asp Pro Phe Ala Ser Val
145                 150                 155                 160
Gly Thr Gly Ile Ser Leu His His Met Lys Tyr Val Thr Arg Gln Arg
                165                 170                 175
Glu Thr Ile Phe Ala Gln Phe Val Phe Asp Asn His Lys Asp Tyr Asn
                180                 185                 190
Thr Val Pro Arg Trp Phe Asp Asn Lys Asp Gln Gly Arg Ile Glu Gly
            195                 200                 205
Gly Asp Val Phe Ile Tyr Asn Thr Lys Thr Leu Val Ile Gly Val Ser
        210                 215                 220
Glu Arg Thr Asp Lys Asp Ala Ile Lys Ile Met Ala Lys Lys Ile Gln
225                 230                 235                 240
Ala Asp Lys Asn Cys Lys Phe Glu Lys Ile Phe Ala Ile Asn Val Pro
                245                 250                 255
```

-continued

```
Pro Met Pro Asn Leu Met His Leu Asp Thr Trp Leu Thr Met Val Asp
            260                 265                 270

Arg Asn Lys Phe Leu Tyr Ser Pro Asn Met Leu Ser Val Leu Lys Val
275                 280                 285

Trp Glu Ile Asp Leu Lys Asp Ala Ser Leu Ala Trp Lys Glu Ile Glu
        290                 295                 300

Gly Ser Leu Ser Gln Ile Leu Glu Lys Ile Ile Gly Glu Lys Pro Ile
305                 310                 315                 320

Leu Ile Pro Ile Ala Gly Glu Asn Ala Ser Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Val Lys Thr Glu Gln Ala Leu Lys Ala
        355                 360                 365

Ala Gly Val Lys Val Leu Ser Phe Glu Gly Asn Gln Leu Ser Leu Gly
    370                 375                 380

Met Gly Ser Ala Arg Cys Met Ser Met Pro Leu Ile Arg Glu Asp Leu
385                 390                 395                 400

Lys
```

<210> SEQ ID NO 17
<211> LENGTH: 431
<212> TYPE: PRT
<213> ORGANISM: Mycoplasma moatsii

<400> SEQUENCE: 17

```
Met Gly Ile L

```
Ile Ser Lys Arg Asp Gly Lys Glu Thr Ile Glu Gly Gly Asp Val Phe
225                 230                 235                 240

Ile Tyr Thr Lys Asp Val Leu Ala Ile Gly Val Ser Glu Arg Thr Asn
                245                 250                 255

Met Glu Ala Ile Leu Arg Ile Ala Thr Asn Ile Lys Lys Asp Lys Asn
            260                 265                 270

Cys Glu Phe Lys Lys Ile Val Ala Ile Asn Val Pro Pro Met Gly Asn
        275                 280                 285

Leu Met His Leu Asp Thr Trp Leu Thr Met Leu Asp Lys Asp Leu Phe
    290                 295                 300

Leu Tyr Ser Gly Asn Ile Lys Ser Ala Leu Lys Val Trp Glu Ile Asp
305                 310                 315                 320

Leu Thr Lys Pro Ile Thr Pro Lys Ser Pro Lys Leu Ser Thr Ala Lys
                325                 330                 335

Leu Ala Asp Ile Leu Ala Lys Ile Val Gly Lys Lys Val Arg Met Ile
            340                 345                 350

Pro Ile Gly Gly Lys Asp Gly Asn Gln Met Asp Ile Asp Ile Glu Thr
        355                 360                 365

His Phe Asp Gly Thr Asn Tyr Leu Ala Ile Ala Pro Gly Val Val Val
    370                 375                 380

Gly Tyr His Arg Asn Arg Lys Thr Gln Lys Ala Leu Glu Glu Ala Gly
385                 390                 395                 400

Val Lys Val Leu Ala Phe Gln Gly Asn Gln Leu Ser Leu Gly Met Gly
                405                 410                 415

Ser Ala Arg Cys Met Ser Met Pro Leu Val Arg Glu Glu Val Lys
            420                 425                 430
```

<210> SEQ ID NO 18
<211> LENGTH: 399
<212> TYPE: PRT
<213> ORGANISM: Mycoplasma elephantis

<400> SEQUENCE: 18

```
Met Ser Gln Ile Asn Val Phe Ser Glu Ile Gly Gln Leu Lys Glu Val
1               5                   10                  15

Leu Val His Thr Pro Gly Asp Glu Ile Arg Arg Ile Ser Pro Lys Arg
            20                  25                  30

Tyr Asn Glu Leu Leu Phe Ser Ala Ile Leu Glu Ala Asp Val Ala Ile
        35                  40                  45

Lys Glu His Lys Ser Phe Val Lys Ile Leu Glu Glu Asn Asn Val Lys
    50                  55                  60

Val Ile Gln Leu Lys Asp Ile Leu Leu Glu Thr Trp Asn Ile Cys Ser
65                  70                  75                  80

Lys Glu Ala Lys Asn Ile Phe Ile Asn Lys Trp Ile Glu Glu Ala Gln
                85                  90                  95

Pro Val Ile His Ser Ser Ser Leu Lys Glu Lys Ile Lys Leu Phe Leu
            100                 105                 110

Lys Ser Lys Thr Pro Leu Glu Ile Ile Asp Ile Met Met Lys Gly Ile
        115                 120                 125

Leu Lys Gln Glu Leu Gly Ile Glu Tyr Lys His Glu Leu Ile Ile Asp
    130                 135                 140

Pro Met Pro Asn Leu Tyr Phe Thr Arg Asp Pro Phe Thr Ser Met Gly
145                 150                 155                 160

Ser Gly Ile Thr Ile Asn Asn Met Lys Tyr Gln Thr Arg Lys Arg Glu
                165                 170                 175
```

Thr Ile Phe Ser Glu Phe Ile Phe Asn Asn His Pro Lys Tyr Lys Asn
            180                 185                 190

Thr Pro Arg Trp Phe Asp Arg Phe Asp Ser Gly Asn Ile Glu Gly Gly
        195                 200                 205

Asp Leu Phe Val Tyr Thr Lys Glu Thr Ile Val Val Gly Val Ser Glu
    210                 215                 220

Arg Thr Lys Lys Lys Ala Ile Leu Lys Ile Ala Lys Asn Ile Gln Glu
225                 230                 235                 240

Asn Asn Asn Ser Phe Lys Lys Ile Val Val Ile Lys Val Pro Ile Met
                245                 250                 255

Gln Asn Leu Met His Leu Asp Thr Trp Ile Val Met Val Asp Phe Asp
            260                 265                 270

Lys Phe Ile Tyr Ser Pro Asn Val Thr Lys Ser Leu Lys Phe Trp Glu
        275                 280                 285

Ile Asp Leu Thr Lys Lys Pro Lys Phe Ile Gln Leu Lys Asn Glu Thr
    290                 295                 300

Leu Glu Asp Val Leu Tyr Arg Val Ile Gly Lys Lys Pro Ile Leu Ile
305                 310                 315                 320

Pro Val Ala Gly Glu Asn Ala Asn Gln Ile Asp Ile Asp Val Glu Thr
                325                 330                 335

His Phe Asp Ala Thr Asn Tyr Leu Thr Ile Arg Pro Gly Val Val Val
            340                 345                 350

Gly Tyr Ser Arg Asn Lys Lys Thr Glu Glu Ala Leu Ile Asn Ala Gly
        355                 360                 365

Val Lys Val Tyr Ala Phe Glu Gly Asn Gln Leu Ser Leu Gly Met Gly
    370                 375                 380

Ser Ala Arg Cys Met Ser Met Pro Leu Ile Arg Glu Asp Ile Ile
385                 390                 395

<210> SEQ ID NO 19
<211> LENGTH: 399
<212> TYPE: PRT
<213> ORGANISM: Mycoplasma testudinis

<400> SEQUENCE: 19

Met Lys Asn Ile Asn Val Tyr Ser Glu Val Gly Lys Leu Lys Glu Val
1               5                   10                  15

Val Val His Thr Pro Gly Glu Glu Leu His Asn Val Ala Pro Ser Arg
            20                  25                  30

Leu Gln Glu Leu Leu Thr Ser Ala Val Leu Glu Pro Val Ala Arg
        35                  40                  45

Lys Glu His Leu Lys Phe Ile Lys Ile Leu Asn Asp Tyr Gly Val Lys
    50                  55                  60

Val Ile Gln Ile Val Asp Leu Ile Thr Glu Thr Tyr Glu Ala Val Asp
65                  70                  75                  80

Ser Asn Lys Lys Glu Ala Phe Ile Asn Asn Trp Leu Asp Asn Ser Val
                85                  90                  95

Pro Lys Leu Thr Asp Lys Asn Arg Met Ile Leu Arg Asn Tyr Leu Thr
            100                 105                 110

Gln Phe Ser Thr Lys Ala Met Ile Arg Lys Met Ile Ser Gly Ile Arg
        115                 120                 125

Ala Lys Glu Leu Asn Leu Lys Thr Pro Ser Ala Leu Leu Val Asp Pro
    130                 135                 140

Met Pro Asn Leu Cys Phe Ala Arg Asp Thr Phe Ala Cys Val Gly Ser

```
145                 150                 155                 160
Ala Ile Ser Leu Ser Thr Met Lys His Pro Thr Arg Arg Glu Ala
                165                 170                 175

Leu Leu Thr Glu Phe Ile Phe Gln Asn His Pro Lys Tyr Lys Asp Val
                180                 185                 190

Ile Lys Tyr Phe Asp Ser Lys Asn Ser Lys Ala Thr Ile Glu Gly Gly
                195                 200                 205

Asp Ile Phe Val Tyr Asn Pro Lys Thr Leu Val Val Gly Asn Ser Glu
210                 215                 220

Arg Thr Asn Met Gln Ala Cys Leu Leu Ala Lys Lys Ile Gln Ser
225                 230                 235                 240

Asn Pro Asn Asn Lys Phe Glu Lys Ile Val Ile Val Asn Val Pro Pro
                245                 250                 255

Leu Pro His Leu Met His Leu Asp Thr Trp Leu Thr Met Val Asp Tyr
                260                 265                 270

Asp Lys Phe Ile Tyr Ser Pro Asn Ile Leu His Thr Leu Lys Phe Trp
                275                 280                 285

Val Ile Asp Leu Lys Lys Arg Lys Leu Glu Ala Val Glu Lys His Asn
        290                 295                 300

Thr Leu Lys Ala Met Leu Arg Met Ile Ile Lys Lys Glu Pro Ile Leu
305                 310                 315                 320

Ile Pro Val Gly Asp Val Gly Ala Asp Gln Leu Asp Ile Asp Leu Glu
                325                 330                 335

Thr His Phe Asp Ala Thr Asn Tyr Leu Ala Leu Ala Pro Gly Val Val
                340                 345                 350

Val Gly Tyr Asp Arg Asn Ile Lys Thr Gln Arg Ala Leu Glu Lys Ala
                355                 360                 365

Gly Val Lys Val Leu Ser Phe Ser Gly Asn Gln Leu Ser Leu Ala Met
                370                 375                 380

Gly Ser Ala Arg Cys Leu Ser Met Pro Leu Ile Arg Glu Glu Asn
385                 390                 395

<210> SEQ ID NO 20
<211> LENGTH: 410
<212> TYPE: PRT
<213> ORGANISM: Mycoplasma canadense

<400> SEQUENCE: 20

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
                35                  40                  45

Leu Glu Ser His Asp Ala Arg Lys Glu His Lys Gln Phe Val Ser Glu
                50                  55                  60

Leu Lys Ala Asn Asp Ile Asn Val Val Glu Leu Thr Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Ala
                100                 105                 110

Ile Val Arg Lys Tyr Leu Lys Gly Ile Gln Pro Thr Arg Lys Leu Ile
                115                 120                 125
```

```
Glu Met Met Met Ala Gly Ile Thr Lys Tyr Asp Leu Gly Ile Glu Ala
        130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ser Leu
        195                 200                 205

Lys Leu Ser Ile Glu Gly Gly Asp Val Phe Val Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ser
290                 295                 300

Glu Pro Gln Pro Val Glu Asn Gly Leu Pro Leu Glu Gly Leu Leu Glu
305                 310                 315                 320

Ser Ile Ile Asn Lys Lys Pro Ile Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 21
<211> LENGTH: 409
<212> TYPE: PRT
<213> ORGANISM: Mycoplasma anseris

<400> SEQUENCE: 21

Met Ser Val Phe Asp Lys Arg Phe Lys Gly Ile His Val Tyr Ser Glu
1               5                   10                  15

Ile Gly Glu Leu Gln Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Ala Glu His Lys Lys Phe Val Ala Thr
    50                  55                  60

Leu Lys Glu Gln Gly Ile Asn Thr Val Glu Leu Thr Asp Leu Val Ala
65                  70                  75                  80

Glu Thr Tyr Asp Leu Ala Ser Gln Glu Ala Arg Asp Asn Leu Leu Glu
                85                  90                  95
```

```
Glu Phe Leu Asp Asp Ser Ala Pro Val Leu Ser Glu His Lys Glu
                100                 105                 110
Ile Val Arg Thr Tyr Leu Lys Gly Ile Lys Gly Thr Arg Lys Leu Ile
            115                 120                 125
Glu Thr Met Met Ala Gly Ile Thr Lys Tyr Asp Leu Gly Ile Glu Ala
        130                 135                 140
Glu Gln Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Ile Phe Ser
            180                 185                 190
Asn His Pro Gln Leu Val Asn Thr Pro Trp Tyr Tyr Asn Pro Ala Glu
        195                 200                 205
Gly Leu Ser Ile Glu Gly Gly Asp Val Phe Ile Tyr Asn Asn Asp Thr
    210                 215                 220
Leu Val Val Gly Val Ser Glu Arg Thr Asp Leu Gln Thr Ile Thr Leu
225                 230                 235                 240
Leu Ala Lys Asn Ile Lys Ala Asn Glu Glu Cys Glu Phe Lys Arg Ile
                245                 250                 255
Val Ala Ile Asn Val Pro Lys Trp Thr Asn Leu Met His Leu Asp Thr
            260                 265                 270
Trp Leu Thr Met Leu Asp Thr Asn Lys Phe Leu Tyr Ser Pro Ile Ala
        275                 280                 285
Asn Asp Val Phe Lys Phe Trp Asp Tyr Asp Leu Val Asn Gly Gly Asp
    290                 295                 300
Glu Pro Gln Pro Val Asp Asn Gly Leu Pro Leu Asn Glu Leu Leu Lys
305                 310                 315                 320
Ser Ile Ile Gly Glu Glu Pro Ile Leu Ile Pro Ile Ala Gly Asp Gly
                325                 330                 335
Ala Thr Gln Ile Glu Ile Glu Arg Glu Thr His Phe Asp Gly Thr Asn
            340                 345                 350
Tyr Leu Ala Ile Ala Pro Gly Val Val Ile Gly Tyr Ser Arg Asn Glu
        355                 360                 365
Lys Thr Asn Ala Ala Leu Glu Ala Ala Gly Ile Lys Val Leu Pro Phe
    370                 375                 380
Lys Gly His Gln Leu Ser Leu Gly Met Gly Asn Ala Arg Cys Met Ser
385                 390                 395                 400
Met Pro Leu Tyr Arg Lys Asp Val Lys
                405

<210> SEQ ID NO 22
<211> LENGTH: 401
<212> TYPE: PRT
<213> ORGANISM: Mycoplasma meleagridis

<400> SEQUENCE: 22

Met Ser Lys Ile Asn Val Tyr Ser Glu Ile Gly Val Leu Lys Glu Val
1               5                   10                  15
Leu Val His Thr Pro Gly Asp Glu Ile Arg Arg Ile Ser Pro Ser Arg
            20                  25                  30
Leu Asp Glu Leu Leu Phe Ser Ala Ile Leu Gln Pro Glu Gln Ala Ile
        35                  40                  45
Lys Glu His Gln Ser Phe Val Lys Ile Leu Gln Asp Arg Gly Ile Lys
```

Val Ile Gln Leu Ser Asp Leu Val Ala Glu Thr Tyr Val Lys Tyr Ala
65                  70                  75                  80

Thr Ser Lys Glu Lys Glu Ser Phe Ile Glu Lys Trp Leu Asp Glu Ala
                85                  90                  95

Thr Pro Ala Leu Asn Ser Glu Asn Arg Ala Arg Val Lys Asn Tyr Ile
            100                 105                 110

Thr Ala Met Gln Gly Gln Pro Val Lys Met Val Arg Ala Met Met Ala
        115                 120                 125

Gly Val Ser Lys Gln Glu Leu Asn Ile Glu Ser Asp Val Glu Leu Ile
    130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ser Ile His Pro Glu Tyr
            180                 185                 190

Lys Gln Thr Pro His Trp Phe Asp Arg Leu Asp Lys Gly Asn Ile Glu
        195                 200                 205

Gly Gly Asp Val Phe Ile Tyr Asn Lys Asp Thr Leu Val Ile Gly Val
    210                 215                 220

Ser Glu Arg Thr Asn Lys Glu Ala Ile Leu Thr Ile Ala Glu His Ile
225                 230                 235                 240

Lys Asn Asn Lys Glu Ala Lys Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Leu Tyr Ser Pro Asn Met Leu Ser Val Leu Lys
        275                 280                 285

Ile Trp Glu Ile Asp Leu Ser Lys Glu Ile Lys Met Val Glu Thr Ser
    290                 295                 300

Lys Pro Leu Ala Asp Val Leu Glu Ser Ile Ile Gly Glu Lys Pro Ile
305                 310                 315                 320

Leu Ile Pro Ile Ala Gly Glu Asn Ala Ser Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Val Lys Thr Glu Ala Ala Leu Lys Ala
        355                 360                 365

Ala Gly Val Thr Val Tyr Ser Phe Asp Gly Asn Gln Leu Ser Leu Gly
    370                 375                 380

Met Gly Ser Gly Arg Cys Met Ser Met Pro Leu Val Arg Glu Asp Val
385                 390                 395                 400

Lys

<210> SEQ ID NO 23
<211> LENGTH: 404
<212> TYPE: PRT
<213> ORGANISM: Mycoplasma alvi

<400> SEQUENCE: 23

Met Ser Ile Lys Glu Asn Gly Ile His Val Tyr Ser Glu Ile Gly Lys
1               5                   10                  15

Leu Arg Asp Val Leu Val His Arg Pro Gly Arg Glu Leu Asn Phe Leu

```
                    20                  25                  30
Asp Pro Ser Arg Leu Asp Glu Leu Leu Phe Ala Ala Thr Leu Glu Pro
                35                  40                  45
Glu Thr Ala Arg Leu Glu His Asp Asn Phe Thr Thr Val Leu Lys Asn
            50                  55                  60
Gln Gly Val Asn Val Ile Glu Leu Ala Asp Leu Val Ser Gln Thr Tyr
65                  70                  75                  80
Ser Lys Val Asp Ser Lys Val Lys Glu Phe Ile Asp Gln Tyr Leu
                85                  90                  95
Asn Glu Ala Thr Pro Lys Leu Thr Ser Glu Leu Ser Lys Lys Val Tyr
            100                 105                 110
Asp Phe Leu Thr Lys Gln Lys Ser Asn Arg Glu Met Val Asp Phe Met
                115                 120                 125
Met Gly Gly Ile Leu Ser Ser Asp Leu Asn Ile Lys Gly Gln Pro Tyr
            130                 135                 140
Leu Ile Val Glu Pro Met Pro Asn Leu Tyr Phe Thr Arg Asp Pro Phe
145                 150                 155                 160
Ala Ser Val Gly Asn Gly Ala Thr Ile His Trp Met Lys His Asn Val
                165                 170                 175
Arg Arg Arg Glu Val Leu Phe Ala Asn Phe Ile Phe Lys Tyr Asn Glu
            180                 185                 190
Arg Phe Gln Asn Thr Pro Lys Tyr Ile Thr Pro Thr Lys Gly Leu Asp
                195                 200                 205
Ile Glu Gly Gly Asp Val Phe Val Tyr Asn Lys Lys Thr Leu Val Val
            210                 215                 220
Gly Val Ser Glu Arg Thr Lys Met Glu Thr Ile Lys Glu Leu Ala Lys
225                 230                 235                 240
Asn Ile Ser Lys Asn Lys Glu Cys Thr Phe Thr Lys Ile Tyr Ala Ile
                245                 250                 255
Asn Val Pro Lys Met Pro Asn Leu Met His Leu Asp Thr Trp Leu Thr
            260                 265                 270
Met Leu Asp Tyr Asn Lys Phe Leu Tyr Ser Pro Asn Met Leu Ser Val
                275                 280                 285
Leu Lys Val Trp Glu Ile Asn Ile Ser Asn Asn Lys Val Ser Ala Pro
            290                 295                 300
Lys Glu Leu Asn Val Asn Leu Glu Lys Ala Leu Ser Met Ile Ile Gly
305                 310                 315                 320
Lys Lys Pro Ile Leu Ile Pro Val Ala Gly Ala Asn Ala Ser Gln Ile
                325                 330                 335
Asp Ile Asn Ile Glu Thr Asn Phe Asp Ala Thr Asn Tyr Leu Val Ile
            340                 345                 350
Glu Pro Gly Val Val Val Gly Tyr Ser Arg Asn Lys Lys Thr Glu Glu
                355                 360                 365
Ala Leu Val Lys Ala Gly Ile Lys Val Leu Pro Phe His Gly Asn Gln
            370                 375                 380
Leu Ser Leu Gly Met Gly Ser Ala Arg Cys Met Ser Met Pro Leu Tyr
385                 390                 395                 400
Arg Glu Asp Val
```

<210> SEQ ID NO 24
<211> LENGTH: 410
<212> TYPE: PRT
<213> ORGANISM: Mycoplasma penetrans -continued

```
<400> SEQUENCE: 24

Met Ser Ser Ile Asp Lys Asn Ser Leu Gly Asn Gly Ile Asn Val Tyr
1               5                   10                  15

Ser Glu Ile Gly Glu Leu Lys Glu Val Leu His Thr Pro Gly Asp
            20                  25                  30

Glu Ile Arg Tyr Thr Ala Pro Ser Arg Leu Glu Glu Leu Leu Phe Ser
            35                  40                  45

Ala Val Leu Lys Ala Asp Thr Ala Ile Glu Glu His Lys Gly Phe Val
        50                  55                  60

Lys Ile Leu Gln Asn Asn Gly Ile Lys Val Ile Gln Leu Cys Asp Leu
65                  70                  75                  80

Val Ala Glu Thr Tyr Glu Leu Cys Ser Lys Glu Val Arg Asn Ser Phe
                85                  90                  95

Ile Glu Gln Tyr Leu Asp Glu Ala Leu Pro Val Leu Lys Lys Glu Ile
            100                 105                 110

Arg Pro Val Val Lys Asp Tyr Leu Leu Ser Phe Pro Thr Val Gln Met
            115                 120                 125

Val Arg Lys Met Met Ser Gly Ile Leu Ala Asn Glu Leu Asn Ile Lys
        130                 135                 140

Gln Asp Asn Pro Leu Ile Ile Asp Gly Met Pro Asn Leu Tyr Phe Thr
145                 150                 155                 160

Arg Asp Pro Phe Ala Ser Met Gly Asn Gly Val Ser Ile Asn Cys Met
                165                 170                 175

Lys Tyr Pro Thr Arg Lys Arg Glu Val Ile Phe Ser Arg Phe Val Phe
            180                 185                 190

Thr Asn Asn Pro Lys Tyr Lys Asn Thr Pro Arg Tyr Phe Asp Ile Val
            195                 200                 205

Gly Asn Asn Gly Thr Ile Glu Gly Gly Asp Ile Phe Ile Tyr Asn Ser
        210                 215                 220

Lys Thr Leu Val Ile Gly Asn Ser Glu Arg Thr Asn Phe Ala Ala Ile
225                 230                 235                 240

Glu Ser Val Ala Lys Asn Ile Gln Ala Asn Lys Asp Cys Thr Phe Glu
                245                 250                 255

Arg Ile Val Val Ile Asn Val Pro Pro Met Pro Asn Leu Met His Leu
            260                 265                 270

Asp Thr Trp Leu Thr Met Leu Asp Tyr Asp Lys Phe Leu Tyr Ser Pro
            275                 280                 285

Asn Met Met Asn Val Leu Lys Ile Trp Glu Ile Asp Leu Asn Val Lys
        290                 295                 300

Pro Val Lys Phe Val Glu Lys Lys Gly Thr Leu Glu Glu Val Leu Tyr
305                 310                 315                 320

Ser Ile Ile Asp Lys Lys Pro Ile Leu Ile Pro Ile Ala Gly Lys Gly
                325                 330                 335

Ala Asn Gln Leu Asp Ile Asp Ile Glu Thr His Phe Asp Gly Thr Asn
            340                 345                 350

Tyr Leu Thr Ile Ala Pro Gly Val Val Gly Tyr Glu Arg Asn Glu
            355                 360                 365

Lys Thr Gln Lys Ala Leu Val Glu Ala Gly Ile Lys Val Leu Ser Phe
        370                 375                 380

Asn Gly Ser Gln Leu Ser Leu Gly Met Gly Ser Ala Arg Cys Met Ser
385                 390                 395                 400

Met Pro Leu Ile Arg Glu Asn Leu Lys Lys
                405                 410
```

<210> SEQ ID NO 25
<211> LENGTH: 404
<212> TYPE: PRT
<213> ORGANISM: Mycoplasma fermentans

<400> SEQUENCE: 25

```
Met Lys Lys Ile Asn Val Tyr Ser Glu Tyr Gly Lys Leu Lys Glu Val
1               5                   10                  15

Leu Val His Thr Pro Gly Asp Glu Ile Arg Arg Ile Ala Pro Ser Arg
                20                  25                  30

Leu Asp Glu Leu Leu Phe Ser Ala Ile Leu Glu Pro Asp Ser Ala Ile
            35                  40                  45

Ala Glu His Lys Arg Phe Val Gln Leu Leu Lys Asp Asn Gly Ile Lys
        50                  55                  60

Val Ile Gln Leu Asp Glu Leu Phe Ala Lys Thr Phe Asp Leu Val Ser
65                  70                  75                  80

Glu Ser Val Lys Gln Ser Phe Ile Glu Arg Trp Leu Asp Glu Cys Glu
                85                  90                  95

Pro Lys Leu Asp Ala Thr Leu Arg Ala Lys Val Lys Glu Tyr Ile Leu
            100                 105                 110

Glu Leu Lys Ala Lys Ser Ser Lys Lys Met Val Arg Val Met Met Ala
        115                 120                 125

Gly Ile Asp Lys Lys Glu Leu Gly Ile Glu Leu Asp Arg Asp Leu Val
    130                 135                 140

Val Asp Pro Met Pro Asn Leu Tyr Phe Thr Arg Asp Pro Phe Ala Ser
145                 150                 155                 160

Val Gly Asn Gly Ile Ser Leu His His Met Lys Tyr Val Thr Arg Gln
                165                 170                 175

Arg Glu Thr Ile Phe Ser Glu Phe Ile Phe Asp Asn Asn Leu Asp Tyr
            180                 185                 190

Asn Thr Val Pro Arg Trp Phe Asp Arg Lys Asp Glu Gly Arg Ile Glu
        195                 200                 205

Gly Gly Asp Val Phe Ile Tyr Ser Ala Asp Thr Leu Val Val Gly Val
    210                 215                 220

Ser Glu Arg Thr Asn Lys Glu Ala Ile Asn Val Met Ala Arg Lys Ile
225                 230                 235                 240

Ala Ala Asp Lys Glu Val Lys Phe Lys Arg Ile Tyr Ala Ile Asn Val
                245                 250                 255

Pro Pro Met Pro Asn Leu Met His Leu Asp Thr Trp Leu Thr Met Leu
            260                 265                 270

Asp Lys Asn Lys Phe Leu Tyr Ser Pro Asn Met Leu Ser Val Leu Lys
        275                 280                 285

Val Trp Arg Ile Asp Leu Asn Asp Pro Asp Phe Val Trp His Glu Ile
    290                 295                 300

Glu Gly Ser Leu Glu Gly Ile Leu Glu Gln Ile Ile Gly Met Lys Pro
305                 310                 315                 320

Ile Leu Ile Pro Ile Ala Gly Lys Gly Ala Ser Gln Leu Asp Ile Asp
                325                 330                 335

Ile Glu Thr His Phe Asp Gly Thr Asn Tyr Leu Thr Ile Ala Pro Ser
            340                 345                 350

Val Val Val Gly Tyr Ser Arg Asn Glu Lys Thr Glu Lys Ala Leu Lys
        355                 360                 365

Ala Ala Lys Val Lys Val Leu Ser Phe Glu Gly Asn Gln Leu Ser Leu
```

```
                370              375              380
Gly Met Gly Ser Ala Arg Cys Met Ser Met Pro Leu Ile Arg Glu Asp
385              390              395              400

Ile Lys Lys Lys

<210> SEQ ID NO 26
<211> LENGTH: 404
<212> TYPE: PRT
<213> ORGANISM: Mycoplasma pneumoniae

<400> SEQUENCE: 26

Met Lys Tyr Asn Ile Asn Val His Ser Glu Ile Gly Gln Leu Gln Thr
1               5                   10                  15

Val Leu Val His Thr Pro Gly Asn Glu Ile Arg Arg Ile Ser Pro Arg
                20                  25                  30

Arg Leu Asp Asp Leu Leu Phe Ser Ala Val Ile Glu Pro Asp Thr Ala
            35                  40                  45

Ile Gln Glu His Gln Thr Phe Cys Gln Leu Leu Gln Glu Gln Asn Ile
        50                  55                  60

Glu Val Val Gln Leu Thr Asp Leu Thr Ala Thr Thr Phe Asp Lys Ala
65                  70                  75                  80

Asn Ala Thr Ala Gln Asn Gln Phe Ile Glu Thr Trp Leu Asp Gln Ala
                85                  90                  95

Glu Pro Lys Leu Thr Pro Glu His Arg Lys Val Ala Lys Gln Tyr Leu
            100                 105                 110

Leu Glu Gln Lys Ala Lys Ser Thr Leu Ser Met Val Arg Ser Met Met
        115                 120                 125

Gly Gly Ile Asp Lys Arg Lys Val Ala Ala Ala Asn Thr Ile Asn Gly
130                 135                 140

Asp Phe Leu Val Asp Pro Met Pro Asn Leu Tyr Phe Thr Arg Asp Pro
145                 150                 155                 160

Phe Ala Ser Ile Gly His Gly Ile Ser Ile Asn Arg Met Lys Tyr Leu
                165                 170                 175

Thr Arg Arg Arg Glu Thr Leu Phe Ala Ser Phe Ile Phe Ala Asn His
            180                 185                 190

Pro Ile Ile Ala Ala Arg Lys Phe Tyr Phe Lys Pro Ile Asp Met Gly
        195                 200                 205

Thr Ile Glu Gly Gly Asp Ile Phe Val Tyr Asp Gln Gln Thr Val Val
210                 215                 220

Met Gly Leu Ser Glu Arg Thr Thr Glu Ala Ala Ile Asn Val Leu Ala
225                 230                 235                 240

Lys Lys Ile Gln Gln Asp Ser Ser Thr Ser Phe Lys Arg Ile Phe Val
                245                 250                 255

Ile Asn Val Pro Gln Leu Pro Asn Leu Met His Leu Asp Thr Trp Leu
            260                 265                 270

Thr Met Leu Asp Arg Asn Lys Phe Leu Tyr Ser Pro Asn Met Leu Ala
        275                 280                 285

Val Leu Lys Ala Trp Arg Ile Asp Phe Thr Asp Pro Ala Leu Lys Trp
290                 295                 300

Asn Glu Ile Ala Gly Asp Leu Ser Thr Ile Leu His Thr Ile Ile Gly
305                 310                 315                 320

Gln Lys Pro Met Leu Ile Pro Ile Ala Gly Ala Asp Ala Asn Gln Thr
                325                 330                 335

Glu Ile Asp Ile Glu Thr His Phe Asp Gly Thr Asn Tyr Leu Thr Ile
```

```
              340                 345                 350
Ala Pro Ser Val Val Gly Tyr Ala Arg Asn Lys Leu Thr His Gln
            355                 360                 365
Thr Leu Glu Ala Ala Gly Val Lys Val Ile Ala Phe Lys Gly Asn Gln
370                 375                 380
Leu Ser Leu Gly Met Gly Ser Ala Arg Cys Met Ser Met Pro Leu Val
385                 390                 395                 400
Arg Lys Pro Leu

<210> SEQ ID NO 27
<211> LENGTH: 414
<212> TYPE: PRT
<213> ORGANISM: Mycoplasma sp.

<400> SEQUENCE: 27

Met Glu Lys Ile His Val Thr Ser Glu Ile Gly Pro Leu Lys Lys Val
1               5                   10                  15
Leu Leu His Arg Pro Gly Asn Glu Leu Leu Asn Leu Thr Pro Asp Thr
                20                  25                  30
Leu Ser Arg Leu Leu Phe Asp Asp Ile Pro Tyr Leu Pro Asp Ala Ile
            35                  40                  45
Lys Glu His Asp Glu Phe Ala Asp Ala Leu Arg Ala Asn Gly Val Glu
        50                  55                  60
Val Val Tyr Leu Glu Asn Leu Met Ala Asp Val Leu Asp Leu Ser Asp
65                  70                  75                  80
Glu Ile Arg Asp Lys Phe Ile Lys Gln Phe Ile Tyr Glu Ala Gly Ile
                85                  90                  95
Arg Thr Pro Lys Tyr Lys Tyr Leu Val Phe Asp Tyr Leu Asp Gln Ile
                100                 105                 110
Thr Asn Ser Lys Lys Leu Val Leu Lys Thr Met Glu Gly Ile Gln Ile
            115                 120                 125
Ser Asp Ile Pro Arg Arg Lys Arg Glu Ile Glu Lys Ser Leu Val Asp
        130                 135                 140
Leu Ile Glu Thr Glu Asp Glu Phe Ile Ala Asp Pro Met Pro Asn Leu
145                 150                 155                 160
Tyr Phe Thr Arg Asp Pro Phe Ala Ser Val Gly Glu Gly Ile Ser Leu
                165                 170                 175
Asn Lys Met Tyr Ser Val Thr Arg Asn Arg Glu Thr Ile Tyr Ala Glu
                180                 185                 190
Tyr Ile Phe Lys Tyr His Pro Asp Tyr Lys Asp Gln Ala Arg Leu Tyr
            195                 200                 205
Tyr Asp Arg Tyr Asn Pro Tyr His Ile Glu Gly Gly Asp Val Leu Asn
        210                 215                 220
Ile Asn Asp His Val Leu Ala Ile Gly Ile Ser Gln Arg Thr Thr Ala
225                 230                 235                 240
Glu Ala Ile Asp Gln Ile Ala Lys Asn Leu Phe Lys Asp Pro Glu Cys
                245                 250                 255
Lys Ile Asp Thr Ile Leu Ala Phe Asn Ile Pro Glu Ser Arg Ala Phe
                260                 265                 270
Met His Leu Asp Thr Val Phe Thr Gln Val Asp Tyr Asp Lys Phe Thr
            275                 280                 285
Tyr His Pro Gly Ile Met Gly Thr Leu Gln Val Phe Glu Ile Thr Glu
        290                 295                 300
Gly Asp Asp Pro Asn Ser Asp Glu Asp Leu Thr Val Thr Glu Ile Asn
```

```
                305                 310                 315                 320

Ala Pro Leu Glu Glu Ile Leu Thr Lys Tyr Val Gly Arg Lys Val Thr
                    325                 330                 335

Leu Ile Pro Cys Ala Gly Gly Asp Lys Val Ser Ala Glu Arg Glu Gln
                    340                 345                 350

Trp Asn Asp Gly Ser Asn Thr Leu Cys Ile Ala Pro Gly Val Val Val
                    355                 360                 365

Val Tyr Asp Arg Asn Asn Leu Thr Asn Ala Val Leu Arg Ser Tyr Gly
            370                 375                 380

Leu Lys Val Ile Glu Ile His Gly Ala Glu Leu Ser Arg Gly Arg Gly
385                 390                 395                 400

Gly Pro Arg Cys Met Ser Met Pro Leu Val Arg Glu Asp Ile
                    405                 410

<210> SEQ ID NO 28
<211> LENGTH: 408
<212> TYPE: PRT
<213> ORGANISM: Mycoplasma sp.

<400> SEQUENCE: 28

Met His Val Thr Ser Glu Ile Lys Lys Leu Lys Val Leu Val His
1               5                   10                  15

Arg Pro Gly Lys Glu Leu Leu Asn Leu Thr Pro Asp Thr Leu Gly Arg
                20                  25                  30

Leu Leu Phe Asp Asp Ile Pro Tyr Leu Lys Asp Ala Ile Leu Glu His
            35                  40                  45

Asp Glu Phe Cys Gln Ile Leu Arg Asp Asn Asp Glu Val Val Val Tyr
        50                  55                  60

Leu Glu Asp Leu Met Ala Glu Thr Leu Asp Glu Asn Pro Gln Val Lys
65                  70                  75                  80

Pro Ser Phe Ile Arg Gln Phe Ile Tyr Glu Ala Gly Val Arg Thr Pro
                85                  90                  95

Lys Tyr Lys Asp Leu Leu Phe Asp Tyr Leu Met Ser Tyr Thr Asn Asn
                100                 105                 110

Lys Glu Leu Val Leu Lys Thr Met Glu Gly Ile Lys Val Ser Glu Val
            115                 120                 125

His Arg Asn Lys Gln Asp Ser Glu Tyr Ser Leu Val Asp Gln Ile Ser
        130                 135                 140

Glu Glu Thr Lys Phe Leu Ala Glu Pro Met Pro Asn Leu Tyr Phe Thr
145                 150                 155                 160

Arg Asp Pro Phe Ala Ser Val Gly Asp Gly Ile Ile Leu Asn Lys Met
                165                 170                 175

His Ser Val Thr Arg Ser Arg Gly Thr Ile Tyr Ala Tyr Tyr Ile Phe
                180                 185                 190

Asn Tyr His Pro Asp Tyr Met Asp Lys Val Pro Lys Tyr Tyr Asp Arg
            195                 200                 205

Glu Asn Pro Phe Ser Ile Glu Gly Gly Asp Val Leu Asn Leu Asn Glu
        210                 215                 220

His Thr Leu Ala Ile Gly Ile Ser Gln Arg Thr Ser Ala Glu Ala Ile
225                 230                 235                 240

Asp Leu Val Ala Lys Asn Met Phe Asn Asp Glu Lys Cys Asn Ile Asp
                245                 250                 255

Thr Ile Leu Ala Phe Lys Ile Pro Glu Cys Arg Ala Phe Met His Leu
                260                 265                 270
```

```
Asp Thr Val Phe Thr Gln Ile Asp Ile Asp Lys Phe Thr Tyr His Pro
        275                 280                 285

Gly Ile Met Asp Thr Leu Glu Val Phe Glu Ile Thr Lys Asn Glu Asp
        290                 295                 300

Asp Leu Asp Glu Val Arg Val Ile Lys Lys Glu Gly Ser Leu Glu Asn
305                 310                 315                 320

Ile Leu Glu Glu Tyr Leu Gly Ile Asp Ile Thr Leu Ile Pro Cys Ala
                325                 330                 335

Gly Gly Asp Lys Ile Ala Ser Glu Arg Glu Gln Trp Asn Asp Gly Thr
            340                 345                 350

Asn Thr Leu Cys Ile Ala Pro Gly Val Val Val Tyr Asn Arg Asn
        355                 360                 365

Asn Ile Thr Asn Glu Val Leu Arg Glu Lys Gly Ile Lys Val Ile Glu
        370                 375                 380

Met Asn Ser Ala Glu Leu Ser Arg Gly Arg Gly Gly Pro Arg Cys Met
385                 390                 395                 400

Ser Met Pro Leu Glu Arg Glu Asp
                405
```

ARGININE DEIMINASE WITH REDUCED CROSS-REACTIVITY TOWARD ADI-PEG 20 ANTIBODIES FOR CANCER TREATMENT

CROSS-REFERENCE TO RELATED APPLICATIONS

This application claims priority under 35 U.S.C. §119(e) to U.S. Application No. 62/051,182, filed Sep. 16, 2014, which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is POLA_005_01US_SeqList_ST25.txt. The text file is about 97 KB, was created on Sep. 15, 2015, and is being submitted electronically via EFS-Web.

BACKGROUND

Technical Field

The present invention relates generally to arginine deiminase (ADI) proteins, including ADI proteins having reduced cross-reactivity with ADI-PEG 20 antibodies. Such ADI proteins are useful for treating arginine-dependent or related diseases such as cancer.

Description of the Related Art

Amino acid deprivation therapy can be an effective treatment of some forms of cancer. To date, there is one known clinical example relevant to this approach which utilizes asparaginase to lower circulating levels of asparagine and inhibit protein synthesis. This treatment is particularly effective for acute lymphoblastic leukemia (Avramis 2005, Viera Pinheiro 2004). Acute lymphoblastic leukemia cells require the amino acid asparagine for growth and proliferation. In contrast, most normal human cells are capable of synthesizing asparagine and are unaffected by asparagine depletion. Therefore, decreasing serum asparagine with asparaginase can selectively kill the cancer cells without harming the normal cells, tissues, and host. An *E. coli* derived form of asparaginase has been approved for human use. However, asparaginase is found only in microbes; which makes it highly immunogenic in humans and also has a short serum half-life following injection (Avramis 2005). To make asparaginase a more effective drug, these drawbacks were minimized by formulating the *E. coli* derived asparaginase with polyethylene glycol (PEG) to reduce the immunogenicity of this enzyme and the associated allergic reactions. In addition, PEG greatly prolongs the circulating half-life of asparaginase, which reduces both the frequency of treatment and the total cost of the therapy. PEG formulated asparaginase is approved for use and is marketed under the trade name Oncaspar® (Oncaspar® 2011, Avramis 2005, Viera Pinheiro 2004, Fu 2007, Zeidan 2008).

Arginine is another non-essential amino acid for humans and mice (for review see Rogers 1994). In humans, arginine can be synthesized from citrulline in two steps via the Krebs (urea) cycle enzymes argininosuccinate synthetase (ASS, L-citrulline:L-aspartate ligase [AMP-forming], EC 6.3.4.5) and argininosuccinate lyase (ASL, L-argininosuccinate arginine-lyase, EC 4.3.2.) (Haines 2011, Wu 2009, Morris 2006, Husson 2003, Tapiero 2002, Rogers 1994). ASS catalyzes the conversion of citrulline and aspartic acid to argininosuccinate, which is then converted to arginine and fumaric acid by ASL. An arginine deficient diet in humans does not evoke hyperammonemia, orotic aciduria, nor alter the rate of whole body nitric oxide (NO) synthesis in adult humans (Tapiero 2002, Castillo 1995, Rogers 1994, Carey 1987, Barbul 1986, Snyderman 1959, Rose 1949). Although preterm infants appear to require arginine (Wu 2004), arginine levels do not correlate with age among infants, children and young adults (Lücke 2007). In 1992, Takaku and Sugimura separately reported that human melanomas and hepatocellular carcinoma (HCC) cell lines appear to require arginine for growth. Other studies showed that pegylated ADI was effective for the treatment of melanomas and hepatomas with few adverse effects.

ADI-PEG 20 treatment requires multiple doses over a period of time. After a number of treatments, anti-ADI-PEG 20 antibodies can develop that may limit its continued effectiveness. Therefore, there is a need in the art for ADI that has reduced cross-reactivity to anti-ADI-PEG20 antibodies for use in treatment in order to improve and extend the efficacy of arginine depletion therapy. The present invention provides this and other advantages for the treatment of cancers.

References: Avramis V I, Panosyan E H. 2005. Clin Pharmacokinet 44:367-393; Barbul A. 1986. J Parenteral Enteral Nutr 10:227-238; Carey G P, et al. 1987. J Nutr 117:1734-1739; Castillo L, et al. 1995. Am J Physiol 268 (Endocrinol Metab 31):E360-367; Fu C H, Sakamoto K M. 2007. Expert Opin Pharmacother 8:1977-1984; Haines R J, et al. 2011. Int J Biochem Mol Biol 2:8-23; Husson A, et al. 2003. Eur J Biochem 270:1887-1899; Lücke T, et al. 2007. Clin Chem Lab Med 45:1525-1530; Morris S M Jr. 2006. Am J Clin Nutr 83(Suppl):5985-5125; Rogers Q R. 1994. In Proceedings from a Symposium Honoring Willard J. Visek—from Ammonia to Cancer and Gene Expression. Special Publication 86—April, 1994, Agriculture Experiment Station, University of Illinois, 211 Mumford Hall, Urbana, Ill. 61801, pp. 9-21; Tapiero H, et al. 2002. Biomed Pharmacother 56:439-445, 2002; Viera Pinheiro J P, Boos J. 2004. Br J Haematol 125: 117-127; Wu G, et al. 2009. Amino Acids 37:153-168; Wu G, et al. 2004. J Nutr Biochem 15:442-451; Zeidan A, et al. 2008. Expert Opin Biol Ther 9:111-119).

BRIEF SUMMARY

Certain embodiments relate to an isolated arginine deiminase, wherein the isolated arginine deiminase has reduced cross-reactivity with patient anti-ADI-PEG 20 antibodies. Also included are therapeutic or pharmaceutical compositions comprising an isolated arginine deiminase or a fragment thereof having ADI activity, and a pharmaceutically-acceptable carrier. In certain embodiments, the composition is sterile and/or substantially free of pyrogens such as endotoxins. In some embodiments, the isolated arginine deiminase having reduced cross-reactivity with patient anti-ADI-PEG 20 antibodies is not from *M. hominis*. In some embodiments, the isolated arginine deiminase having reduced cross-reactivity with patient anti-ADI-PEG 20 antibodies is from an organism listed in Table 1.

In certain embodiments the isolated arginine deiminase having reduced cross-reactivity with patient anti-ADI-PEG 20 antibodies has one or more properties comparable to or better than those of ADI-PEG 20. In this regard, the one or more properties includes, but is not limited to, Kcat, Km, pH optimum, stability, in vivo proteolytic stability, or no requirement for ions or cofactors that are not already present in blood, or any combination thereof. In some embodiments, the isolated arginine deiminase having reduced cross-reactivity with patient anti-ADI-PEG 20 antibodies, has at least 5, 10, 15, or 20 surface residue changes as compared to *M. hominis* arginine deiminase. In certain embodiments, the isolated arginine deiminase having reduced cross-reactivity with patient anti-ADI-PEG 20 antibodies has between about 20 and 135 surface residue changes, between about 40 and 100 surface residue changes, between about 30 and 60 surface residue changes, between about 80 and 100 surface residues changes, or between about 100 and 120 surface residues changes, as compared to *M. hominis* arginine deiminase.

In certain embodiments, the isolated arginine deiminase having reduced cross-reactivity with patient anti-ADI-PEG 20 antibodies is from *Mycoplasma salivarium, Mycoplasma spumans, Mycoplasma canadense, Mycoplasma auris, Mycoplasma hyosynoviae, Mycoplasma cloacale, Mycoplasma anseris, Mycoplasma alkalescens, Mycoplasma orale, Mycoplasma iners, Mycoplasma meleagridis, Mycoplasma alvi, Mycoplasma penetrans, Mycoplasma gallinarum, Mycoplasma pirum, Mycoplasma primatum, Mycoplasma fermentans, Mycoplasma lipofaciens, Mycoplasma felifaucium, Mycoplasma imitans, Mycoplasma opalescens, Mycoplasma moatsii, Mycoplasma elephantis, Mycoplasma pneumoniae, Mycoplasma testudinis, Mycoplasma* sp. CAG: 877, or *Mycoplasma* sp. CAG:472. Illustrative arginine deiminase having reduced cross-reactivity with patient anti-ADI-PEG 20 antibodies comprise any one or more of the amino acid sequences set forth in SEQ ID NOs:2-28.

In some embodiments, the isolated arginine deiminase having reduced cross-reactivity with patient anti-ADI-PEG 20 antibodies has been modified to remove at least one pegylation site. In certain embodiments of the arginine deiminase having reduced cross-reactivity with patient anti-ADI-PEG 20 antibodies, at least one lysine residue has been modified by an amino acid substitution. In this regard, in certain embodiments, at least about 5 lysine residues, at least about 10 lysine residues, or at least about 20 lysine residues have been modified by an amino acid substitution.

In some embodiments, the arginine deiminase having reduced cross-reactivity with patient anti-ADI-PEG 20 antibodies is covalently bonded via a linker to a PEG molecule. In this regard, the arginine deiminase having reduced cross-reactivity with patient anti-ADI-PEG 20 antibodies may be covalently bonded to one or more PEG molecule, such as to about 1 to about 10 or about 2 to about 8 PEG molecules. The PEG molecules may be straight chain or branch chain PEG molecules and may have a total weight average molecular weight of from about 1,000 to about 40,000, or a total weight average molecular weight of from about 10,000 to about 30,000. In some embodiments, where the PEG is covalently bonded to an ADIr described herein via a linker, the linker may comprise a succinyl group, an amide group, an imide group, a carbamate group, an ester group, an epoxy group, a carboxyl group, a hydroxyl group, a carbohydrate, a tyrosine group, a cysteine group, a histidine group, a methylene group, or any combinations thereof. In specific embodiments, the source of the succinyl group is succinimidyl succinate.

Also included are polynucleotides encoding an isolated arginine deiminase described herein, vectors comprising the polynucleotide, and isolated host cells comprising the vectors.

Certain embodiments relate to compositions comprising an isolated arginine deiminase having reduced cross-reactivity with patient anti-ADI-PEG 20 antibodies as described herein, and a physiologically acceptable carrier. In certain embodiments, the compositions further comprise a chemotherapeutic agent. Exemplary chemotherapeutic agents include, but are not limited to, docetaxel, carboplatin, cyclophosphamide, gemcitabine, cisplatin, sorafenib, sunitinib, and everolimus.

Also included are methods of treating, ameliorating the symptoms of, or inhibiting the progression of a cancer comprising administering to a patient in need thereof a therapeutically effective amount of a composition comprising the isolated arginine deiminase having reduced cross-reactivity with patient anti-ADI-PEG 20 antibodies as described herein and a physiologically acceptable carrier, thereby treating, ameliorating the symptoms of, or inhibiting the progression of the cancer. In certain embodiments, the patient in need thereof has been determined to have anti-ADI-PEG 20 antibodies. In some embodiments, the cancer is selected from the group consisting of hepatocellular carcinoma, melanoma including metastatic melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer.

Some embodiments include methods of treating, ameliorating the symptoms of, or inhibiting the progression of a cancer comprising administering to a patient in need thereof a therapeutically effective amount of a composition comprising ADI-PEG 20, and after a period of time, administering to the patient a composition comprising the isolated arginine deiminase having reduced cross-reactivity with patient anti-ADI-PEG 20 antibodies as described herein and a physiologically acceptable carrier, thereby treating, ameliorating the symptoms of, or inhibiting the progression of the cancer. The period of time may be determined, for example, by detecting a predetermined level of anti-ADI-PEG 20 antibodies in the patient and/or measuring or otherwise observing ADI activity in the patient, wherein the composition comprising the isolated arginine deiminase having reduced cross-reactivity with patient anti-ADI-PEG 20 antibodies is administered following detection of the predetermined level of said anti-ADI-PEG 20 antibodies and/or measurement or observation of a predetermined level of ADI activity in the patient.

Also included are isolated arginine deiminase proteins described herein for use in the preparation or manufacture of a medicament for treating, ameliorating the symptoms of, or inhibiting the progression of a cancer.

BRIEF DESCRIPTION OF THE DRAWINGS

FIGS. 1A-1D illustrate a variety of cysteine-reactive PEG molecules that can be conjugated to the ADIr enzymes described herein.

DETAILED DESCRIPTION

Figure 1C:
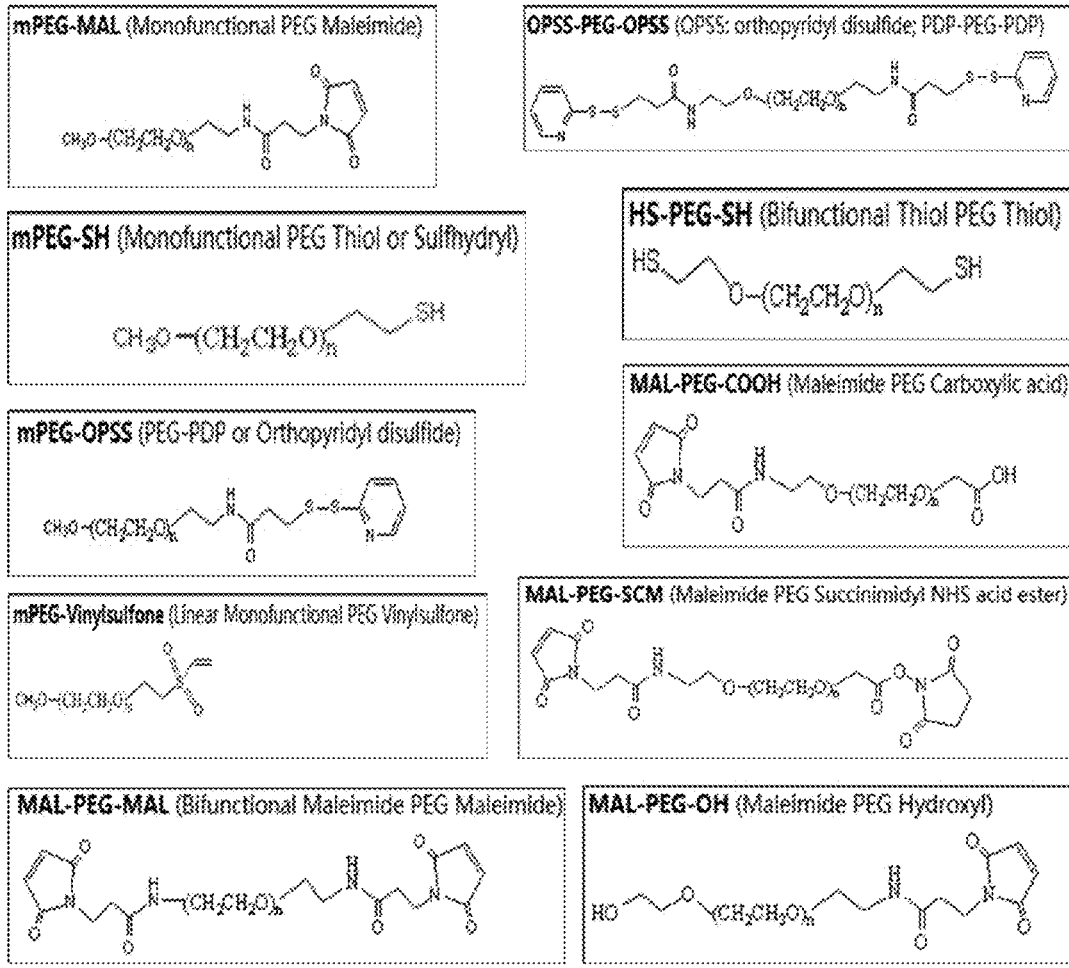
Figure 1C:
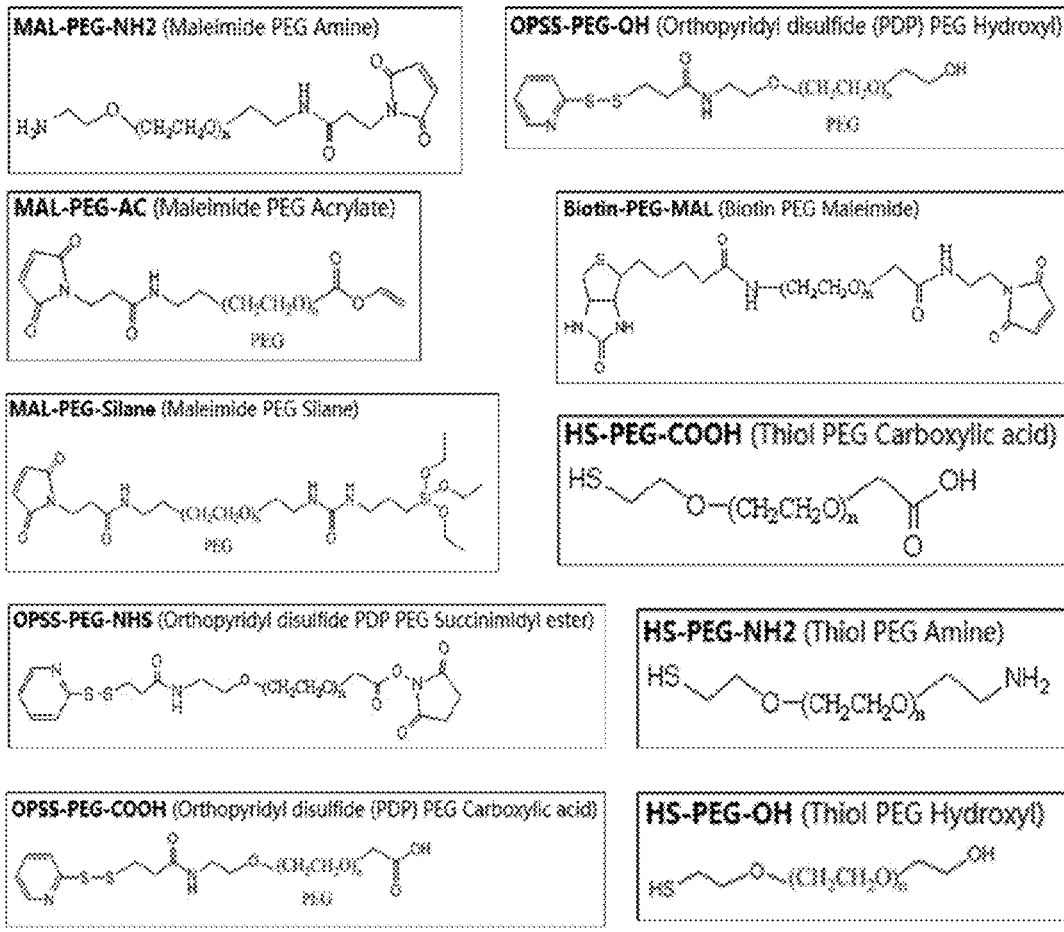
Figure 1C:
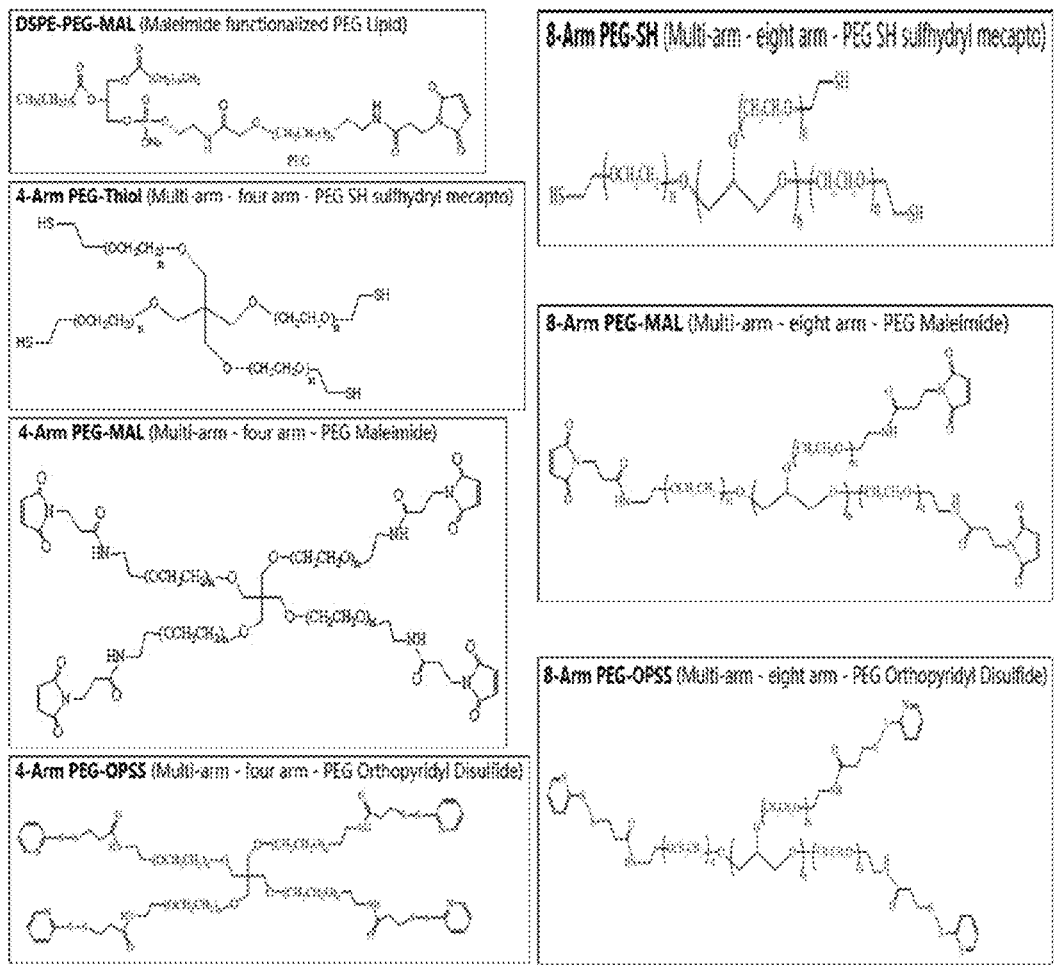

Embodiments of the present invention relate to selected ADI enzymes, which in some embodiments are conjugated with PEG through a linker, e.g., a stable linker. In some embodiments, the ADI enzymes are engineered or selected to have a small or otherwise reduced number of surface lysine residues, for example, relative to a wild-type sequence or a reference sequence (see, e.g., Table 1). The selected ADI enzymes are chosen from a large number of ADI enzymes, from different organisms, based on their beneficial properties. These properties include the ability of the enzyme to establish and maintain low arginine concentrations in human blood through ADI conversion of arginine to citrulline and ammonia. In some embodiments, the selected ADI molecules have reduced cross-reactivity toward anti-ADI-PEG 20 antibodies as compared to ADI-PEG 20, such antibodies possibly resulting from a patient's previous treatment with ADI-PEG 20.

In certain embodiments, the ADI enzymes are pegylated to provide protection against renal clearance and proteolysis, as well as reduced immunogenicity or antigenicity. To increase the effectiveness of the pegylation, modifications to the enzymes may be engineered to reduce the number of surface lysine residues and therefore limit the number of available PEG attachment sites. In some instances, reducing the number of lysine residues provides more complete and uniform pegylation at the remaining lysine attachment residues.

In some embodiments, the PEG linker selected to attach methoxy-PEG to ADI provides a chemically-stable linkage. It is expected that a stable linker will increase the molecule's bioactive lifetime. A chemically stable linker will also eliminate hydrolysis and reduce an immune response that might occur to a de-pegylated linker attached to the enzyme surface.

These cumulative specifications result in one or more molecules that effectively remove arginine from a patient's blood and are not neutralized or cleared by anti-ADI-PEG 20 antibodies from previous arginine depletion therapy. The molecules are pegylated so as to delay neutralization and clearance due to their own immunogenicity. These factors will permit their use instead of ADI-PEG 20 or in addition to ADI-PEG 20 (e.g., as a follow-on drug) to extend arginine depletion therapy and therefore increase effectiveness of arginine depletion treatment as an anti-cancer therapeutic.

Normal cells do not require arginine for growth, since they can synthesize arginine from citrulline in a two-step process catalyzed by ASS and ASL. In contrast, certain cancers do not express ASS. Certain cancers do not express ASL, and other cancers may have diminished expression of, or may not express ASS and/or ASL. Therefore, these cancers are auxotrophic for arginine. This metabolic difference may be capitalized upon to develop a safe and effective therapy to treat these forms of cancer. ADI catalyzes the conversion of arginine to citrulline via the arginine dihydrolase pathway, and may thus be used to eliminate arginine.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Protein Science, Current Protocols in Molecular Biology or Current Protocols in Immunology*, John Wiley & Sons, New York, N.Y. (2009); Ausubel et al., *Short Protocols in Molecular Biology*, 3rd ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

As used in this specification and the appended claims, the singular forms "a," "an" and "the" include plural references unless the content clearly dictates otherwise.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" includes both naturally-occurring and non-natural amino acids as well as amino acid analogs and mimetics. Naturally-occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-natural amino acids include, for example, norleucine, norvaline, p-fluorophenylalanine, ethionine, and the like, which are known to a person skilled in the art. Amino acid analogs include modified forms of natural and non-natural amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

"Biocompatible" refers to materials or compounds which are generally not injurious to biological functions and which will not result in any degree of unacceptable toxicity, including allergenic and disease states.

The terms "endotoxin free" and "substantially endotoxin free" relate generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art. Also included are methods of producing polypeptides in and isolating them from eukaryotic cells such as mammalian cells to reduce, if not eliminate, the risk of endotoxins being present in a composition of the invention. Included are methods of producing polypeptides in and isolating them from serum free cells.

Endotoxins can be detected using routine techniques known in the art. For example, the Limulus Amoebocyte Lysate assay, which utilizes blood from the horseshoe crab, is a highly sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/ml. Typically, 1 ng lipopolysaccharide (LPS) corresponds to about 1-10 EU.

The "half-life" of a polypeptide can refer to the time it takes for the polypeptide to lose half of its pharmacologic, physiologic, or other activity, relative to such activity at the time of administration into the serum or tissue of an organism, or relative to any other defined time-point. "Half-life" can also refer to the time it takes for the amount or concentration of a polypeptide to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

"Homology" refers to the percentage number of amino acids that are identical or constitute conservative substitutions. Homology may be determined using sequence comparison programs such as GAP (Deveraux et al., Nucleic Acids Research. 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and ranges in between e.g., 1.5, 1.6, 1.7. 1.8, etc.) the amount produced by no composition (e.g., the absence of agent) or a control composition. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) in the amount produced by no composition (e.g., the absence of an agent) or a control composition. Examples of comparisons and "statistically significant" amounts are described herein.

"Patient" or "subject" refers to an animal, in certain embodiments a mammal, and in specific embodiments, a human.

In certain embodiments, the "purity" of any given agent (e.g., ADIr, ADIr-PEG) in a composition may be specifically defined. For instance, certain compositions may comprise an agent that is at least 80, 85, 90, 91, 92, 93, 94, 95, 96, 97, 98, 99, or 100% pure, including all decimals and ranges in between, as measured, for example and by no means limiting, by high performance liquid chromatography (HPLC), a well-known form of column chromatography used frequently in biochemistry and analytical chemistry to separate, identify, and quantify compounds.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polypeptides include "reference sequence," "comparison window," "sequence identity," "percentage of sequence identity" and "substantial identity." A "reference sequence" can be at least 12 but frequently 15 to 18 and often at least 25 monomer units, inclusive of nucleotides and amino acid residues, in length. Because two polypeptides may each comprise (1) a sequence (i.e., only a portion of the complete polypeptides sequence) that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al. (Nucl. Acids Res. 25:3389, 1997). A detailed discussion of sequence analysis can be found in Unit 19.3 of Ausubel et al. ("Current Protocols in Molecular Biology," John Wiley & Sons Inc, 1994-1998, Chapter 15).

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch algorithm (J. Mol. Biol. 48: 444-453, 1970) which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In some embodiments, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. Another exemplary set of parameters (and the one that should be used unless otherwise specified) includes a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (Cabios. 4:11-17, 1989) which has been incorporated into the ALIGN program (version 2.0), using a PAM120 weight residue table, a gap length penalty of 12 and a gap penalty of 4.

The term "solubility" refers to the property of ADIr enzyme provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, pH 7.2, pH 7.4, pH 7.6, pH 7.8, or pH 8.0. In certain embodiments, solubility is measured in water or a physiological buffer such as PBS or NaCl (with or without NaP) or other buffer/composition described herein. In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an ADIr enzyme has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at 37° C.

"Substantially" or "essentially" means nearly totally or completely, for instance, 95%, 96%, 97%, 98%, 99% or greater of some given quantity.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

Each embodiment in this specification is to be applied mutatis mutandis to every other embodiment unless expressly stated otherwise.

Throughout the present disclosure, the following abbreviations may be used: PEG, polyethylene glycol; ADI, arginine deiminase; SS, succinimidyl succinate; SSA, succinimidyl succinimide; SPA, succinimidyl propionate; NHS, N-hydroxy-succinimide; ASS1 or ASS, argininosuccinate synthetase; ASL, argininosuccinate lyase.

A polynucleotide encoding an ADI enzyme may be derived, cloned, isolated, synthesized or produced from any source, including, for example, microorganisms, recombinant biotechnology or any combination thereof. For example, arginine deiminase may be cloned from microorganisms of the genera *Mycoplasma*. In certain embodiments, arginine deiminase is cloned from *Mycoplasma salivarium, Mycoplasma spumans, Mycoplasma canadense, Mycoplasma auris, Mycoplasma hyosynoviae, Mycoplasma cloacale, Mycoplasma anseris, Mycoplasma alkalescens, Mycoplasma orale, Mycoplasma iners, Mycoplasma meleagridis, Mycoplasma alvi, Mycoplasma penetrans, Mycoplasma gallinarum, Mycoplasma pirum, Mycoplasma primatum, Mycoplasma fermentans, Mycoplasma lipofaciens, Mycoplasma felifaucium, Mycoplasma imitans, Mycoplasma opalescens, Mycoplasma moatsii, Mycoplasma elephantis, Mycoplasma pneumoniae, Mycoplasma testudinis, Mycoplasma* sp. CAG:877, or *Mycoplasma* sp. CAG:472, or any combination thereof. In some embodiments, the arginine deiminase is cloned from a species listed in Table 1. In particular embodiments, the ADI comprises the amino acid sequence of any one of SEQ ID NOs: 2-28, or a variant or fragment or extension thereof having ADI activity (e.g., able to metabolize arginine into citrulline and ammonia). Such ADI enzymes can be prepared or synthesized using known techniques.

In certain embodiments, the ADI enzymes as described herein are compared to the benchmark ADI-PEG 20 molecule derived from *M. hominis*. As used herein, "ADI-PEG 20" refers to the ADI molecule known in the art and described for example in U.S. Pat. Nos. 6,183,738 and 6,635,462; see also Ascierto et al., 2005. Pegylated arginine deiminase treatment of patients with metastatic melanoma: results from phase I and II studies. J Clin Oncol 23(30): 7660-7668; Izzo F, et al. (2004) Pegylated arginine deiminase treatment of patients with unresectable hepatocellular carcinoma: results from phase I/II studies. J Clin Oncol 22(10): 1815-1822; Holtsberg F W, et al. (2002), Poly (ethylene glycol) (PEG) conjugated arginine deiminase: effects of PEG formulations on its pharmacological properties. J Control Release 80(1-3): 259-271; Kelly et al., (2012) British Journal of Cancer 106, 324-332. As would be recognized by the skilled artisan, this molecule is a pegylated (PEG 20,000) ADI enzyme derived from *M. hominis*, and has two substitutions (K112E; P210S) relative to the wild type *M. hominis* ADI enzyme.

The arginine deiminase enzymes as described herein are screened from a large number of ADI enzymes and are believed to have reduced level of reactivity with anti-ADI-PEG 20 antibodies from patients and/or other beneficial properties. Anti-ADI-PEG 20 antibodies can appear in subjects treated with ADI-PEG 20 and can be measured using known methodologies. Reactivity to anti-ADI-PEG 20 antibodies can be determined for example using ELISA or other similar assays known to the skilled artisan.

In this regard, ADI-PEG 20 can be used as a comparison to assess cross-reactivity level to patient anti-ADI-PEG 20 antibodies. A cross-reactivity level that is statistically significantly lower than that of ADI-PEG 20 to patient anti-ADI-PEG 20 antibodies may be useful herein. In certain embodiments, the arginine deiminase enzymes as described herein have low or no cross-reactivity to anti-ADI-PEG 20 antibodies. In certain embodiments, any reduction in reactivity to anti-ADI-PEG 20 antibodies as compared to reactivity with ADI-PEG 20 can be beneficial as such an ADI enzyme would improve treatment options for patients in need of arginine depletion therapy. Thus, in some embodiments, the arginine deiminase enzymes as described herein have reduced cross-reactivity to patient anti-ADI-PEG 20 antibodies as compared to ADI-PEG 20 reactivity to such antibodies.

"ADIr" is used herein to refer to an ADI enzyme of the present invention having reduced cross-reactivity to anti-ADI-PEG 20 antibodies as compared to ADI-PEG 20 reactivity to such antibodies. "ADIr" nomenclature is used to distinguish the molecules identified herein from ADI and ADI-PEG 20 as known in the art. Examples of ADIr enzymes include SEQ ID NOS:2-28, and variants thereof that differ in amino acid sequence from SEQ ID NO:1 or ADI-PEG 20.

In some embodiments, the ADIr enzymes of the invention have characteristics or properties comparable to or better than those of ADI-PEG 20, in order to reduce and maintain low blood arginine levels for effective cancer treatment. Examples of such properties include Kcat, Km, pH optimum, stability, in vivo proteolytic stability and lack of requirement for ions or cofactors not already present in the blood, or any combination thereof. In certain embodiments, an ADIr as described herein has properties that are about or at least 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or higher, than comparable properties of ADI-PEG 20. In some embodiments an ADIr described herein has properties that are about or at least about 100%, 105%, 110%, 120%, 140%, 150%, 160%, 180%, 200%, 220%, 240%, 250%, 260%, 280%, 300%, 320%, 340, 350%, 360%, 400%, 420%, 450%, 460%, 500%, 520%, 550% or higher than the specific property of ADI-PEG 20 being compared.

Thus, in certain embodiments, an ADIr has a Kcat that is about or at least about 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% of the Kcat of ADI-PEG 20, or better. In certain embodiments, an ADIr has a Kcat that is about or at least about 100%, 105%, 110%, 120%, 125%, 140%, 150%, 160%, 180%, 200%, 220%, 240%, 250%, 260%, 280%, 300%, 320%, 340, 350%, 360%, 400%, 420%, 450%, 460%, 500%, 520%, 550% or higher, times that of the ADI-PEG 20 Kcat. In certain embodiments, the Kcat of the ADIr enzymes described herein, or compositions comprising same, is about 0.5 $sec^{-1}$ to about 15 $sec^{-1}$, about 1 $sec^{-1}$ to about 12 $sec^{-1}$, about 1 $sec^{-1}$ to about 10 $sec^{-1}$, about 1.5 $sec^{-1}$ to about 9 $sec^{-1}$, about 2 $sec^{-1}$ to about 8 $sec^{-1}$ or about 2.5 $sec^{-1}$ to about 7 $sec^{-1}$. In certain embodiments, the ADIr or ADIr-PEG in a composition has a Kcat of about 2.5 $sec^{-1}$ to about 7.5 $sec^{-1}$. In some embodiments, the ADIr or ADIr-PEG in a composition has a Kcat of about 2.5 $sec^{-1}$, about 3 $sec^{-1}$, about 3.5 $sec^{-1}$, about 4 $sec^{-1}$, about 4.5 $sec^{-1}$, about 5 $sec^{-1}$, about 5.5 $sec^{-1}$, about 6 $sec^{-1}$, about 6.5 $sec^{-1}$, about 7 $sec^{-1}$, about 7.2 $sec^{-1}$, about 7.5 $sec^{-1}$, about 8 $sec^{-1}$, about 10 $sec^{-1}$, about 15 $sec^{-1}$, about 20 $sec^{-1}$, about 25 $sec^{-1}$, about 30 $sec^{-1}$, about 35 $sec^{-1}$, about 40 $sec^{-1}$, about 45 $sec^{-1}$, about 50 $sec^{-1}$, about 55 $sec^{-1}$, about 60 $sec^{-1}$, about 65 $sec^{-1}$, about 70 $sec^{-1}$, about 75 $sec^{-1}$, about 80 $sec^{-1}$, about 85 $sec^{-1}$, about 90 $sec^{-1}$, about 95 $sec^{-1}$, or about 100 $sec^{-1}$.

In certain embodiments, an ADIr has a Km that is about or at least about 5%, 6%, 7%, 8%, 9%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% of the Km of ADI-PEG 20, or better. In certain embodiments, an ADIr has a Km that is about or at least about 100%, 105%, 110%, 120%, 130%, 140%, 150%, 160%, 180%, 200%, 220%, 240%, or 250% that of the Km of ADI-PEG 20. In particular embodiments, an ADIr, or a pegylated formulation thereof, has a Km of from about 0.5 µM to about 50 µM, or about 1.6 µM to about 48 µM, or about 0.5 µM to about 15 µM, from about 1 µM to about 12 µM, about 1 µM to about 10 µM, about 1.5 µM to about 9 µM, about 1.5 µM to about 8 µM, or about 1.5 µM to about 7 µM. In certain embodiments, the ADIr or ADIr-PEG in a composition has a Km of about 1.5 µM to about 6.5 µM. In some embodiments, the ADIr or pegylated formulation thereof has a Km of about 1.5 µM, about 1.6 µM, about 2 µM, about 2.5 µM, about 3 µM, about 3.5 µM, about 4 µM, about 4.5 µM, about 5 µM, about 5.5 µM, about 6 µM, about 6.5 µM, about 7 µM, about 8 µM, about 9 µM, about 10 µM, about 12 µM, about 14 µM, about 15 µM, about 16 µM, about 18 µM about 20 µM, about 22 µM, about 24 µM, about 25 µM, about 26 µM, about 28 µM, about 30 µM, about 32 µM, about 34 µM, about 35 µM, about 36 µM, about 38 µM, about 40 µM, about 42 µM, about 44 µM, about 45 µM, about 46 µM, about 48 µM, or about 50 µM.

In certain embodiments, an ADIr functions at a pH close to the physiological pH of human blood. Thus, in some embodiments, an ADIr functions at a pH of about 4 to about 10.8, or about 6 to about 8, or about 6.5 to about 7.5. In certain embodiments, an ADIr has good enzyme activity at about pH 7.4.

In certain embodiments, an ADIr has stability during long term storage and temperature and proteolytic stability during treatment in the human body. In some embodiments, an ADIr does not require ions or cofactors for activity that are not already present in blood.

In certain embodiments, an ADIr described herein generally has an amino acid sequence sufficiently different from M. hominis so that there are surface residue changes which will reduce or eliminate antigenic sites for anti-ADI-PEG 20 antibodies. In some embodiments, there will be no cross reactivity (e.g., no statistically significant cross-reactivity) between the selected ADIr molecule and existing anti-ADI-PEG 20 antibodies in a subject, and a completely new immune response will be generated in a subject rather than a maturation of the existing response to *M. hominis* ADI. Thus, in some embodiments, an ADIr as described herein has from 20%-85% sequence identity to *M. hominis* ADI as set forth in SEQ ID NO:1. In certain embodiments, an ADIr as described herein has even lower percent sequence identity to *M. hominis* ADI, such as 10% or 15% identity. In certain embodiments, an ADIr as described herein has 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82% or even 83% identity to *M. hominis* ADI, and still has reduced cross-reactivity toward anti-ADI-PEG 20 antibodies.

In certain embodiments, an ADIr as described herein has from about 10-140, 15-140, or 25-140 surface residue changes as compared to *M. hominis* ADI. Surface residues can be identified from the crystal structure of *M. hominis* ADI and surface residues for ADI from other organisms can be determined by sequence homology. An ADIr as described herein may have about 10, 15, 20, 25, 30, 35, 40, 45, 50, 55, 60, 65, 70, 75, 80, 85, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or about 140 surface residue changes as compared to *M. hominis* ADI (see SEQ ID NO:1).

In some embodiments, an ADIr as described herein has from about 10-140, 15-140, or 25-140 residue changes as compared to *M. hominis* ADI. Such residue changes need not only be of surface amino acid residues. Such residue changes (or additions or deletions) can be at either end of the molecule or may be at any residue of the ADI, such that the modified ADI has the desired ADI activity as described herein. Residues to be changed can be identified from the crystal structure of *M. hominis* ADI and residues for ADI from other organisms can be determined by sequence homology. An ADIr as described herein may have about 10, 15, 20, 25, 30, 35, 40, 45, 50, 55, 60, 65, 70, 75, 80, 85, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or about 140 amino acid residue changes as compared to *M. hominis* ADI (see SEQ ID NO:1).

From a large number of ADI enzymes, Table 1 lists 27 ADIr enzymes and their percent sequence identity relative to *M. hominis* ADI.

In certain embodiments, the ADIr enzymes identified herein from a number of selected species, have a defined number of surface lysine residues (in certain embodiments, e.g., up to 30 or more). Certain of the ADIr enzymes identified herein that have reduced cross-reactivity with anti-ADI-PEG 20 antibodies have about, at least about, or no more than about 0, 1, 2, 3, 4, 5, 10, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 surface lysine residues, including all ranges in between.

The terms "polypeptide," "protein" and "peptide" are used interchangeably and mean a polymer of amino acids not limited to any particular length. The term "enzyme" includes polypeptide or protein catalysts, and with respect to ADIr is used interchangeably with protein, polypeptide, or peptide. The terms include modifications such as myristoylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the ADIr enzymes/proteins described herein, or sequences that have deletions from, additions to, and/or substitutions of one or more amino acid of the ADIr proteins. In certain embodiments, the polypeptide is a "recombinant" polypeptide, produced by recombinant cell that comprises one or more recombinant DNA molecules, which are typically made of heterologous polynucleotide sequences or combinations of polynucleotide sequences that would not otherwise be found in the cell.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or non-covalent interaction) with portions of a protein with which the "isolated protein" is associated in nature, (6) is operably associated (by covalent or non-covalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "variant" includes a polypeptide that differs from a reference polypeptide specifically disclosed herein (e.g., SEQ ID NOS:1-28) by one or more substitutions, deletions, additions and/or insertions. Variant polypeptides are biologically active, that is, they continue to possess the enzymatic or binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides described herein and still obtain a functional molecule that encodes a variant or derivative polypeptide with desirable characteristics.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native sequence by substitution, deletion or addition of fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In general, variants will display about or at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence (e.g., SEQ ID NOS:1-28).

Moreover, sequences differing from the native or parent sequences by the addition (e.g., C-terminal addition, N-terminal addition, both), deletion, truncation, insertion, or substitution of about 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the properties or activities of a parent or reference polypeptide sequence are contemplated.

In some embodiments, variant polypeptides differ from reference sequence by at least one but by less than 50, 40, 30, 20, 15, 10, 8, 6, 5, 4, 3 or 2 amino acid residue(s). In some embodiments, variant polypeptides differ from a reference sequence by about or at least 0.5% or 1% but less than 20%, 15%, 10% or 5% of the residues. (If this comparison requires alignment, the sequences should be aligned for maximum similarity. "Looped" out sequences from deletions or insertions, or mismatches, are considered differences.).

In some embodiments, an ADIr will be about 300 to about 500 amino acids in length, including all integers and ranges in between. In specific embodiments, the ADIr will be about 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 amino acids in length, including all integers and ranges in between.

The term "polypeptide fragment" refers to a polypeptide that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 400 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, or 400 amino acids long. Particularly useful polypeptide fragments include functional domains, including the catalytic ADI domains of the ADIr described herein. In the case of an ADIr, useful fragments include, but are not limited to, the catalytic domain and the α-helical domain.

Many activated PEGs used for conjugation to ADI covalently bond to lysine residues. There are usually many fewer PEG molecules attached to ADI than there are lysine residues. Both the number and distribution of attachments can be heterogeneous from molecule to molecule. Any particular lysine residue will be modified in only a small fraction of the ADI molecules. This site modification heterogeneity and low PEG occupancy can result in problems with both drug characterization and the effectiveness of PEG shielding at antigenic sites. Therefore, in certain embodiments, the selected ADIr enzymes as described herein, are modified by lysine replacement with other residue types to reduce the number of lysine residues. This produces a more uniformly pegylated protein and increases the PEG occupancy at the remaining lysine residues. Specific lysine residues chosen to be changed to other residues will be selected in order to preserve enzyme activity. This more uniform pegylation is expected to provide increased protection against proteolysis in blood and increased shielding of antigenic sites from patient antibodies.

In certain embodiments, the ADIr enzyme is modified as described in U.S. Pat. No. 6,635,462. In particular, modifications of one or more of the naturally-occurring amino acid residues of an ADIr can provide for an enzyme that is more easily renatured and formulated thereby improving the manufacture of ADIr and therapeutic compositions comprising the same. In some embodiments, the ADIr enzyme is modified to remove one or more lysine residues (e.g., the lysine can be substituted with another amino acid or analogues thereof, or a non-natural amino acid). In particular, in some embodiments, the ADIr enzyme is modified to be free of the lysine at a position equivalent to 112, 374, 405 or 408 of SEQ ID NO:1 (M. hominis ADI), or a combination of one or more of these positions. In some embodiments, the ADIr enzyme is modified to be free of one or more lysine residues, for example, 1, 2, 3, 4, 5, 6, 7, 8, 9, 10, 11, 12, 13, 14, 15, 16, 17, 18, 19, 20, 21, or more lysine residues, should they be present, can be substituted with another amino acid or analogues thereof, or a non-natural amino acid. In specific embodiments, an ADIr enzyme has 5 lysine residues substituted, for example, at an equivalent position to position 7, 88, 137, 209, and 380 of SEQ ID NO: 1. In some embodiments, an ADIr enzyme has 10 lysine residues substituted, for example, at positions equivalent to positions 7, 9, 59, 88, 115, 116, 137, 178, 209, and 380 of SEQ ID NO: 1. In certain embodiments, an ADIr enzyme has 15 lysine residues substituted, for example, at positions equivalent to positions 7, 9, 59, 66, 88, 91, 93, 115, 116, 137, 141, 178, 209, 279, and at position 380 of SEQ ID NO: 1. In some embodiments, an ADIr enzyme has 21 lysine residues substituted, for example, at positions equivalent to positions 7, 9, 56, 59, 66, 88, 91, 93, 96, 115, 116, 137, 141, 178, 209, 254, 279, 325, 326, 380, and 406 of SEQ ID NO: 1.

In some instances, a native ADIr may be found in microorganisms and is thus immunogenic and rapidly cleared from circulation in a patient. These problems may be overcome by modifying an ADIr to create a "modified ADIr" enzyme. Thus, certain embodiments include an ADIr enzyme that comprises a "modifying agent," examples of which included but are not limited to macromolecule polymers, proteins, peptides, polysaccharides, and other compounds. The ADIr enzyme and the modifying agent may be linked by either covalent bonds or non-covalent interaction to form a stable conjugate or a stable composition to achieve a desired effect. In certain embodiments, the modified ADIr retains the biological activity of a corresponding unmodified ADIr (e.g., of the same or similar sequence) and has a longer half-life in vivo and lower antigenicity than the corresponding unmodified ADIr. In certain embodiments, the modified ADIr retains at least 30%, 35%, 40%, 45%, 50%, 55%, 60%, 65%, 70%, 75%, 80%, 85%, 90%, 95%, 96%, 97%, 98%, 99% or more of the biological activity of the corresponding unmodified ADIr. Generally, the modified ADIr retains biological activity sufficient for therapeutic use.

In some embodiments, a modifying agent can be a polymer or a protein or a fragment thereof that is biocompatible and can increase the half-life of ADIr in blood. The modifying agent can be either chemically coupled to ADIr or where applicable, linked to the ADIr via fusion protein expression.

Macromolecule polymers may include a non-peptide macromolecule polymer, which in certain embodiments, may have its own bioactivity. Suitable polymers include, but are not limited to, polyenol compounds, polyether compounds, polyvinylpyrrolidone, poly amino acids, copolymer of divinyl ether and maleic anhydride, N-(2-hydroxypropyl)-methacrylamide, polysaccharide, polyoxyethylated polyol, heparin or its fragment, poly-alkyl-ethylene glycol and its derivatives, copolymers of poly-alkyl-ethylene glycol and its derivatives, poly(vinyl ethyl ether), a,P-Poly[(2-hydroxyethyl)-DL-aspartamide], polycarboxylates, poly oxyethylene-oxymethylenes, polyacryloyl morpholines, copolymer of amino compounds and oxyolefin, poly hyaluronic acid, polyoxiranes, copolymer of ethanedioic acid and malonic acid, poly (1,3-dioxolane), ethylene and maleic hydrazide copolymer, poly sialic acid, cyclodextrin, etc. In certain embodiments, the polymer is polyethylene glycol.

The polyenol compounds as used herein include, but are not limited to, polyethylene glycol (including monomethoxy polyethylene glycol, monohydroxyl polyethylene glycol), polyvinyl alcohol, polyallyl alcohol, polybutenol and the like, and their derivatives, such as lipids.

The polyether compounds include, but are not limited to poly alkylene glycol $(HO((CH2)_xO)_nH)$, polypropylene glycol, polyoxyrehylene $(HO((CH_2)_2O)_nH)$, polyvinyl alcohol $((CH_2CHOH)_n)$.

Poly amino acids include, but are not limited to, polymers of one type of amino acid or copolymers of two or more types of amino acids, for example, polyalanine or polylysine, or block co-polymers thereof.

Polysaccharides include but are not limited to, glucosan and its derivatives, for example dextran sulfate, cellulose and its derivatives (including methyl cellulose and carboxymethyl cellulose), starch and its derivatives, polysucrose, etc.

In specific embodiments, the ADIr is modified by coupling with protein(s) or peptide(s), wherein one or more proteins or peptides are directly or indirectly linked to ADIr. The proteins can either be naturally-existing proteins or their fragments, including but not limited to naturally existing human serum proteins or their fragments, such as thyroxine-binding protein, transthyretin, a1-acid glycoprotein, transferrin, fibrinogen, immunoglobulin, Ig Fc regions, albumin, and fragments thereof. By "fragment" is meant any portion of a protein that is smaller than the whole protein but which retains the desired function of the protein. The ADIr as described herein may be directly or indirectly linked to a protein via a covalent bond. Direct linking means that one amino acid of ADIr is directly linked to one amino acid of the modifying protein, via a peptide bond or a disulfide bridge. Indirect linking refers to the linkages between a ADIr and a modifying protein, via originally existing chemical groups there between or specific chemical groups added through biological or chemical means, or the combination of the above-mentioned linkages.

In particular embodiments, the ADIr is modified by covalent attachment to one or more PEG molecules. ADIr covalently modified with PEG (with or without a linker) may be hereinafter referred to as "ADIr-PEG." When compared to unmodified ADIr, ADIr-PEG retains most of its enzymatic activity, is far less immunogenic or antigenic, has a greatly extended circulating half-life, and is more efficacious in the treatment of tumors.

"Polyethylene glycol" or "PEG" refers to mixtures of condensation polymers of ethylene oxide and water, in a branched or straight chain, represented by the general formula $H(OCH_2CH_2)_nOH$, wherein n is at least 4. "Polyethylene glycol" or "PEG" is used in combination with a numeric suffix to indicate the approximate weight average molecular weight thereof. For example, PEG5,000 refers to PEG having a total weight average molecular weight of about 5,000; PEG12,000 refers to PEG having a total weight average molecular weight of about 12,000; and PEG20,000 refers to PEG having a total weight average molecular weight of about 20,000.

In some embodiments, the PEG has a total weight average molecular weight of about 1,000 to about 50,000; about 3,000 to about 40,000; about 5,000 to about 30,000; about 8,000 to about 30,000; about 11,000 to about 30,000; about 12,000 to about 28,000; about 16,000 to about 24,000; about 18,000 to about 22,000; or about 19,000 to about 21,000. In some embodiments, the PEG has a total weight average molecular weight of about 1,000 to about 50,000; about 3,000 to about 30,000; about 3,000 to about 20,000; about 4,000 to about 12,000; about 4,000 to about 10,000; about 4,000 to about 8,000; about 4,000 to about 6,000; or about 5,000. In specific embodiments, the PEG has a total weight average molecular weight of about 20,000. Generally, PEG with a molecular weight of 30,000 or more is difficult to dissolve, and yields of the formulated product may be reduced. The PEG may be a branched or straight chain. Generally, increasing the molecular weight of the PEG decreases the immunogenicity of the ADIr. The PEG may be a branched or straight chain, and in certain embodiments is a straight chain. The PEG having a molecular weight described herein may be used in conjunction with ADIr, and optionally, a biocompatible linker, to treat graft versus host disease (GVHD) or cancer, including, for example, hepatocellular carcinoma, acute myeloid leukemia, such as relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, stomach cancer, or esophageal cancer, among other cancers described herein.

Certain embodiments employ thiol, sulfhydryl, or cysteine-reactive PEG(s). In some embodiments, the thiol, sulfhydryl, or cysteine-reactive PEG(s) are attached to one or more naturally-occurring cysteine residues, one or more introduced cysteine residues (e.g., substitution of one or more wild-type residues with cysteine residue(s)), insertion of one or more cysteine residues), or any combination thereof (see, e.g., Doherty et al., Bioconjug Chem. 16:1291-98, 2005). In certain embodiments, certain of the wild-type ADI cysteines residues may be first substituted with another amino acid to prevent attachment of the PEG polymer to wild-type cysteines, for example, to prevent the PEG(s) from disrupting an otherwise desirable biological activity. Some embodiments employ one or more non-natural cysteine derivatives (e.g., homocysteine) instead of cysteine.

Figure 1D:
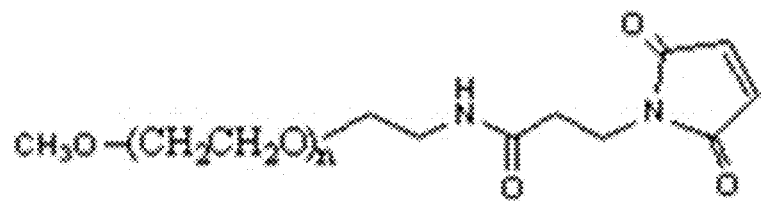

Non-limiting examples of thiol, sulfhydryl, or cysteine-reactive PEGs include Methoxy PEG Maleimides (M-PEG-MAL) (e.g., MW 2000, MW 5000, MW 10000, MW 20000, MW 30000, MW 40000). M-PEG-MALs react with the thiol groups on cysteine side chains in proteins and peptides to generate a stable 3-thiosuccinimidyl ether linkage. This reaction is highly selective and can take place under mild conditions at about pH 5.0-6.5 in the presence of other functional groups. Particular examples of commercially-available thiol, sulfhydryl, or cysteine-reactive PEG molecules are illustrated in FIGS. 1A-1D. Thus, in certain embodiments, an ADIr enzyme is conjugated to any one or more of the thiol, sulfhydryl, or cysteine-reactive PEG molecules described herein.

ADIr may be covalently bonded to a modifying agent, such as PEG, with or without a linker, although a preferred embodiment utilizes a linker. ADIr may be covalently bonded to PEG via a biocompatible linker using methods known in the art, as described, for example, by Park et al, Anticancer Res., 1:373-376 (1981); and Zaplipsky and Lee, Polyethylene Glycol Chemistry: Biotechnical and Biomedical Applications, J. M. Harris, ed., Plenum Press, NY, Chapter 21 (1992), the disclosures of which are hereby incorporated by reference herein in their entirety. In some instances, ADIr may be coupled directly (i.e., without a linker) to a modifying agent such as PEG, for example, through an amino group, a sulfhydryl group, a hydroxyl group, a carboxyl group, or other group.

The linker used to covalently attach ADIr to a modifying agent (e.g. PEG) can be any biocompatible linker. As discussed above, "biocompatible" indicates that the compound or group is non-toxic and may be utilized in vitro or in vivo without causing injury, sickness, disease, or death. A modifying agent such as PEG can be bonded to the linker, for example, via an ether bond, a thiol bond, an amide bond, or other bond.

In some embodiments, suitable linkers can have an overall chain length of about 1-100 atoms, 1-80 atoms, 1-60 atoms, 1-40 atoms, 1-30 atoms, 1-20 atoms, or 1, 2, 3, 4, 5, 6, 7, 8, 9, 10, 11, 12, 13, 14, 15, 16, 17, 18, 19, or 20 atoms, for example, wherein the atoms in the chain comprise C, S, N, P, and/or O. In certain embodiments, a linker is optional, e.g., a PEG conjugated ADIr enzyme does not comprise a linker. In some instances, a linker group includes, for example, a succinyl group, an amide group, an imide group, a carbamate group, an ester group, an epoxy group, a carboxyl group, a hydroxyl group, a carbohydrate, a tyrosine group, a cysteine group, a histidine group, a methylene group, and combinations thereof. Particular examples of stable linkers include succinimide, propionic acid, carboxymethylate linkages, ethers, carbamates, amides, amines, carbamides, imides, aliphatic C—C bonds, and thio ethers. In certain embodiments, the biocompatible linker is a succinimidyl succinate (SS) group.

Other suitable linkers include an oxycarbonylimidazole group (including, for example, carbonylimidazole (CDI)), a nitro phenyl group (including, for example, nitrophenyl carbonate (NCP) or trichlorophenyl carbonate (TCP)), a trysylate group, an aldehyde group, an isocyanate group, a vinylsulfone group, or a primary amine. In certain embodiments, the linker is derived from SS, SPA, SCM, or NHS; in certain embodiments, SS, SPA, or NHS are used, and in some embodiments, SS or SPA are used. Thus, in certain embodiments, potential linkers can be formed from methoxy-PEG succinimidyl succinate (SS), methoxy-PEG succinimidyl glutarate (SG), methoxy-PEG succinimidyl carbonate (SC), methoxy-PEG succinimidyl carboxymethyl ester (SCM), methoxy-PEG2 N-hydroxy succinimide (NHS), methoxy-PEG succinimidyl butanoate (SBA), methoxy-PEG succinimidyl propionate (SPA), methoxy-PEG succinimidyl glutaramide, and/or methoxy-PEG succinimidyl succinimide.

Additional examples of linkers include, but are not limited to, one or more of the following: —O—, —NH—, —S—, —C(O)—, C(O)—NH, NH—C(O)—NH, O—C(O)—NH, —C(S)—, —CH2-, —CH2-CH2-, —CH2-CH2-CH2-, —CH2-CH2-CH2-CH2-, —O—CH2-, —CH2-O—, —O—CH2-CH2-, —CH2-O—CH2-, —CH2-CH2-O—, —O—CH2-CH2-CH2-, —CH2-O—CH2-CH2-, —CH2-CH2-O—CH2-, —CH2-CH2-CH2-O—, —O—CH2-CH2-, —CH2-O—CH2-CH2-CH2-, —CH2-CH2-O—CH2-CH2-CH2-, —CH2-CH2-CH2-O—CH2-CH2-, —CH2-CH2-CH2-O—CH2-, —CH2-CH2-CH2-CH2-O—, —C(O)—NH—CH2-, —C(O)—NH—CH2-CH2-, —CH2-C(O)—NH—CH2-, —CH2-CH2-C(O)—NH—, —C(O)—NH—CH2-CH2-CH2-, —CH2-C(O)—NH—CH2-CH2-, —CH2-CH2-C(O)—NH—CH2-, —CH2-CH2-CH2-C(O)—NH—, —C(O)—NH—CH2-CH2-CH2-CH2-, —CH2-C(O)—NH—CH2-CH2-CH2-, —CH2-CH2-C(O)—NH—CH2-CH2-, —CH2-CH2-CH2-C(O)—NH—CH2-, —CH2-CH2-CH2-CH2-C(O)—NH—, —NH—C(O)—CH2-, —CH2-NH—C(O)—CH2-, —CH2-CH2-NH—C(O)—CH2-, —NH—C(O)—CH2-CH2-, —CH2-NH—C(O)—CH2-CH2, —CH2-CH2-NH—C(O)—CH2-CH2, —C(O)—NH—CH2-, —C(O)—NH—CH2-CH2-, —O—C(O)—NH—CH2-, —O—C(O)—NH—CH2-CH2-, —NH—CH2-, —NH—CH2-CH2-, —CH2-N H—CH2-, —CH2-CH2-NH—CH2-, —C(O)—CH2-, —C(O)—CH2-CH2-, —CH2-C(O)—CH2-, —CH2-CH2-C(O)—CH2-, —CH2-CH2-C(O)—CH2-CH2-, —CH2-CH2-C(O)—, —CH2-CH2-CH2-C(O)—NH—CH2-CH2-NH—, —CH2-CH2-CH2-C(O)—NH—CH2-CH2-NH—C(O)—, —CH2-CH2-CH2-C(O)—NH—CH2-CH2-NH—C(O)—CH2-, bivalent cycloalkyl group, —N(R6)-, R6 is H or an organic radical selected from the group consisting of alkyl, substituted alkyl, alkenyl, substituted alkenyl, alkynyl, substituted alkynyl, aryl and substituted aryl. Additionally, any of the linker moieties described herein may further include an ethylene oxide oligomer chain comprising 1 to 20 ethylene oxide monomer units [i.e., —(CH$_2$CH$_2$O)$_{1-20}$-]. That is, the ethylene oxide oligomer chain can occur before or after the linker, and optionally in between any two atoms of a linker moiety comprised of two or more atoms. Also, the oligomer chain would not be considered part of the linker moiety if the oligomer is adjacent to a polymer segment and merely represent an extension of the polymer segment.

Specific exemplary PEG molecules and linkers are described in Table A below.

TABLE A

PEG and Linkers

| PEG | Linker | Comments |
|---|---|---|
| Methoxy-PEG succinimidyl hexanoate | amide | pH 7-8, lower reactivity |
| Methoxy-PEG succinimidyl butanoate (SBA) | amide | pH 7-8, longer hydrolysis time than SPA (~23 min) |
| Methoxy-PEG succinimidyl propionate (SPA) | amide | Tan, 1998, Metase; Basu, IFN; Games, Phe Am. Lyase; better than SCM (~16 min) |
| Methoxy-PEG succinimidyl carboxymethyl ester (SCM) | amide | pH 7-8, RT, 1 hr rxn time, extremely reactive, 0.75 min at pH 8, 25° C., arginase |
| Methoxy-PEG succinimidyl glutaramide | amide | pH 7-8, RT, 90% complete |
| Methoxy-PEG succinimidyl succinamide | amide | pH 7-8, RT, 95% complete |
| MethoxyPEG2 NHS | | Gamez, Phe Am. Lyase; Basu, IFNa2a40K, Nulasta (G-CSF), pegfilgrastim (G-CSF) |
| Methoxy-PEG succinimidyl carbonate (SC) | urethane | Hydrolysis ½ longer than SCM, Wang, 2006, M. art. ADI, Basu, IFNa2b, slow release |
| Methoxy-PEG succinimidyl glutarate (SG) | ester | Yang, 2004, Metase |
| Methoxy-PEG succinimidyl succinate (SS) | ester | Adenosine deaminase, asparginase, ADI-PEG 20 |
| PEG-maleimide | | |
| PEG-vinylsulfone | | |
| PEG-iodoacetamide | | |
| orthopyridyl disulfide-PEG | | |

In certain embodiments, the ADIr enzyme comprises one or more PEG molecules and/or linkers as described herein (e.g., in Table A).

The attachment of PEG to ADIr increases the circulating half-life of ADIr. Generally, PEG is attached to a primary amine of ADIr. Selection of the attachment site of PEG, or other modifying agent, on the ADIr is determined by the role of each of the sites within the active domain of the protein, as would be known to the skilled artisan. PEG may be attached to the primary amines of ADIr without substantial loss of enzymatic activity. For example, the lysine residues present in ADIr are all possible points at which ADIr as described herein can be attached to PEG via a biocompatible linker, such as SS, SPA, SCM, SSA and/or NHS. PEG may also be attached to other sites on ADIr, as would be apparent to one skilled in the art in view of the present disclosure.

From 1 to about 30 PEG molecules may be covalently bonded to ADIr. In certain embodiments, ADIr is modified with (i.e., comprises) one PEG molecule. In some embodiments, the ADIr is modified with more than one PEG molecule. In particular embodiments, the ADIr is modified with about 1 to about 10, or from about 7 to about 15 PEG molecules, or from about 2 to about 8 or about 9 to about 12 PEG molecules. In some embodiments, the ADIr is modified with about 2, 3, 4, 5, 6, 7, 8, 9, 10, 11, 12, 13, 14, or 15 PEG molecules. In specific embodiments, ADIr is modified with 4.5-5.5 PEG molecules per ADIr. In some embodiment, ADIr is modified with 5±1.5 PEG molecules.

In certain embodiments, about 15% to about 70% of the primary amino groups in ADIr are modified with PEG, in some embodiments about 20% to about 65%, about 25% to about 60%, or in certain embodiments about 30% to about 55%, or 45% to about 50%, or in some embodiments about 50% of the primary amino groups in arginine deiminase are modified with PEG. When PEG is covalently bonded to the end terminus of ADIr, it may be desirable to have only 1 PEG molecule utilized. Increasing the number of PEG units on ADIr increases the circulating half-life of the enzyme. However, increasing the number of PEG units on ADIr decreases the specific activity of the enzyme. Thus, a balance needs to be achieved between the two, as would be apparent to one skilled in the art in view of the present disclosure.

In some embodiments, a common feature of biocompatible linkers is that they attach to a primary amine of arginine deiminase via a succinimide group. Once coupled with ADIr, SS-PEG has an ester linkage next to the PEG, which may render this site sensitive to serum esterase, which may release PEG from ADIr in the body. SPA-PEG and PEG2-NHS do not have an ester linkage, so they are not sensitive to serum esterase.

PEG which is attached to the protein may be either a straight chain, as with SS-PEG, SPA-PEG and SC-PEG, or a branched chain of PEG may be used, as with PEG2-NHS.

In certain embodiments, pegylation sites associated with ADIr located at or adjacent to the catalytic region of the enzyme are modified. In certain embodiments, the phrase "pegylation site" is defined as any site or position of ADI or a ADIr that may be covalently modified with polyethylene glycol. A "pegylation site" can be considered located at or adjacent the catalytic region of the enzyme where pegylation of the site results in a significant reduction in catalytic activity of the enzyme. The pegylation of such sites has traditionally resulted in the inactivation of the enzyme. For example, ADI from *Mycoplasma hominis* has a lysine at the 112 position which can be considered to be at or adjacent the catalytic region of the enzyme. The attachment of PEG to this lysine at the 112 position can inactivate the enzyme. In addition, ADI from *Mycoplasma hominis* has a cysteine at the 397 position which can be considered to be at or adjacent the catalytic region of the enzyme. The amino acid substitutions for cysteine at the 397 position can inactivate the enzyme. In particular, substituting alanine, histidine, arginine, serine, lysine or tyrosine for cysteine at the 397 position can result in a loss of all detectable enzyme activity. ADI from *Mycoplasma hominis* also has three lysine residues located near this conserved cysteine, in particular Lys374, Lys405 and Lys408. The attachment of PEG to Lys374, Lys405, Lys408 or combinations thereof can inactivate the enzyme.

It is to be understood that ADIr derived from other organisms may also have pegylation sites corresponding to 112 position of ADI from *Mycoplasma hominis*. In addition, ADI from some organisms may have lysine residues corresponding to the same general location as the 112 position of ADI from *Mycoplasma hominis*. The location of lysine in ADI from such organisms are known to the skilled person and are described in U.S. Pat. No. 6,635,462.

Thus, some embodiments provide for certain amino acid substitutions in the polypeptide chain of ADIr. These amino acid substitutions provide for modified ADIr that loses less activity when modified by a modifying agent, e.g., upon pegylation. By eliminating pegylation sites, or other known modification sites, at or adjacent to the catalytic region of enzyme, optimal modification, e.g., pegylation, can be achieved without the loss of activity.

In some embodiments, for example, as noted above, the amino acid substitutions employ non-natural amino acids for conjugation to PEG or other modifying agent (see, e.g., de Graaf et al., Bioconjug Chem. 20:1281-95, 2009). Certain embodiments thus include an ADIr enzyme that is conjugated to one or more PEGs via one or more non-natural amino acids. In some embodiments the non-natural amino acid comprises a side chain having a functional group selected from the group consisting of: an alkyl, aryl, aryl halide, vinyl halide, alkyl halide, acetyl, ketone, aziridine, nitrile, nitro, halide, acyl, keto, azido, hydroxyl, hydrazine, cyano, halo, hydrazide, alkenyl, alkynyl, ether, thio ether, epoxide, sulfone, boronic acid, boronate ester, borane, phenylboronic acid, thiol, seleno, sulfonyl, borate, boronate, phospho, phosphono, phosphine, heterocyclic-, pyridyl, naphthyl, benzophenone, a constrained ring such as a cyclooctyne, thioester, enone, imine, aldehyde, ester, thioacid, hydroxylamine, amino, carboxylic acid, alpha-keto carboxylic acid, alpha or beta unsaturated acids and amides, glyoxyl amide, and an organosilane group. In some embodiments, the non-natural amino acid is selected from the group consisting of: p-acetyl-L-phenylalanine, O-methyl-L-tyrosine, L-3-(2-naphthyl)alanine, 3-methyl-phenylalanine, O-4-allyl-L-tyrosine, homocysteine, 4-propyl-L-tyrosine, tri-O-acetyl-GlcNAcβ-serine, β-O-GlcNAc-L-serine, tri-O-acetyl-GalNAc-α-threonine, α-GalNAc-L-threonine, L-Dopa, a fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, and isopropyl-L-phenylalanine.

While ADIr-PEG is the illustrative modified ADIr described herein, as would be recognized by the skilled person ADIr may be modified with other polymers or appropriate molecules for the desired effect, in particular reducing antigenicity and increasing serum half-life.

It is to be understood that some embodiments are based on the understanding that certain structural characteristics of arginine deiminase may prevent or interfere with the proper and rapid renaturation when produced via recombinant technology. In particular, these structural characteristics hinder or prevent the enzyme from assuming an active conformation during recombinant production. In some embodiments, the term "active conformation" is defined as a three-dimensional structure that allows for enzymatic activity by unmodified or modified arginine deiminase. The active conformation may, in particular, be necessary for catalyzing the conversion of arginine into citrulline. The term "structural characteristic" may be defined as any trait, quality or property of the polypeptide chain resulting from a particular amino acid or combination of amino acids. For instance, arginine deiminase may contain an amino acid that results in a bend or kink in the normal peptide chain and thus hinders the enzyme from assuming an active conformation during renaturation of the enzyme. In particular, arginine deiminase from *Mycoplasma hominis* has a proline at the 210 position that may result in a bend or kink in the peptide chain, making it more difficult to renature the enzyme during recombinant production. It is to be understood that arginine deiminase derived from other organisms may also have sites corresponding to the 210 position of arginine deiminase from *Mycoplasma hominis*.

Some embodiments thus provide for certain amino acid substitutions in the polypeptide chain of wild type arginine deiminases. Examples include substitutions that eliminate the problematic structural characteristics in the peptide chain of arginine deiminase. Also included are substitutions that provide for improved renaturation of the modified arginine deiminase. These amino acid substitutions make possible rapid renaturation of modified arginine deiminases using reduced amounts of buffer. These amino acid substitutions may also provide for increased yields of renatured modified arginine deiminase. In some embodiments, the modified arginine deiminase has an amino acid substitution at P210 or the equivalent residue. As mentioned above, arginine deiminase derived from *Mycoplasma hominis* has the amino acid proline located at the 210 position. While not limiting the present invention, it is believed that the presence of the amino acid proline at position 210 results in a bend or kink in the normal polypeptide chain that increases the difficulty of renaturing (i.e., refolding) certain arginine deiminase enzymes. Substitutions for proline at position 210 make possible the rapid renaturation of modified arginine deiminase using reduced amounts of buffer. Substitutions for proline at position 210 (or the equivalent residue) may also provide for increased yields of renatured modified arginine deiminase. In some embodiments, the proline at position 210 (or the equivalent residue) is substituted with serine. Non-limiting examples of other substitutions include Pro210 to Thr210, Pro210 to Arg210, Pro210 to Asn210, Pro210 to Gln210 or Pro210 to Met210. By eliminating those structural characteristics associated with the amino acid of position 210 of the wild-type arginine deiminase, optimal refolding of the enzyme can be achieved.

The methods provided herein can involve either in vitro or in vivo applications. In the case of in vitro applications, including cell culture applications, the compounds described herein can be added to the cells in cultures and then incubated. The compounds described herein may also be used to facilitate the production of monoclonal and/or polyclonal antibodies, using antibody production techniques well known in the art. The monoclonal and/or polyclonal antibodies can then be used in a wide variety of diagnostic applications, as would be apparent to one skilled in the art.

The in vivo means of administration of the compounds or compositions described herein will vary depending upon the intended application. Administration of the ADIr compositions described herein, in pure form or in an appropriate pharmaceutical composition, can be carried out via any of the accepted modes of administration of agents for serving similar utilities. The pharmaceutical compositions can be prepared by combining ADIr, e.g., ADIr-PEG, ADIr-PEG 20, with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition.

Administration may be achieved by a variety of different routes, including oral, parenteral, nasal, intravenous, intradermal, subcutaneous or topical. Modes of administration depend upon the nature of the condition to be treated or prevented. Thus, an ADIr enzyme (e.g., ADIr-PEG, ADIr-PEG 20) can be administered orally, intranasally, intraperitoneally, parenterally, intravenously, intralymphatically, intratumorly, intramuscularly, interstitially, intra-arterially, subcutaneously, intraocularly, intrasynovial, transepithelial, and transdermally. An amount that, following administration, reduces, inhibits, prevents or delays the progression and/or metastasis of a cancer is considered effective. In certain embodiment, the ADIr compositions herein increase median survival time of patients by a statistically significant amount. In some embodiments, the ADIr treatments described herein increase median survival time of a patient by 4 weeks, 5 weeks, 6 weeks, 7 weeks, 8 weeks, 9 weeks, 10 weeks, 15 weeks, 20 weeks, 25 weeks, 30 weeks, 40 weeks, or longer. In certain embodiments, ADIr treatments increase median survival time of a patient by 1 year, 2 years, 3 years, or longer. In some embodiments, the ADIr treatments described herein increase progression-free survival by 2 weeks, 3 weeks, 4 weeks, 5 weeks, 6 weeks, 7 weeks, 8 weeks, 9 weeks, 10 weeks or longer. In certain embodiments, the ADIr treatments described herein increase progression-free survival by 1 year, 2 years, 3 years, or longer.

In certain embodiments, the amount administered is sufficient to result in tumor regression, as indicated by a statistically significant decrease in the amount of viable tumor, for example, at least a 10%, 20%, 30%, 40%, 50% or greater decrease in tumor mass, or by altered (e.g., decreased with statistical significance) scan dimensions. In certain embodiments, the amount administered is sufficient to result in stable disease. In certain embodiments, the amount administered is sufficient to result in clinically relevant reduction in symptoms of a particular disease indication known to the skilled clinician.

In certain embodiments the amount administered is sufficient to inhibit NO synthesis, inhibit angiogenesis, and or is sufficient to induce apoptosis in tumor cells or any combination thereof. NO synthesis, angiogenesis and apoptosis may be measured using methods known in the art, see, e.g., *Current Protocols in Immunology or Current Protocols in Molecular Biology*, John Wiley & Sons, New York, N.Y. (2009 and updates thereto); Ausubel et al., *Short Protocols in Molecular Biology*, $3^{rd}$ ed., Wiley & Sons, 1995; and other like references. In some embodiments the amount administered inhibits NO synthesis and inhibits the growth of melanoma and complements, adds to, or synergizes with other chemotherapies as described herein, such as cisplatin. Accordingly, some embodiments provide a method of treating melanoma by administering ADIr-PEG 20 in combination with cisplatin, wherein the treatment depletes endogenous nitric oxide (NO).

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The ADIr (e.g., ADIr-PEG) compositions may be administered alone or in combination with other known cancer treatments, such as radiation therapy, chemotherapy, transplantation, immunotherapy, hormone therapy, photodynamic therapy, etc. The compositions may also be administered in combination with antibiotics.

The ADIr compositions may also be administered alone or in combination with ADI-PEG 20 therapy. In certain embodiments, the ADIr as described herein are used in patients who have been treated with ADI-PEG 20 and who have developed anti-ADI-PEG 20 antibodies. Such patients no longer benefit from ADI-PEG 20 treatment as the enzyme is neutralized by the antibodies. Thus, in certain embodiments, the invention provides a method of treating, ameliorating the symptoms of, or inhibiting the progression of a cancer comprising administering to a patient in need thereof a therapeutically effective amount of a composition comprising ADI-PEG 20, and after a period of time, administering to the patient a composition comprising an ADIr as described herein, thereby treating, ameliorating the symptoms of, or inhibiting the progression of the cancer.

In some embodiments of the method, the period of time is determined by detecting a predetermined level of anti-ADI-PEG 20 antibodies in the patient, wherein the composition comprising an ADIr is administered following detection of the predetermined level of said anti-ADI-PEG 20 antibodies. In certain embodiments, threshold level(s) or predetermined levels of anti-ADI-PEG 20 antibodies in patients to be treated with ADI-PEG 20 and an ADIr enzyme described herein can be established. A "predetermined threshold level" (also referred to as "predetermined level" or "predetermined cut-off value"), or sometimes referred to as a predetermined cut off, of anti-ADI-PEG 20 antibodies may be established using methods known in the art, for example, using Receiver Operator Characteristic curves or "ROC" curves. In some embodiments, even very low levels of anti-ADI-PEG 20 antibodies is deemed sufficient to warrant switching treatment from ADI-PEG 20 to an ADIr-PEG described herein. In certain embodiments, an appropriate level of anti-ADI-PEG 20 that will determine when to terminate ADI-PEG 20 treatment and begin treatment with an ADIr composition described herein can be determined by the skilled clinician.

In some embodiments, the period of time is determined by detecting or otherwise observing ADI activity in the patient, wherein the composition is administered following detection or observation of a predetermined level of ADI activity. In particular embodiments, the composition is administered following detection or observation of a reduced level of ADI activity in the patient. ADI activity can be measured directly, for example, by assaying a biological sample for at least one indicator of ADI activity, or indirectly, for example, by observing the desired or intended effect of the ADI-PEG 20 treatment. In certain embodiments, an appropriate level of ADI activity that will determine when to terminate ADI-PEG 20 treatment and begin treatment with an ADIr-PEG described herein can be determined by the skilled clinician.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques.

Certain pharmaceutical compositions are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described ADIr composition in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of an ADIr-PEG described herein, such as ADIr-PEG 20, for treatment of a disease or condition of interest in accordance with teachings herein. In certain embodiments, the pharmaceutical or therapeutic compositions are sterile and/or pyrogen-free.

A pharmaceutical composition may be in the form of a solid or liquid. In some embodiments, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is generally either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, in certain embodiments, physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of ADIr as herein disclosed (e.g., ADIr-PEG, ADIr-PEG 20) such that a suitable dosage will be obtained. Typically, this amount is at least 0.01% of ADIr in the composition. When intended for oral administration, this amount may be varied to be between 0.1 and about 70% of the weight of the composition. Certain oral pharmaceutical compositions contain between about 4% and about 75% of ADIr. In certain embodiments, pharmaceutical compositions and preparations are prepared so that a parenteral dosage unit contains between 0.01 to 10% by weight of ADIr prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to ADIr (e.g., ADIr-PEG) and thereby assists in the delivery of the compound. Suitable agents that may act in this capacity include monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, sub-containers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises ADIr (e.g., ADIr-PEG) as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the ADIr (e.g., ADIr-PEG) composition so as to facilitate dissolution or homogeneous suspension of the ADIr (e.g., ADIr-PEG) in the aqueous delivery system.

The compositions may be administered in a therapeutically effective amount, which will vary depending upon a variety of factors including the activity of the specific compound (e.g., ADIr-PEG) employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

A therapeutically effective amount of a compound described herein is an amount that is effective to inhibit tumor growth. Generally, treatment is initiated with small dosages which can be increased by small increments until the optimum effect under the circumstances is achieved. Generally, a therapeutic dosage of compounds may be from about 1 to about 200 mg/kg twice a week to about once every two weeks. For example, the dosage may be about 1 mg/kg once a week as a 2 ml intravenous injection to about 20 mg/kg once every 3 days. In some embodiments, the dose may be from about 50 $IU/m^2$ to about 700 $IU/m^2$, administered about once every 3 days, about once a week, about twice a week, or about once every 2 weeks. In certain embodiments, the dose may be about 50 $IU/m^2$, 60 $IU/m^2$, 70 $IU/m^2$, 80 $IU/m^2$, 90 $IU/m^2$, 100 $IU/m^2$, 110 $IU/m^2$, 120 $IU/m^2$, 130 $IU/m^2$, 140 $IU/m^2$, 150 $IU/m^2$, 160 $IU/m^2$, 170 $IU/m^2$, 180 $IU/m^2$, 190 $IU/m^2$, 200 $IU/m^2$, 210 $IU/m^2$, 220 $IU/m^2$, 230 $IU/m^2$, 240 $IU/m^2$, 250 $IU/m^2$, 260 $IU/m^2$, 270 $IU/m^2$, 280 $IU/m^2$, 290 $IU/m^2$, 300 $IU/m^2$, 310 $IU/m^2$, about 320 $IU/m^2$, about 330 $IU/m^2$, 340 $IU/m^2$ about 350 $IU/m^2$, 360 $IU/m^2$, 370 $IU/m^2$, 380 $IU/m^2$, 390 $IU/m^2$, 400 $IU/m^2$, 410 $IU/m^2$, 420 $IU/m^2$, 430 $IU/m^2$, 440 $IU/m^2$, 450 $IU/m^2$, 500 $IU/m^2$, 550 $IU/m^2$, 600 $IU/m^2$, 620 $IU/m^2$, 630 $IU/m^2$, 640 $IU/m^2$, 650 $IU/m^2$, 660 $IU/m^2$, 670 $IU/m^2$, 680 $IU/m^2$, 690 $IU/m^2$, or about 700 $IU/m^2$ administered about once every 3 days, about once a week, about twice a week, or about once every 2 weeks. In certain embodiments, the dose may be modified as desired by the skilled clinician.

In some instances, the optimum dosage with ADIr-SS-PEG5,000 may be about twice a week, while the optimum dosage with ADIr-SS-PEG20,000 may be from about once a week to about once every two weeks. In certain embodiments, the optimum dosage with ADIr-SS-PEG20,000 may be about twice a week.

ADIr (e.g., ADIr-PEG) may be mixed with a phosphate buffered saline solution, or any other appropriate solution known to those skilled in the art, prior to injection. In some embodiments, a liquid composition comprising ADIr-PEG comprises about 10 to about 12 mg of ADIr; about 20 to about 40 mg of polyethylene glycol; about 1.27 mg±5% monobasic sodium phosphate, USP; about 3 mg±5% dibasic sodium phosphate, USP; about 7.6 mg±5% sodium chloride, USP; at a pH of about 6.6 to about 7; in an appropriate amount of water for injection (e.g., about 1 ml or about 2 ml).

In some embodiments, a liquid composition comprising an ADIr-PEG comprises histidine-HCl, and in certain embodiments, the composition buffer is from about 0.0035 M Histidine-HCl to about 0.35 M Histidine-HCl. In one particular embodiment, the composition is formulated in a buffer comprising 0.035 M Histidine-HCl at pH 6.8 with 0.13 M sodium chloride. In certain embodiments, the composition is formulated in a buffer comprising 0.02 M sodium phosphate buffer at pH 6.8 with 0.13 M sodium chloride. In some embodiments, a liquid composition comprising ADIr-PEG comprises about 10 to about 12 mg of ADIr; about 20 to about 40 mg of polyethylene glycol; about 5.4 mg±5% Histidine, USP; about 7.6 mg±5% sodium chloride, USP; at a pH of about 6.6 to about 7; in an appropriate amount of water for injection (e.g., about 1 ml or about 2 ml).

In some embodiments, a composition comprising ADIr (e.g., ADIr-PEG) has a pH of about 5 to about 9, about 6 to about 8, or about 6.5 to about 7.5. In some embodiments, the composition comprising ADIr has a pH of about 6.8±1.0.

In some embodiments, free PEG in a composition comprising ADIr (e.g., ADIr-PEG) is between 1-10%. In some embodiments, it is less than 7%, less than 6%, less than 5%, less than 4%, less than 3%, less than 2% or less than 1% of the total PEG. In certain embodiments, the unmodified ADIr in a composition comprising ADIr (e.g., ADIr-PEG) is less than about 1%, 0.9%, 0.8%, 0.7%, 0.6%, 0.5%, 0.4%, 0.3%, 0.2% or less than 0.1%. Generally, compositions comprising ADIr-PEG have total impurities less than or equal to about 4%, 3%, 2%, 1.5%, 1% or 0.5%. In some embodiments, the endotoxin limit meets the requirements stated in USP, i.e., <50 EU/mL.

In some embodiments, the free sulfhydryl in a composition comprising ADIr (e.g., ADIr-PEG) is greater than about 90%. In some embodiments, the free sulfhydryl in a composition comprising ADIr or ADIr-PEG is about 91%, about 92%, about 93%, about 94% or about 95%, about 96% about 97%, about 98% about 99% or more.

In some embodiments, the ADIr (e.g., ADIr-PEG) in a composition has a Km of from about 0.1 µM or 0.5 µM to about 15 µM, or is from about 1 µM to about 12 µM, about 1 µM to about 10 µM, about 1.5 µM to about 9 µM, about 1.5 µM to about 8 µM or about 1.5 µM to about 7 µM. In certain embodiments, the ADIr (e.g., ADIr-PEG) in a composition has a Km of about 1.0 µM to about 10 µM or about 1.5 µM to about 6.5 µM. In some embodiments, the ADIr or ADIr-PEG in a composition has a Km of about, at least about, or less than about 0.1 µM, about 0.5 µM, about 1.0 µM, about 1.5 µM, about 2 µM, about 2.5 µM, about 3 µM, about 3.5 µM, about 4 µM, about 4.5 µM, about 5 µM, about 5.5 µM, about 6 µM, about 6.5 µM, or about 7 µM, or about 8 µM, or about 9 µM, or about 10 µM.

In some embodiments, the ADIr (e.g., ADIr-PEG) in a composition has a Kcat of from about 0.5 sec$^{-1}$ to about 80 sec$^{-1}$, or about 0.5 sec$^{-1}$ to about 70 sec$^{-1}$, or about 0.5 sec$^{-1}$ to about 60 sec$^{-1}$, or about 0.5 sec$^{-1}$ to about 50 sec$^{-1}$, or about 0.5 sec$^{-1}$ to about 40 sec$^{-1}$, or about 0.5 sec$^{-1}$ to about 30 sec$^{-1}$, or about 0.5 sec$^{-1}$ to about 20 sec$^{-1}$, or about 0.5 sec$^{-1}$ to about 15 sec$^{-1}$, or is from about 0.5 sec$^{-1}$ to about 80 sec$^{-1}$, or about 1 sec$^{-1}$ to about 80 sec$^{-1}$, or about 5 sec$^{-1}$ to about 80 sec$^{-1}$, or about 10 sec$^{-1}$ to about 80 sec$^{-1}$, or about 20 sec$^{-1}$ to about 80 sec$^{-1}$, or about 30 sec$^{-1}$ to about 80 sec$^{-1}$, or about 40 sec$^{-1}$ to about 80 sec$^{-1}$, or about 50 sec$^{-1}$ to about 80 sec$^{-1}$, or about 60 sec$^{-1}$ to about 80 sec$^{-1}$, or about 70 sec$^{-1}$ to about 80 sec$^{-1}$, or about 1 sec$^{-1}$ to about 12 sec$^{-1}$, about 1 sec$^{-1}$ to about 10 sec$^{-1}$, about 1.5 sec$^{-1}$ to about 9 sec$^{-1}$, about 2 sec$^{-1}$ to about 8 sec$^{-1}$ or about 2.5 sec$^{-1}$ to about 7 sec$^{-1}$. In certain embodiments, the ADIr (e.g., ADIr-PEG) in a composition has a Kcat of about 2.5 sec$^{-1}$ to about 7.5 sec$^{-1}$. In some embodiments, the ADIr or ADIr-PEG in a composition has a Kcat of about or at least about 2.5 sec$^{-1}$, about 3 sec$^{-1}$, about 3.5 sec$^{-1}$, about 4 sec$^{-1}$, about 4.5 sec$^{-1}$, about 5 sec$^{-1}$, about 5.5 sec$^{-1}$, about 6 sec$^{-1}$, about 6.5 sec$^{-1}$, about 7 sec$^{-1}$, about 7.5 sec$^{-1}$ or about 8 sec$^{-1}$, about 10 sec$^{-1}$, about 15 sec$^{-1}$, about 20 sec$^{-1}$, about 25 sec$^{-1}$, about 30 sec$^{-1}$, about 35 sec$^{-1}$, about 40 sec$^{-1}$, about 45 sec$^{-1}$, about 50 sec$^{-1}$, about 55 sec$^{-1}$, about 60 sec$^{-1}$, about 65 sec$^{-1}$, about 70 sec$^{-1}$, about 75 sec$^{-1}$, about 80 sec$^{-1}$, about 85 sec$^{-1}$, about 90 sec$^{-1}$, about 95 sec$^{-1}$, or about 100 sec$^{-1}$.

In some embodiments, the ADIr (e.g., ADIr-PEG) in a composition has a conductivity (also referred to in the art as specific conductance) of about 5 mS/cm to about 20 mS/cm, or about 5 mS/cm to about 15 mS/cm, about 7 mS/cm to about 15 mS/cm, about 9 mS/cm to about 15 mS/cm or about 10 mS/cm to about 15 mS/cm. In some embodiments, the ADIr (e.g., ADIr-PEG) in a composition has a conductivity of about 9 mS/cm, about 10 mS/cm, about 11 mS/cm, about 12 mS/cm or about 13 mS/cm, about 14 mS/cm or about 15 mS/cm. In certain embodiments, the ADIr (e.g., ADIr-PEG) in a composition has a conductivity of about 13 mS/cm±1.0 mS/cm.

In some embodiments, the ADIr (e.g., ADIr-PEG) in a composition has an osmolality of about 50 mOsm/kg to about 500 mOsm/kg, about 100 mOsm/kg to about 400 mOsm/kg, about 150 mOsm/kg to about 350 mOsm/kg, about 200 mOsm/kg to about 350 mOsm/kg or about 250 mOsm/kg to about 350 mOsm/kg. In certain embodiments, the ADIr (e.g., ADIr-PEG) in a composition has an osmolality of about 300±30 mOsm/kg.

In some embodiments, the protein concentration is about 11.0±1.0 mg/mL. In certain embodiments, the protein concentration is between about 8 and about 15 mg/mL. In certain embodiments, the protein concentration is about 8, 9, 10, 10.5, 11, 11.5, 12, 12.5, 13, 13.5, 14, or 15 mg/mL.

In some embodiments, the specific enzyme activity is between about 5.0 and 90 IU/mg or between about 5 and 55 IU/mg, where 1 IU is defined as the amount of enzyme that converts one µmol of arginine into one µmol of citrulline and 1 µmol of ammonia in one minute at 37° C. and the potency is 100±20 IU/mL. In certain embodiments, the specific enzyme activity is about 5.5, 6, 6.5, 7, 7.5, 8, 8.5, 9.0, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 35, 40, 45, 50, 55, 55, 60, 65, 70, 75, 80, 85, 90, 95, or 100±2.0 IU/mg. In one particular embodiment, the specific enzyme activity is 9±2.0 IU/mg.

Compositions comprising an ADIr (e.g., ADIr-PEG) described herein can be administered simultaneously with, prior to, or after administration of one or more other therapeutic agents, including ADI-PEG 20. Such combination therapy may include administration of a single pharmaceutical dosage formulation which contains a compound of the invention and one or more additional active agents, as well as administration of compositions comprising an ADIr described herein (e.g., ADIr-PEG) and each active agent in its own separate pharmaceutical dosage formulation. For example, the ADIr (e.g., ADIr-PEG) and the other active agent can be administered to the patient together in a single oral dosage composition such as a tablet or capsule, or each agent administered in separate oral dosage formulations. Similarly, the ADIr (e.g., ADIr-PEG) and the other active agent can be administered to the patient together in a single parenteral dosage composition such as in a saline solution or other physiologically acceptable solution, or each agent administered in separate parenteral dosage formulations, by the same or different routes (e.g., one by injection, one by oral). Where separate dosage formulations are used, the compositions comprising the ADIr (e.g., ADIr-PEG) and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of the ADIr compositions of this disclosure in combination with one or more other therapeutic agents. Such therapeutic agents may be accepted in the art as a standard treatment for a particular disease state as described herein, such as a particular cancer or GVHD. Exemplary therapeutic agents contemplated include cytokines, growth factors, steroids, NSAIDs, DMARDs, anti-inflammatories, chemotherapeutics, radiotherapeutics, autophagy inhibitors, or other active and ancillary agents.

In certain embodiments, the ADIr (e.g., ADIr-PEG) compositions disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and docetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin. Further chemotherapeutic agents include sorafenib and other protein kinase inhibitors such as afatinib, axitinib, bevacizumab, cetuximab, crizotinib, dasatinib, erlotinib, fostamatinib, gefitinib, imatinib, lapatinib, lenvatinib, mubritinib, nilotinib, panitumumab, pazopanib, pegaptanib, ranibizumab, ruxolitinib, trastuzumab, vandetanib, vemurafenib, and sunitinib; sirolimus (rapamycin), everolimus and other mTOR inhibitors. Pharmaceutically acceptable salts, acids or derivatives of any of the above are also contemplated for use herein.

In certain embodiments, the ADIr (e.g., ADIr-PEG) compositions disclosed herein may be administered in conjunction with any number of autophagy inhibitors. In some preferred embodiments, the autophagy inhibitor is selected from the group consisting of: chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels, adenosine, N6-mercaptopurine riboside, wortmannin, and vinblastine. In addition, antisense or siRNA that inhibits expression of proteins essential for autophagy, such as for example ATG5, may also be used.

In some embodiments, the combination of ADIr (e.g., ADIr-PEG) with one or more therapeutic agents acts complementary, additively, or synergistically. In this regard, complementary or synergizing agents are described herein, which include a therapeutic agent (e.g., chemotherapeutic agent, autophagy inhibitor, mTOR inhibitor, or any other therapeutic agent used for the treatment of cancer, GVHD, or inflammatory bowel disease as described herein) that is capable of acting complementary or synergistically with ADIr-PEG as provided herein, where such complementarity or synergy manifests as a detectable effect that is greater (i.e., in a statistically significant manner relative to an appropriate control condition) in magnitude than the effect that can be detected when the chemotherapeutic agent is present but the ADIr (e.g., ADIr-PEG) composition is absent, and/or when the ADIr (e.g., ADIr-PEG) is present but the chemotherapeutic agent is absent. Methods for measuring synergy and complementarity are known in the art (see e.g., Cancer Res Jan. 15, 2010 70; 440).

The compositions comprising ADIr (e.g., ADIr-PEG) and optionally other therapeutic agents, as described herein, may be used in therapeutic methods for treating cancer and methods for preventing metastasis of a cancer. Thus, some embodiments include methods for treating, ameliorating the symptoms of, or inhibiting the progression of or prevention of a variety of different cancers. Some embodiments include methods for treating, ameliorating the symptoms of, or inhibiting the progression of GVHD. Particular embodiments include methods for treating, ameliorating the symptoms of, or inhibiting the progression of a cancer or GVHD in a patient comprising administering to the patient a therapeutically effective amount of ADIr composition as described herein, optionally, following treatment with ADI-PEG 20, particularly where a patient develops anti-ADI-PEG 20 antibodies, thereby treating, ameliorating the symptoms of, or inhibiting the progression of the cancer or GVHD. Thus, the ADIr compositions described herein may be administered to an individual afflicted with inflammatory bowel disease (e.g., Crohn's disease; ulcerative colitis), GVHD or a cancer, including, but not limited to hepatocellular carcinoma, leukemia (e.g. acute myeloid leukemia and relapsed acute myeloid leukemia), melanoma including metastatic melanoma, sarcomas (including, but not limited to, metastatic sarcomas, uterine leiomyosarcoma), pancreatic cancer, prostate cancer (such as, but not limited to, hormone refractory prostate cancer), mesothelioma, lymphatic leukemia, chronic myelogenous leukemia, lymphoma, small cell lung cancer, breast cancer, ovarian cancer, colorectal cancer, gastric cancer (including, but not limited to, gastric adenocarcinoma), glioma, glioblastoma multiform, retinoblastoma, neuroblastoma, non-small cell lung cancer (NSCLC), kidney cancer (including but not limited to renal cell carcinoma), bladder cancer, uterine cancer, esophageal cancer, brain cancer, head and neck cancers (including, but not limited to, squamous cell carcinoma of the head and neck; cancer of the tongue), cervical cancer, testicular cancer, gallbladder, cholangiocarcinoma, and stomach cancer.

Also included are methods of treating, ameliorating the symptoms of, or inhibiting the progression of a cancer in a patient comprising administering to the patient a composition comprising ADIr (e.g., ADIr-PEG), and optionally one or more other therapeutic agents, as described herein, wherein the cancer is deficient in ASS, ASL, or both. In this regard, ASS or ASL deficiency may be a reduction in expression as measured by mRNA expression or protein expression, or may be a reduction in protein activity, and generally comprises a statistically significant reduction in expression or activity as determined by the skilled person. Reduced ASS or ASL expression or activity may be a reduction in expression or activity of about 5%, 10%, 15%, 20%, 25%, 30%, 35%, 40%, 45%, 50%, 55%, 60%, 65%, 70%, or more, as compared to expression or activity in an appropriate control sample known to be cancer free. In certain embodiments, ASS or ASL expression or activity is reduced by at least twofold as compared to expression or activity in a non-cancer control sample.

In certain embodiments, the reduced expression or activity of ASS or ASL results from methylation of the ASS or ASL promoter or inhibition of the ASS or ASL promoter. In some embodiments the reduction in expression or activity of ASS or ASL results from a DNA mutation (e.g., one or more point mutations, small deletions, insertions, and the like) or a chromosomal abnormality resulting in deletion of the gene. In some embodiments, the cancer is ASS or ASL negative, meaning no expression or activity is observed.

Reduction in ASS or ASL expression or activity may be measured using any methods known in the art, such as but not limited to, quantitative PCR, immunohistochemistry, enzyme activity assays (e.g., assay to measure conversion of citrulline into argininosuccinate or conversion of argininosuccinate into arginine and fumarate), and the like.

Thus, certain embodiments include methods for treating, ameliorating the symptoms of, or inhibiting the progression of a cancer in a patient comprising administering to the patient a composition comprising an ADIr as described herein (e.g., ADIr-PEG), wherein the cancer exhibits reduced expression or activity of ASS or ASL, or both, wherein the cancer includes, but is not limited to hepatocellular carcinoma, leukemia (e.g. acute myeloid leukemia and relapsed acute myeloid leukemia), melanoma including metastatic melanoma, sarcomas (including, but not limited to, metastatic sarcomas, uterine leiomyosarcoma), pancreatic cancer, prostate cancer (such as, but not limited to, hormone refractory prostate cancer), mesothelioma, lymphatic leukemia, chronic myelogenous leukemia, lymphoma, small cell lung cancer, breast cancer, ovarian cancer, colorectal cancer, gastric cancer (including, but not limited to, gastric adenocarcinoma), glioma, glioblastoma multiform, retinoblastoma, neuroblastoma, non-small cell lung cancer (NSCLC), kidney cancer (including but not limited to renal cell carcinoma), bladder cancer, uterine cancer, esophageal cancer, brain cancer, head and neck cancers (including, but not limited to, squamous cell carcinoma of the head and neck; cancer of the tongue), cervical cancer, testicular cancer, gallbladder, cholangiocarcinoma, and stomach cancer.

Various studies in the literature have shown that ASS is deficient in the following tumors: acute myelogenous leukemia (AML), bladder, breast, colorectal, gastric, glioblastoma, HCC, lymphoma, melanoma, mesothelioma, non-small cell lung, ovarian, pancreatic, prostate, renal, sarcoma, and small cell lung. Accordingly, treatment of these ASS-deficient cancers is specifically contemplated herein, with ADIr-PEG alone or in combination with other treatments, including treatment first with ADI-PEG 20.

Also included are methods for treating, ameliorating the symptoms of, or inhibiting the progression of cancer in a patient comprising administering to the patient a composition comprising ADIr as described herein (e.g., ADIr-PEG, ADIr-PEG 20), in combination with an autophagy inhibitor. Some embodiments include methods for treating cancer in a patient comprising administering to the patient a therapeutically effective amount of a composition comprising ADIr as described herein in combination with autophagy inhibitor wherein the cancer is pancreatic cancer or small cell lung cancer.

Some embodiments include methods of treatment where administration of the compositions comprising ADIr described herein depletes arginine in the plasma for at least one month, 2 months, 3 months, 4 months, 5 months, 6 months or longer. Certain embodiments include methods of treatment where administration of the compositions comprising ADIr described herein depletes arginine in the plasma for at least one month, 2 months, 3 months, 4 months, 5 months, 6 months or longer after terminating treatment with ADI-PEG 20 following detection of anti-ADI-PEG 20 antibodies.

EXAMPLES

Example 1

Screening and Selection of ADI Enzymes that have Low Cross-Reactivity with Patient Anti-ADI-PEG 20 Antibodies

This example describes the screening and selection of ADI enzymes that have low cross-reactivity with patient anti-ADI-PEG 20 antibodies.

From a large number of ADI enzymes, Table 1 lists 27 ADI enzymes selected for their sequence percent identity relative to M. hominis ADI.

TABLE 1

Selected ADI Sequences with Varying Degrees of Similarity to M. hominis ADI

| ORGANISM | PERCENT IDENTITY | SEQUENCE ACCESSION NUMBER | SEQ ID NO: |
|---|---|---|---|
| Mycoplasma hominis | 100.0 | gi\|728876 | 1 |
| Mycoplasma salivarium | 81.95 | gi\|639205998 | 2 |
| Mycoplasma spumans | 81.51 | gi\|652844751 | 3 |
| Mycoplasma canadense | 81.22 | gi\|780004832 | 20 |
| Mycoplasma auris | 78.54 | gi\|490558584 | 4 |
| Mycoplasma hyosynoviae | 78.78 | gi\|738491959 | 5 |
| Mycoplasma cloacale | 78.97 | gi\|657216914 | 6 |
| Mycoplasma anseris | 78.73 | gi\|697347301 | 21 |
| Mycoplasma alkalescens | 77.67 | gi\|488970417 | 7 |
| Mycoplasma orale | 79.27 | gi\|551316378 | 8 |
| Mycoplasma iners | 60.20 | gi\|657715567 | 9 |
| Mycoplasma meleagridis | 59.1 | gi\|803632330 | 22 |
| Mycoplasma alvi | 58.46 | gi\|697091625 | 23 |
| Mycoplasma penetrans | 58.1 | gi\|768722109 | 24 |
| Mycoplasma gallinarum | 58.06 | gi\|653082428 | 10 |
| Mycoplasma pirum | 56.05 | gi\|652846075 | 11 |
| Mycoplasma primatum | 56.86 | gi\|657716867 | 12 |
| Mycoplasma fermentans | 56.11 | gi\|753838319 | 25 |
| Mycoplasma lipofaciens | 55.64 | gi\|652840093 | 13 |
| Mycoplasma felifaucium | 55.85 | gi\|653084388 | 14 |
| Mycoplasma imitans | 53.85 | gi\|652843200 | 15 |
| Mycoplasma opalescens | 54.25 | gi\|659858924 | 16 |
| Mycoplasma moatsii | 50.24 | gi\|551314758 | 17 |
| Mycoplasma elephantis | 52.63 | gi\|653084064 | 18 |
| Mycoplasma pneumoniae | 51.97 | gi\|12643471 | 26 |
| Mycoplasma testudinis | 49.50 | gi\|652838532 | 19 |
| Mycoplasma sp. CAG:877 | 39.28 | gi\|524101565 | 27 |
| Mycoplasma sp. CAG:472 | 38.07 | gi\|524735679 | 28 |

A number of ADI enzymes from a variety of organisms were characterized to determine which enzymes would be expected to remove and maintain low concentrations of arginine in patient blood, even in the presence of anti-ADI-PEG 20 antibodies. As detailed below, these studies show that ADI from a number of species that are closely related to M. hominis, based on sequence identity, have sufficiently good enzyme catalytic properties, measured at various temperatures and pH, and also show reduced cross-reactivity with anti-ADI-PEG 20 antibodies.

ADI Preparation.

Recombinant ADI enzymes were cloned, expressed, and purified for testing according to standard protocols, as described, for example, in Gallego et al., PLOS One, 7(10): e47886, 2012; Monstadt and Holldorf, Biochem. J. 273:739-745, 1990; Joo Noh et al., Molecules and Cells. 13:137-143, 2002; and Sugimura et al., Infection and Immunity. 58:2510-2515, 1990.

Human Anti-ADI-PEG20 Antibody Purification.

Anti-ADI-PEG20 antibody was purified from plasma samples of patients who had received ADI-PEG20 during a clinical study. For example, a total of 60 ml of plasma was pooled from 8 different patients that had reached high titer (titer >1=4) against ADI-PEG20 as determined by an ELISA assay. A two-step purification was used, a Protein "A" chromatography (GE Healthcare) followed by an ADI affinity chromatography. About 20 mg of purified antibody was obtained and stored at −80° C. in aliquots until needed.

ADI Enzyme Assays.

Arginine deiminase (ADI) catalyzes the conversion of L-arginine to L-citrulline and ammonia. The amount of L-citrulline can be detected by a colorimetric endpoint assay (see, for example, Knipp and Vasak, Analytical Biochem. 286:257-264, 2000) and compared to a standard curve of known amounts of L-citrulline in order to calculate the specific activity of ADI expressed as IU/mg of protein. One IU of enzyme activity was defined as the amount of enzyme that produces 1 µmol of citrulline per minute at the pH and temperature being tested. Standard assay conditions were performed at 37° C. in Physiological HEPES Buffer (PHB) 50 mM HEPES, 160 mM NaCl pH 7.4 (Lang and Zander, Clin Chem Lab Med. 37:563-571, 1999) plus 0.1% BSA. All samples and standards were run in duplicate or triplicate where conditions permitted.

Km and Kcat values were determined by using a variation of the activity assay described above. As with the activity assay (or unless otherwise indicated), all reactions were run at 37° C. in PHB plus 0.1% BSA. Enzyme concentration, reaction time, and substrate concentration range were adjusted for each of the ADI or ADIr constructs to account for their differences in activity. In general, 2 nM enzyme, 5 minute reaction time, and a 0-160 µM arginine were used as starting conditions. When optimizing the conditions, particular attention was paid towards the amount of substrate consumed as a percentage of total substrate added to the reaction. Typically, the lower limit of detection was about 1 µM of citrulline with the lower limit of quantitation being about 2 µM. A citrulline standard curve was run on every plate and used to quantify the citrulline produced by the enzymatic reaction.

Activity assays were also performed to assess enzymatic activity in the presence of anti-ADI-PEG20 (antibody neutralization profiles). These assays were performed as described above and in the presence of 640 nM, 320 nM, 160 nM, 80 nM, 40 nM, 20 nM, 10 nM, and 0 nM of anti-ADI-PEG20 antibodies.

Calculations.

The citrulline concentration (µM) produced in each reaction well was calculated and averaged using the citrulline standard curve. The velocity of each reaction was then calculated in µM/min/50 nM ADI. Specific activity (IU/mg or µmols product/min/mg ADI) was calculated by multiplying this value by the "IU" factor (IU factor was calculated from the molecular weight of the ADI and the reaction volume).

The data are shown in Tables 2-7 below.

TABLE 2

Selected Native ADI Sequences and Properties

| Organism | Specific Activity (IU/mg) | Kcat (s−1) | Km (uM) |
|---|---|---|---|
| Mycoplasma hominis | + | + | + |
| Mycoplasma salivarium | ++ | ++ | + |
| Mycoplasma spumans | +++ | +++ | + |
| Mycoplasma canadense | + | + | + |

TABLE 2-continued

Selected Native ADI Sequences and Properties

| Organism | Specific Activity (IU/mg) | Kcat (s−1) | Km (uM) |
|---|---|---|---|
| Mycoplasma cloacale | ++ | + | + |
| Mycoplasma hyosynoviae | − | − | + |
| Mycoplasma anseris | + | − | + |
| Mycoplasma auris | + | − | + |
| Mycoplasma alkalescens | ++ | ++ | − |
| Mycoplasma iners | ++++ | ++++ | + |
| Mycoplasma meleagridis | +++ | ++ | + |
| Mycoplasma penetrans | ++ | ++ | − |
| Mycoplasma gallinarum | ++++ | +++ | + |
| Mycoplasma primatum | +++ | +++ | + |
| Mycoplasma fermentans | − | − | ND |
| Mycoplasma lipofaciens | − | − | ND |
| Mycoplasma opalescens | ++ | ++ | − |
| Mycoplasma imitans | − | ND | ND |
| Mycoplasma sp. CAG:877 | − | ND | ND |
| Mycoplasma sp. CAG:472 | − | ND | ND |

TABLE 3

Selected PEG-ADI Sequences and Properties

| Organism | Specific Activity (IU/mg) | Kcat (s−1) | Km (uM) |
|---|---|---|---|
| Mycoplasma hominis | + | + | + |
| Mycoplasma salivarium | ++ | ++ | + |
| Mycoplasma spumans | +++ | +++ | + |
| Mycoplasma canadense | ++ | ++ | − |
| Mycoplasma cloacale | ++ | ++ | + |
| Mycoplasma hyosynoviae | − | + | ND |
| Mycoplasma anseris | ++ | ++ | − |
| Mycoplasma auris | ++ | ++ | − |
| Mycoplasma alkalescens | − | + | ND |
| Mycoplasma iners | ++++ | ++++ | + |
| Mycoplasma meleagridis | +++ | ++ | + |
| Mycoplasma penetrans | + | + | − |
| Mycoplasma gallinarum | ++++ | ++++ | + |
| Mycoplasma primatum | +++ | +++ | + |
| Mycoplasma opalescens | − | ND | ND |

TABLE 4

Selected Native ADI Sequences and Properties

| | Specific Activity at Concentration of α-ADI Ab Indicated (nM)* | | | | | | | |
|---|---|---|---|---|---|---|---|---|
| Organism | 640 | 320 | 160 | 80 | 40 | 20 | 10 | 0 |
| Mycoplasma hominis | ND | 33 | 39 | 59 | 76 | 86 | 94 | 100 |
| Mycoplasma salivarium | 25 | 49 | 69 | 84 | 92 | 96 | 96 | 100 |
| Mycoplasma spumans | 42 | 59 | 76 | 87 | 95 | 96 | 98 | 100 |
| Mycoplasma canadense | 27 | 56 | 89 | 104 | 121 | 122 | 113 | 100 |
| Mycoplasma cloacale | 24 | 50 | 72 | 85 | 95 | 98 | 98 | 100 |
| Mycoplasma hyosynoviae | 22 | 47 | 72 | 83 | 101 | 100 | 91 | 100 |
| Mycoplasma anseris | 39 | 60 | 90 | 99 | 109 | 106 | 106 | 100 |
| Mycoplasma auris | 45 | 64 | 81 | 90 | 95 | 99 | 100 | 100 |
| Mycoplasma alkalescens | 27 | 48 | 71 | 83 | 92 | 94 | 95 | 100 |
| Mycoplasma iners | 63 | 80 | 89 | 93 | 96 | 98 | 99 | 100 |
| Mycoplasma meleagridis | 64 | 90 | 104 | 101 | 110 | 101 | 112 | 100 |
| Mycoplasma penetrans | 67 | 86 | 91 | 90 | 89 | 106 | 100 | 100 |
| Mycoplasma gallinarum | 67 | 82 | 89 | 94 | 96 | 96 | 97 | 100 |
| Mycoplasma primatum | 64 | 79 | 89 | 94 | 98 | 99 | 99 | 100 |
| Mycoplasma opalescens | 66 | 91 | 95 | 102 | 106 | 106 | 104 | 100 |

*Indicated as percentage (%) specific activity (IU/mg) relative to activity with no antibody (0 nM)

TABLE 5

Selected PEG-ADI Sequences and Properties

| | Specific Activity at Concentration of α-ADI Ab Indicated (nM)* | | | | | | | |
|---|---|---|---|---|---|---|---|---|
| Organism | 640 | 320 | 160 | 80 | 40 | 20 | 10 | 0 |
| Mycoplasma hominis | ND | 53 | 64 | 77 | 89 | 93 | 94 | 100 |
| Mycoplasma salivarium | 43 | 59 | 77 | 85 | 91 | 94 | 95 | 100 |
| Mycoplasma spumans | 58 | 72 | 83 | 91 | 97 | 97 | 99 | 100 |
| Mycoplasma canadense | 42 | 62 | 79 | 94 | 91 | 92 | 95 | 100 |
| Mycoplasma cloacale | 31 | 52 | 72 | 82 | 93 | 95 | 95 | 100 |
| Mycoplasma anseris | 41 | 59 | 71 | 91 | 93 | 93 | 99 | 100 |
| Mycoplasma auris | 56 | 70 | 82 | 88 | 93 | 95 | 96 | 100 |
| Mycoplasma alkalescens | 42 | 59 | 78 | 87 | 92 | 97 | 98 | 100 |
| Mycoplasma iners | 65 | 84 | 92 | 94 | 98 | 99 | 94 | 100 |
| Mycoplasma meleagridis | 56 | 79 | 93 | 101 | 106 | 105 | 107 | 100 |
| Mycoplasma penetrans | 69 | 85 | 93 | 101 | 104 | 104 | 105 | 100 |
| Mycoplasma gallinarum | 62 | 77 | 87 | 91 | 94 | 99 | 100 | 100 |
| Mycoplasma primatum | 65 | 80 | 86 | 91 | 93 | 96 | 98 | 100 |

*Indicated as percentage (%) specific activity (IU/mg) relative to activity with no antibody (0 nM)

TABLE 6

Selected Native-ADI Sequences and Properties

| Organism | \*Specific Activity at Temperature Indicated | | | | | | | |
|---|---|---|---|---|---|---|---|---|
| | 20° C. | 24° C. | 28° C. | 32° C. | 37° C. | 40° C. | 44° C. | 48° C. |
| *Mycoplasma hominis* | 37 | 50 | 66 | 85 | 100 | 105 | 103 | 80 |
| *Mycoplasma salivarium* | 20 | 32 | 46 | 69 | 100 | 120 | 147 | 168 |
| *Mycoplasma spumans* | 25 | 38 | 53 | 75 | 100 | 118 | 135 | 135 |
| *Mycoplasma canadense* | 21 | 32 | 43 | 74 | 100 | 127 | 160 | 185 |
| *Mycoplasma cloacale* | 17 | 28 | 44 | 65 | 100 | 124 | 147 | 180 |
| *Mycoplasma hyosynoviae* | 16 | 26 | 41 | 64 | 100 | 104 | 126 | 124 |
| *Mycoplasma anseris* | 17 | 23 | 44 | 60 | 100 | 128 | 159 | 179 |
| *Mycoplasma auris* | 18 | 29 | 44 | 67 | 100 | 122 | 157 | 174 |
| *Mycoplasma alkalescens* | 20 | 31 | 45 | 67 | 100 | 119 | 146 | 160 |
| *Mycoplasma iners* | 36 | 52 | 63 | 78 | 100 | 125 | 142 | 191 |
| *Mycoplasma meleagridis* | 40 | 49 | 60 | 75 | 100 | 95 | 58 | 20 |
| *Mycoplasma penetrans* | 53 | 52 | 67 | 74 | 100 | 108 | 118 | 114 |
| *Mycoplasma gallinarum* | 41 | 51 | 67 | 81 | 100 | 119 | 145 | 171 |
| *Mycoplasma primatum* | 31 | 46 | 60 | 79 | 100 | 116 | 124 | 128 |
| *Mycoplasma opalescens* | 29 | 35 | 47 | 66 | 100 | 106 | 135 | 132 |

*Indicated as percentage (%) specific activity (IU/mg) relative to activity at 37° C.

TABLE 7

Selected Native-ADI Sequences and Properties

| Organism | Specific Activity* at pH Indicated | | | | | | | | | | | |
|---|---|---|---|---|---|---|---|---|---|---|---|---|
| | 2.4 | 3.2 | 4 | 4.8 | 5.6 | 6.4 | 7 | 7.6 | 8.4 | 9.2 | 10 | 10.4 |
| *Mycoplasma hominis* | 5 | 6 | 17 | 66 | 94 | 71 | 88 | 58 | 17 | 26 | 18 | 5 |
| *Mycoplasma salivarium* | 1 | 1 | 1 | 55 | 124 | 132 | 114 | 82 | 46 | 59 | 40 | 10 |
| *Mycoplasma spumans* | 1 | 1 | 1 | 58 | 117 | 119 | 108 | 84 | 44 | 62 | 45 | 10 |
| *Mycoplasma canadense* | 0 | 1 | 1 | 67 | 148 | 149 | 144 | 96 | 47 | 67 | 49 | 20 |
| *Mycoplasma cloacale* | 0 | 0 | 0 | 43 | 126 | 130 | 113 | 86 | 46 | 64 | 46 | 13 |
| *Mycoplasma hyosynoviae* | 0 | 1 | 1 | 22 | 124 | 132 | 117 | 85 | 41 | 39 | 26 | 6 |
| *Mycoplasma anseris* | 0 | 0 | 1 | 51 | 159 | 171 | 135 | 108 | 55 | 82 | 59 | 22 |
| *Mycoplasma auris* | 0 | 1 | 1 | 1 | 87 | 92 | 98 | 87 | 50 | 69 | 48 | 4 |
| *Mycoplasma alkalescens* | 0 | 0 | 0 | 38 | 113 | 123 | 106 | 78 | 38 | 53 | 35 | 7 |
| *Mycoplasma iners* | 0 | 1 | 15 | 32 | 76 | 83 | 84 | 78 | 45 | 66 | 55 | 26 |
| *Mycoplasma meleagridis* | 0 | 3 | 3 | 6 | 84 | 90 | 103 | 98 | 46 | 55 | 40 | 5 |
| *Mycoplasma penetrans* | 0 | 0 | 7 | 41 | 123 | 130 | 129 | 100 | 42 | 64 | 51 | 14 |
| *Mycoplasma gallinarum* | 0 | 1 | 18 | 36 | 91 | 90 | 104 | 92 | 50 | 69 | 56 | 26 |
| *Mycoplasma prima tum* | 0 | 1 | 0 | 27 | 81 | 94 | 99 | 92 | 50 | 76 | 60 | 17 |
| *Mycoplasma opalescens* | 0 | 1 | 1 | 2 | 83 | 97 | 115 | 93 | 51 | 84 | 65 | 23 |

*Indicated as percentage (%) specific activity (IU/mg) relative to activity at pH 7.4

These data show, inter alia, that native and PEGylated ADI enzymes that are highly homologous to *M. hominis* ADI (about 50-100 percent identity) maintained excellent catalytic activity (Tables 2-4), including at various pH (Table 6) and temperature-defined (Table 7) conditions. They also showed reduced affinity toward patient anti-ADI-PEG 20 antibodies, as measured by (increased) enzyme activity in the presence of anti-ADI-PEG 20 antibodies (Tables 4-5), for example, relative to that of *Mycoplasma hominis*. Accordingly, these ADI enzymes may have therapeutic utility for use in therapy for the treatment of cancer, either alone or following ADI-PEG 20 treatment, to extend and/or increase the effectiveness of arginine depletion therapy.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A therapeutic composition comprising an isolated, recombinant arginine deiminase (ADI) that is at least 90% pure, or a fragment thereof having ADI activity, and a pharmaceutically-acceptable carrier, wherein the ADI displays at least 95% sequence identity to SEQ ID NO:10 and has reduced cross-reactivity with patient anti-ADI-PEG 20 antibodies, and wherein the composition is sterile and substantially endotoxin-free.

2. The therapeutic composition of claim 1 wherein the isolated, recombinant ADI has one or more properties comparable to or better than those of ADI-PEG 20.

3. The therapeutic composition of claim 2 wherein the one or more properties is Kcat, Km, pH optimum, stability, in vivo proteolytic stability, or no requirement for ions or cofactors that are not already present in blood, or any combination thereof.

4. The therapeutic composition of claim 1 wherein the isolated, recombinant ADI displays at least 98% sequence identity to SEQ ID NO:10.

5. The therapeutic composition of claim 1 wherein the isolated, recombinant ADI has been modified to remove at least one pegylation site.

6. The therapeutic composition of claim 1 wherein at least one lysine residue has been modified by an amino acid substitution.

7. The therapeutic composition of claim 6 wherein at least 5 lysine residues have been modified by an amino acid substitution.

8. The therapeutic composition of claim 6 wherein at least 10 lysine residues have been modified by an amino acid substitution.

9. The therapeutic composition of claim 6 wherein at least 15 lysine residues have been modified by an amino acid substitution.

10. The therapeutic composition of claim 6 wherein at least 20 lysine residues have been modified by an amino acid substitution.

11. The therapeutic composition of claim 1 wherein the arginine deiminase is covalently bonded via a linker to a PEG molecule.

12. The therapeutic composition of claim 11 wherein the isolated, recombinant ADI is covalently bonded to more than one PEG molecule.

13. The therapeutic composition of claim 11 wherein the isolated, recombinant ADI is covalently bonded to about 1 to about 10 PEG molecules.

14. The therapeutic composition of claim 11 wherein the isolated, recombinant ADI is covalently bonded to about 2 to about 8 PEG molecules.

15. The therapeutic composition of claim 11 wherein the PEG molecules are straight chain or branch chain PEG molecules.

16. The therapeutic composition of claim 11 wherein the PEG has a total weight average molecular weight of from about 1,000 to about 40,000.

17. The therapeutic composition of claim 11 wherein the PEG has a total weight average molecular weight of from about 10,000 to about 30,000.

18. The therapeutic composition of claim 11 wherein the linker is a succinyl group, an amide group, an imide group, a carbamate group, an ester group, an epoxy group, a carboxyl group, a hydroxyl group, a carbohydrate, a tyrosine group, a cysteine group, a histidine group, a methylene group, or any combinations thereof.

19. The therapeutic composition of claim 18 wherein the source of the succinyl group is succinimidyl succinate.

20. The therapeutic composition of claim 1 further comprising a chemotherapeutic agent.

21. The therapeutic composition of claim 20 wherein the chemotherapeutic agent is selected from the group consisting of docetaxel, carboplatin, cyclophosphamide, gemcitabine, cisplatin, sorafenib, sunitinib and everolimus.

22. A method of treating, ameliorating the symptoms of, or inhibiting the progression of a cancer comprising administering to a patient in need thereof a therapeutically effective amount of a therapeutic composition of claim 1, thereby treating, ameliorating the symptoms of, or inhibiting the progression of the cancer.

23. The method of claim 22 wherein the patient in need thereof has been determined to have anti-ADI-PEG 20 antibodies.

24. The method of claim 22 wherein the cancer is selected from the group consisting of hepatocellular carcinoma, melanoma, metastatic melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer.

25. A method of treating, ameliorating the symptoms of, or inhibiting the progression of a cancer comprising administering to a patient in need thereof a therapeutically effective amount of a composition comprising ADI-PEG 20, and after a period of time, administering to the patient a therapeutic composition of claim 1, thereby treating, ameliorating the symptoms of, or inhibiting the progression of the cancer.

26. The method of claim 25 wherein the period of time is determined by detecting a predetermined level of anti-ADI-PEG 20 antibodies in the patient, wherein the therapeutic composition is administered following detection of the predetermined level of said anti-ADI-PEG 20 antibodies.

27. The method of claim 25 wherein the period of time is determined by detecting ADI activity in the patient, wherein the therapeutic composition is administered following detection of a predetermined or reduced level of ADI activity.

* * * * *